(12) United States Patent
Kittleson et al.

(10) Patent No.: US 12,122,810 B2
(45) Date of Patent: Oct. 22, 2024

(54) COMPOSITIONS AND METHODS FOR PRODUCING HIGH SECRETED YIELDS OF RECOMBINANT PROTEINS

(71) Applicant: BOLT THREADS, INC., Emeryville, CA (US)

(72) Inventors: Joshua Kittleson, Pleasant Hill, CA (US); Thomas Stevens, San Francisco, CA (US); Rena Hill, Oakland, CA (US); Carlos Gustavo Pesce, San Francisco, CA (US)

(73) Assignee: BOLT THREADS, INC., Emeryville, CA (US)

( * ) Notice: Subject to any disclaimer, the term of this patent is extended or adjusted under 35 U.S.C. 154(b) by 0 days.

(21) Appl. No.: 17/751,277

(22) Filed: May 23, 2022

(65) Prior Publication Data

US 2022/0306706 A1 Sep. 29, 2022

Related U.S. Application Data

(63) Continuation of application No. 17/138,350, filed on Dec. 30, 2020, now Pat. No. 11,370,815, which is a continuation of application No. 15/920,331, filed on Mar. 13, 2018, now Pat. No. 10,906,947, which is a continuation of application No. PCT/US2018/021817, filed on Mar. 9, 2018.

(60) Provisional application No. 62/470,153, filed on Mar. 10, 2017.

(51) Int. Cl.
| | | |
|---|---|---|
| C07K 14/435 | (2006.01) | |
| C07K 14/395 | (2006.01) | |
| C12N 1/19 | (2006.01) | |
| C12N 15/62 | (2006.01) | |
| C12N 15/81 | (2006.01) | |
| C12P 21/02 | (2006.01) | |

(52) U.S. Cl.
CPC ...... C07K 14/43586 (2013.01); C07K 14/395 (2013.01); C12N 15/625 (2013.01); C12N 15/815 (2013.01); C12P 21/02 (2013.01); C07K 2319/02 (2013.01); C07K 2319/036 (2013.01)

(58) Field of Classification Search
None
See application file for complete search history.

(56) References Cited

U.S. PATENT DOCUMENTS

| | | | |
|---|---|---|---|
| 9,963,554 | B2 | 5/2018 | Widmaier et al. |
| 10,906,947 | B2 | 2/2021 | Kittleson et al. |
| 2003/0013154 | A1 | 1/2003 | Crawford et al. |
| 2003/0203417 | A1 | 10/2003 | Fowlkes et al. |
| 2003/0233675 | A1 | 12/2003 | Cao et al. |
| 2006/0140965 | A1 | 6/2006 | Cassart et al. |
| 2007/0117186 | A1 | 5/2007 | Sahara et al. |
| 2007/0248967 | A1 | 10/2007 | Ohgiya et al. |
| 2011/0124046 | A1 | 5/2011 | Linger et al. |
| 2011/0165681 | A1 | 7/2011 | Boyden et al. |
| 2013/0259862 | A1 | 10/2013 | Nishimura et al. |
| 2014/0212923 | A1 | 7/2014 | Weis et al. |
| 2016/0039911 | A1 | 2/2016 | Lesnicki et al. |
| 2016/0222174 | A1 | 8/2016 | Widmaier et al. |
| 2019/0345471 | A1* | 11/2019 | Miller ............. C12P 19/14 |

FOREIGN PATENT DOCUMENTS

| | | | |
|---|---|---|---|
| EP | 2258855 A1 | 12/2010 | |
| JP | 2016-516412 A | 6/2016 | |
| KR | 10-2014-0060552 A | 5/2014 | |
| WO | 01/77351 A1 | 10/2001 | |
| WO | 03/60141 A1 | 7/2003 | |
| WO | 2003/103706 A2 | 12/2003 | |
| WO | 2005/070962 A1 | 8/2005 | |
| WO | 2007/015178 A2 | 2/2007 | |
| WO | 2008/052043 A2 | 5/2008 | |
| WO | 2010/058057 A1 | 5/2010 | |
| WO | 2010/135678 A1 | 11/2010 | |
| WO | 2012/131302 A1 | 10/2012 | |
| WO | 2014/066374 A1 | 5/2014 | |
| WO | WO-2015042164 A2 * | 3/2015 | ........... B29C 48/022 |
| WO | 2016/077457 A1 | 5/2016 | |
| WO | 2016/149414 A1 | 9/2016 | |
| WO | 2016/201369 A1 | 12/2016 | |

OTHER PUBLICATIONS

U.S. Appl. No. 62/371,681, 2016. (Year: 2016).*
Obst et al., A Modular Toolkit for Generating Pichia pastoris Secretion Libraries, ACS Synthetic Biol. 6, 2017, 1016-25. (Year: 2017).*
Extended European Search Report for EP 18 76 4854, dated Dec. 8, 2020, 14 pages.
Extended European Search Report for EP 18 76 4964, dated Dec. 1, 2020, 13 pages.
Fahnestock, R. et al. "Microbial Production of Spider Silk Proteins," Reviews in Moloecular Biotechnology, 2000, pp. 105-119, vol. 74.
Fitzgerald, I. et al. "Secretion of a Foreign Protein from Budding Yeasts is Enhanced by Cotranslational Translocation and by Suppression of Vacuolar Targeting," Microbial Cell Factories, 2014, pp. 1-12, vol. 13, No. 125.
Gauthier et al., Increase in Xylanase Production by Streptomyces lividans through Simultaneous Use of the Sec- and Tat-Dependent Protein Export Systems, Appl. Environ. Microbial., 2005, 71, 3085-92.
Heiss et al., "Multistep processing of the secretion leader of the extracellular protein Epx1 in Pichia pastoris and implications for protein localization," Microbiology 161:1356-1368, 2015.

(Continued)

*Primary Examiner* — Todd M Epstein
(74) *Attorney, Agent, or Firm* — MARSHALL, GERSTEIN & BORUN LLP

(57) ABSTRACT

The present disclosure relates to methods for producing recombinant proteins, as well as compositions used in and produced by such methods. Specifically, the present disclosure relates to methods for producing high secreted yields of recombinant proteins, and the compositions provided herein include recombinant host cells that comprise polynucleotide sequences encoding proteins operably linked to at least 2 distinct secretion signals.

19 Claims, 9 Drawing Sheets

Specification includes a Sequence Listing.

(56) References Cited

OTHER PUBLICATIONS

International Application No. PCT/US2018/021817, International Preliminary Report on Patentability, mailed Sep. 19, 2019.

La Grange et al., Degradation of Xylan to D-Xylose by Recombinant *Saccharomyces cerevisiae* Coexpressing the Aspergillus niger [3-Xylosidase (xInD) and the Trichoderma reesei Xylanase I (xyn2) Genes, Appl. Environ. Microbiol., 2001, 67, 5512-19.

La Grange et al., Expression of a trichoderma reesei beta-xylanase gene (XYN2) in *Saccharomyces cerevisiae*, Appl. Environ. Microbiol., 1996, 62, 1036-44.

Liang et al., Endogenous signal peptides efficiently mediate the secretion of recombinant proteins in Pichia pastoris, Biotechnol. Lett., 2013, 35, 97-105.

Liu, S.-H. et al. "Improved Secretory Production of Glucoamylase in Pichia pastoris by Combination of Genetic Manipulations," Biochemical and Biophysical Research Communications, 2005, pp. 817-824, vol. 326.

Miller et al., GenBank Accession No. AGW24992, Sep. 25, 2013.

Obst, U. et al. "A Modular Toolkit for Generating Pichia pastoris Secretion Libraries," ACS Synthetic Biology, 2017, pp. 1016-1025, vol. 6.

Paifer et al., Efficient Expression and Secretion of Recombinant Alpha Amylase in Pichia pastoris using two different Signal Sequences, Yeast, 1994, 10, 1415-19.

PCT International Search Report and Written Opinion, PCT Application No. PCT/US18/21812, Aug. 28, 2018, 20 pages.

PCT International Search Report and Written Opinion, PCT Application No. PCT/US18/21817, Aug. 3, 2018, 22 pages.

PCT Invitation to Pay Additional Fees, PCT Application No. PCT/US18/21812, Jun. 15, 2018, 2 pages.

PCT Invitation to Pay Additional Fees, PCT Application No. PCT/US18/21817, Jun. 14, 2018, 2 pages.

Puseenam et al., Co-expression of Endoxylanase and Endoglucanase in Scheffersomyces stipitis and Its Application in Ethanol Production, Appl. Biochem. Biotechnol., 2015, 177, 1690-1700.

Romanos et al., Foreign gene expression in yeast, Yeast, 1992, 8, 423-88.

\* cited by examiner

SEQUENCE LISTING

<160> NUMBER OF SEQ ID NOS: 120

<210> SEQ ID NO 1
<211> LENGTH: 70
<212> TYPE: PRT
<213> ORGANISM: Saccharomyces cerevisiae

<400> SEQUENCE: 1

Ala Pro Val Asn Thr Thr Thr Glu Asp Glu Thr Ala Gln Ile Pro Ala
1               5                   10                  15

Glu Ala Val Ile Gly Tyr Leu Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Leu Asp
    50                  55                  60

Lys Arg Glu Ala Glu Ala
65                  70

<210> SEQ ID NO 2
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Pro Val Asn Thr Thr Thr Glu Asp Glu Thr Ala Gln Ile Pro Ala
1               5                   10                  15

Glu Ala Val Ile Gly Tyr Ser Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Leu Glu
    50                  55                  60

Lys Arg Glu Ala Glu Ala
65                  70

<210> SEQ ID NO 3
<211> LENGTH: 22
<212> TYPE: PRT
<213> ORGANISM: Saccharomyces cerevisiae

<400> SEQUENCE: 3

Met Phe Ser Leu Lys Ala Leu Leu Pro Leu Ala Leu Leu Leu Val Ser
1               5                   10                  15

Ala Asn Gln Val Ala Ala
            20

<210> SEQ ID NO 4
<211> LENGTH: 23
<212> TYPE: PRT
<213> ORGANISM: Pichia pastoris

<400> SEQUENCE: 4

Met Ser Phe Ser Ser Asn Val Pro Gln Leu Phe Leu Leu Leu Val Leu
1               5                   10                  15

Leu Thr Asn Ile Val Ser Gly
            20

<210> SEQ ID NO 5
<211> LENGTH: 20
<212> TYPE: PRT
<213> ORGANISM: Pichia pastoris

<400> SEQUENCE: 5

Met Lys Leu Ser Thr Asn Leu Ile Leu Ala Ile Ala Ala Ser Ala
1               5                   10                  15

Val Val Ser Ala
            20

<210> SEQ ID NO 6
<211> LENGTH: 18
<212> TYPE: PRT
<213> ORGANISM: Gallus gallus

<400> SEQUENCE: 6

Met Arg Ser Leu Leu Ile Leu Val Leu Cys Phe Leu Pro Leu Ala Ala
1               5                   10                  15

Leu Gly

<210> SEQ ID NO 7
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 8
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala
                85

<210> SEQ ID NO 9
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Phe Ser Leu Lys Ala Leu Leu Pro Leu Ala Leu Leu Leu Val Ser
1               5                   10                  15

Ala Asn Gln Val Ala Ala Ala Pro Val Asn Thr Thr Thr Glu Asp Glu
                20                  25                  30

Thr Ala Gln Ile Pro Ala Glu Ala Val Ile Gly Tyr Ser Asp Leu Glu
            35                  40                  45

Gly Asp Phe Asp Val Ala Val Leu Pro Phe Ser Asn Ser Thr Asn Asn
        50                  55                  60

Gly Leu Leu Phe Ile Asn Thr Thr Ile Ala Ser Ile Ala Ala Lys Glu
65                  70                  75                  80

Glu Gly Val Ser Leu Glu Lys Arg Glu Ala Glu Ala
                85                  90

<210> SEQ ID NO 10
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ser Phe Ser Ser Asn Val Pro Gln Leu Phe Leu Leu Leu Val Leu
1               5                   10                  15

Leu Thr Asn Ile Val Ser Gly Ala Pro Val Asn Thr Thr Thr Glu Asp
                20                  25                  30

Glu Thr Ala Gln Ile Pro Ala Glu Ala Val Ile Gly Tyr Ser Asp Leu
            35                  40                  45

Glu Gly Asp Phe Asp Val Ala Val Leu Pro Phe Ser Asn Ser Thr Asn
        50                  55                  60

Asn Gly Leu Leu Phe Ile Asn Thr Thr Ile Ala Ser Ile Ala Ala Lys
65                  70                  75                  80

Glu Glu Gly Val Ser Leu Glu Lys Arg Glu Ala Glu Ala
                85                  90

<210> SEQ ID NO 11
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Lys Leu Ser Thr Asn Leu Ile Leu Ala Ile Ala Ala Ala Ser Ala
1               5                   10                  15

Val Val Ser Ala Ala Pro Val Asn Thr Thr Thr Glu Asp Glu Thr Ala

```
                20                  25                  30
Gln Ile Pro Ala Glu Ala Val Ile Gly Tyr Ser Asp Leu Glu Gly Asp
            35                  40                  45

Phe Asp Val Ala Val Leu Pro Phe Ser Asn Ser Thr Asn Asn Gly Leu
        50                  55                  60

Leu Phe Ile Asn Thr Thr Ile Ala Ser Ile Ala Ala Lys Glu Glu Gly
65                  70                  75                  80

Val Ser Leu Glu Lys Arg Glu Ala Glu Ala
                85                  90

<210> SEQ ID NO 12
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Arg Ser Leu Leu Ile Leu Val Leu Cys Phe Leu Pro Leu Ala Ala
1               5                   10                  15

Leu Gly Ala Pro Val Asn Thr Thr Thr Glu Asp Glu Thr Ala Gln Ile
            20                  25                  30

Pro Ala Glu Ala Val Ile Gly Tyr Ser Asp Leu Glu Gly Asp Phe Asp
        35                  40                  45

Val Ala Val Leu Pro Phe Ser Asn Ser Thr Asn Asn Gly Leu Leu Phe
    50                  55                  60

Ile Asn Thr Thr Ile Ala Ser Ile Ala Ala Lys Glu Glu Gly Val Ser
65                  70                  75                  80

Leu Glu Lys Arg Glu Ala Glu Ala
                85

<210> SEQ ID NO 13
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Gly Tyr Gly Pro Gly Ala Gly Gln Gln Gly Pro Gly Ser Gly Gly
1               5                   10                  15

Gln Gln Gly Pro Gly Gly Gln Pro Tyr Gly Ser Gly Gln Gln Gly
            20                  25                  30

Pro Gly Gly Ala Gly Gln Gln Gly Pro Gly Gln Gly Pro Tyr Gly
        35                  40                  45

Pro Gly Ala Ala Ala Ala Ala Ala Ala Gly Gly Tyr Gly Pro
    50                  55                  60

Gly Ala Gly Gln Gln Gly Pro Gly Ala Gly Gln Gln Gly Pro Gly
65                  70                  75                  80

Ser Gln Gly Pro Gly Gly Gln Gly Pro Tyr Gly Pro Gly Ala Gly Gln
                85                  90                  95

Gln Gly Pro Gly Ser Gln Gly Pro Gly Ser Gly Gln Gly Pro
            100                 105                 110

Gly Gly Gln Gly Pro Tyr Gly Pro Ser Ala Ala Ala Ala Ala
        115                 120                 125

Ala Ala Gly Gly Tyr Gly Pro Gly Ala Gly Gln Arg Ser Gln Gly Pro
```

```
                130                 135                 140
Gly Gly Gln Gly Pro Tyr Gly Pro Ala Gly Gln Gln Gly Pro Gly
145                 150                 155                 160

Ser Gln Gly Pro Gly Ser Gly Gln Gln Gly Pro Gly Gly Gln Gly
                165                 170                 175

Pro Tyr Gly Pro Ser Ala Ala Ala Ala Ala Ala Ala Gly Gly Tyr
                180                 185                 190

Gly Pro Gly Ala Gly Gln Gln Gly Pro Gly Ser Gln Gly Pro Gly Ser
            195                 200                 205

Gly Gly Gln Gln Gly Pro Gly Gly Gln Gly Pro Tyr Gly Pro Gly Ala
        210                 215                 220

Ala Ala Ala Ala Ala Val Gly Gly Tyr Gly Pro Gly Ala Gly Gln
225                 230                 235                 240

Gln Gly Pro Gly Ser Gln Gly Pro Gly Ser Gly Gly Gln Gln Gly Pro
            245                 250                 255

Gly Gly Gln Gly Pro Tyr Gly Pro Ser Ala Ala Ala Ala Ala Ala
                260                 265                 270

Ala Gly Gly Tyr Gly Pro Gly Ala Gly Gln Gln Gly Pro Gly Ser Gln
        275                 280                 285

Gly Pro Gly Ser Gly Gly Gln Gln Gly Pro Gly Gly Gln Gly Pro Tyr
    290                 295                 300

Gly Pro Ser Ala Ala Ala Ala Ala Ala Ala
305                 310                 315

<210> SEQ ID NO 14
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Gly Gln Gly Gly Arg Gly Gly Phe Gly Gly Leu Gly Ser Gln Gly
1               5                   10                  15

Ala Gly Gly Ala Gly Gln Gly Gly Ala Gly Ala Ala Ala Ala Ala Ala
            20                  25                  30

Ala Ala Gly Gly Asp Gly Gly Ser Gly Leu Gly Gly Tyr Gly Ala Gly
        35                  40                  45

Arg Gly His Gly Val Gly Leu Gly Gly Ala Gly Gly Ala Gly Ala Ala
    50                  55                  60

Ser Ala Ala Ala Ala Ala Gly Gly Gln Gly Gly Arg Gly Gly Phe Gly
65                  70                  75                  80

Gly Leu Gly Ser Gln Gly Ala Gly Gly Ala Gly Gln Gly Gly Ala Gly
                85                  90                  95

Ala Ala Ala Ala Ala Ala Ala Gly Gly Asp Gly Gly Ser Gly Leu
            100                 105                 110

Gly Gly Tyr Gly Ala Gly Arg Gly His Gly Ala Gly Leu Gly Gly Ala
        115                 120                 125

Gly Gly Ala Gly Ala Ala Ser Ala Ala Ala Ala Ala Gly Gly Gln Gly
    130                 135                 140

Gly Arg Gly Gly Phe Gly Gly Leu Gly Ser Gln Gly Ser Gly Gly Ala
145                 150                 155                 160

Gly Gln Gly Gly Ser Gly Ala Ala Ala Ala Ala Ala Ala Gly Gly
                165                 170                 175
```

```
Asp Gly Gly Ser Gly Leu Gly Gly Tyr Gly Ala Gly Arg Gly Tyr Gly
            180                 185                 190

Ala Gly Leu Gly Gly Ala Gly Gly Ala Gly Ala Ala Ser Ala Ala Ala
        195                 200                 205

Ala Ala Gly Gly Gln Gly Gly Arg Gly Gly Phe Gly Gly Leu Gly Ser
    210                 215                 220

Gln Gly Ala Gly Gly Ala Gly Gln Gly Gly Ser Gly Ala Ala Ala
225                 230                 235                 240

Ala Ala Ala Ala Val Ala Asp Gly Gly Ser Gly Leu Gly Gly Tyr Gly
                245                 250                 255

Ala Gly Arg Gly Tyr Gly Ala Gly Leu Gly Gly Ala Gly Gly Ala Gly
            260                 265                 270

Ala Ala Ser Ala Ala Ala Ala Thr
        275                 280

<210> SEQ ID NO 15
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Ser Ala Pro Gln Gly Ala Gly Gly Pro Ala Pro Gln Gly Pro Ser
1               5                   10                  15

Gln Gln Gly Pro Val Ser Gln Gly Pro Tyr Gly Pro Gly Ala Ala Ala
            20                  25                  30

Ala Ala Ala Ala Ala Gly Gly Tyr Gly Pro Gly Ala Gly Gln Gln Gly
        35                  40                  45

Pro Gly Ser Gln Gly Pro Gly Ser Gly Gly Gln Gln Pro Gly Ser
    50                  55                  60

Gln Gly Pro Gly Ser Gly Gly Gln Gln Gly Pro Gly Gly Gln Gly Pro
65                  70                  75                  80

Tyr Gly Pro Ser Ala Ala Ala Ala Ala Ala Ala Ala Gly Gly Tyr
                85                  90                  95

Gly Pro Gly Ala Gly Gln Gln Gly Pro Gly Ser Gln Gly Pro Gly Ser
            100                 105                 110

Gly Gly Gln Gln Gly Pro Gly Gly Gln Gly Pro Tyr Gly Pro Gly Ala
        115                 120                 125

Ala Ala Ala Ala Ala Val Gly Gly Tyr Gly Pro Gly Ala Gly Gln
    130                 135                 140

Gln Gly Pro Gly Ser Gln Gly Pro Gly Ser Gly Gly Gln Gln Gly Pro
145                 150                 155                 160

Gly Gly Gln Gly Pro Tyr Gly Pro Ser Ala Ala Ala Ala Ala Ala
                165                 170                 175

Ala Gly Gly Tyr Gly Pro Gly Ala Gly Gln Gln Gly Pro Gly Ser Gln
            180                 185                 190

Gly Pro Gly Ser Gly Gly Gln Gln Gly Pro Gly Gly Gln Gly Pro Tyr
        195                 200                 205

Gly Pro Ser Ala Ala Ala Ala Ala Ala Ala Gly Gly Tyr Gly Pro
    210                 215                 220

Gly Ala Gly Gln Gln Gly Pro Gly Ser Gly Gly Gln Gln Gly Pro Gly
225                 230                 235                 240

Gly Gln Gly Pro Tyr Gly Ser Gly Gln Gln Gly Pro Gly Gly Ala Gly
                245                 250                 255
```

-continued

Gln Gln Gly Pro Gly Gln Gly Pro Tyr Gly Pro Gly Ala Ala Ala
            260                 265                 270

Ala Ala Ala Ala Ala Ala
            275

<210> SEQ ID NO 16
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Gly Tyr Gly Pro Gly Ala Gly Gln Gln Gly Pro Gly Ser Gly Gly
1               5                   10                  15

Gln Gln Gly Pro Gly Gln Gly Pro Tyr Gly Ser Gly Gln Gln Gly
            20                  25                  30

Pro Gly Gly Ala Gly Gln Gln Gly Pro Gly Gly Gln Gly Pro Tyr Gly
            35                  40                  45

Pro Gly Ala Ala Ala Ala Ala Ala Ala Gly Gly Tyr Gly Pro
        50                  55                  60

Gly Ala Gly Gln Gln Gly Pro Gly Ala Gly Gln Gln Pro Gly
65                  70                  75                  80

Ser Gln Gly Pro Gly Gln Gly Pro Tyr Gly Pro Gly Ala Gly Gln
                85                  90                  95

Gln Gly Pro Gly Ser Gln Gly Pro Gly Ser Gly Gly Gln Gly Pro
            100                 105                 110

Gly Gly Gln Gly Pro Tyr Gly Pro Ser Ala Ala Ala Ala Ala Ala
            115                 120                 125

Ala Gly Gly Tyr Gly Pro Gly Ala Gly Gln Gln Gly Pro Gly Ser Gln
            130                 135                 140

Gly Pro Gly Ser Gly Gly Gln Gln Gly Pro Gly Gly Gln Gly Pro Tyr
145                 150                 155                 160

Gly Pro Ser Ala Ala Ala Ala Ala Ala Ala Gly Gly Tyr Gly Pro
                165                 170                 175

Gly Ala Gly Gln Gln Gly Pro Gly Ser Gly Gly Gln Gln Gly Pro Gly
            180                 185                 190

Gly Gln Gly Pro Tyr Gly Ser Gly Gln Gln Gly Pro Gly Gly Ala Gly
            195                 200                 205

Gln Gln Gly Pro Gly Gly Gln Gly Pro Tyr Gly Gly Tyr Gly Pro
            210                 215                 220

Gly Ala Gly Gln Gln Gly Pro Gly Ser Gln Gly Pro Gly Ser Gly Gly
225                 230                 235                 240

Gln Gln Gly Pro Gly Gly Gln Gly Pro Tyr Gly Pro Ser Ala Ala Ala
                245                 250                 255

Ala Ala Ala Ala Ala
            260

<210> SEQ ID NO 17
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

-continued

Gly Pro Gly Ala Arg Arg Gln Gly Pro Gly Ser Gln Gly Pro Gly Ser
1               5                   10                  15

Gly Gly Gln Gln Gly Pro Gly Gly Gln Gly Pro Tyr Gly Ser Gly Gln
                20                  25                  30

Gln Gly Pro Gly Gly Ala Gly Gln Gly Pro Gly Gly Gln Gly Pro
            35                  40                  45

Tyr Gly Pro Gly Ala Ala Ala Ala Ala Ala Ala Ala Gly Gly Tyr
    50                  55                  60

Gly Pro Gly Ala Gly Gln Gln Gly Pro Gly Gly Ala Gly Gln Gln Gly
65                  70                  75                  80

Pro Gly Ser Gln Gly Pro Gly Gln Gly Pro Tyr Gly Pro Gly Ala
                85                  90                  95

Gly Gln Gln Gly Pro Gly Ser Gln Gly Pro Gly Ser Gly Gly Gln Gln
                100                 105                 110

Gly Pro Gly Gly Gln Gly Pro Tyr Gly Pro Ser Ala Ala Ala Ala
            115                 120                 125

Ala Ala Ala Ala Gly Gly Tyr Gly Pro Gly Ala Gly Gln Gln Gly Pro
    130                 135                 140

Gly Ser Gln Gly Pro Gly Ser Gly Gly Gln Gln Gly Pro Gly Gly Gln
145                 150                 155                 160

Gly Pro Tyr Gly Pro Gly Ala Ala Ala Ala Ala Ala Val Gly Gly
            165                 170                 175

Tyr Gly Pro Gly Ala Gly Gln Gln Gly Pro Gly Ser Gln Gly Pro Gly
    180                 185                 190

Ser Gly Gly Gln Gln Gly Pro Gly Gln Gly Pro Tyr Gly Pro Ser
            195                 200                 205

Ala Ala Ala Ala Ala Ala Ala Ala Gly Gly Tyr Gly Pro Gly Ala Gly
    210                 215                 220

Gln Gln Gly Pro Gly Ser Gln Gly Pro Gly Ser Gly Gly Gln Gln Gly
225                 230                 235                 240

Pro Gly Gly Gln Gly Pro Tyr Gly Pro Ser Ala Ala Ala Ala Ala
            245                 250                 255

Ala Ala

<210> SEQ ID NO 18
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Pro Gly Ala Arg Arg Gln Gly Pro Gly Ser Gln Gly Pro Gly Ser
1               5                   10                  15

Gly Gly Gln Gln Gly Pro Gly Gly Gln Gly Pro Tyr Gly Ser Gly Gln
                20                  25                  30

Gln Gly Pro Gly Gly Ala Gly Gln Gly Pro Gly Gly Gln Gly Pro
            35                  40                  45

Tyr Gly Pro Gly Ala Ala Ala Ala Ala Ala Ala Ala Gly Gly Tyr
    50                  55                  60

Gly Pro Gly Ala Gly Gln Gln Gly Pro Gly Gly Ala Gly Gln Gln Gly
65                  70                  75                  80

Pro Gly Ser Gln Gly Pro Gly Gly Gln Gly Pro Tyr Gly Pro Gly Ala
                85                  90                  95

Gly Gln Gln Gly Pro Gly Ser Gln Gly Pro Gly Ser Gly Gly Gln Gln
                100                 105                 110

Gly Pro Gly Gly Gln Gly Pro Tyr Gly Pro Ser Ala Ala Ala Ala Ala
            115                 120                 125

Ala Ala Ala Gly Gly Tyr Gly Pro Gly Ala Gly Gln Gln Gly Pro Gly
130                 135                 140

Ser Gln Gly Pro Gly Ser Gly Gly Gln Gln Gly Pro Gly Gly Gln Gly
145                 150                 155                 160

Pro Tyr Gly Pro Gly Ala Ala Ala Ala Ala Ala Val Gly Tyr
            165                 170                 175

Gly Pro Gly Ala Gly Gln Gln Gly Pro Ser Gln Pro Gly Ser
            180                 185                 190

Gly Gly Gln Gln Gly Pro Gly Gly Gln Gly Pro Tyr Gly Pro Ser Ala
            195                 200                 205

Ala Ala Ala Ala Ala Ala Gly Gly Tyr Gly Pro Gly Ala Gly Gln
210                 215                 220

Gln Gly Pro Gly Ser Gln Gly Pro Ser Gly Gly Gln Gln Gly Pro
225                 230                 235                 240

Gly Gly Gln Gly Pro Tyr Gly Pro Ser Ala Ala Ala Ala Ala Ala
                245                 250                 255

Ala

<210> SEQ ID NO 19
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Gly Tyr Gly Pro Gly Ala Gly Gln Gln Gly Pro Gly Ser Gly Gly
1               5                   10                  15

Gln Gln Gly Pro Gly Gly Gln Gly Pro Tyr Gly Ser Gly Gln Gln Gly
            20                  25                  30

Pro Gly Gly Ala Gly Gln Gln Gly Pro Gly Gly Gln Gly Pro Tyr Gly
        35                  40                  45

Pro Gly Ala Ala Ala Ala Ala Ala Ala Ala Gly Gly Tyr Gly Pro
    50                  55                  60

Gly Ala Gly Gln Gln Gly Pro Gly Ala Gly Gln Gln Gly Pro Glu
65                  70                  75                  80

Gly Pro Gly Ser Gln Gly Pro Gly Ser Gly Gly Gln Gln Gly Pro Gly
                85                  90                  95

Gly Gln Gly Pro Tyr Gly Pro Gly Ala Ala Ala Ala Ala Ala Val
            100                 105                 110

Gly Gly Tyr Gly Pro Gly Ala Gly Gln Gln Gly Pro Gly Ser Gln Gly
            115                 120                 125

Pro Gly Ser Gly Gly Gln Gln Gly Pro Gly Gly Gln Gly Pro Tyr Gly
        130                 135                 140

Pro Ser Ala Ala Ala Ala Ala Ala Ala Gly Gly Tyr Gly Pro Gly
145                 150                 155                 160

Ala Gly Gln Gln Gly Pro Gly Ser Gly Pro Gly Ser Gly Gly Gln
            165                 170                 175

Gln Gly Pro Gly Gly Gln Gly Pro Tyr Gly Pro Ser Ala Ala Ala Ala
            180                 185                 190

```
Ala Ala Ala Ala Gly Gly Tyr Gly Pro Gly Ala Gly Gln Gln Gly Pro
            195                 200                 205

Gly Ser Gly Gly Gln Gln Gly Pro Gly Gly Gln Gly Pro Tyr Gly Ser
        210                 215                 220

Gly Gln Gln Gly Pro Gly Gly Ala Gly Gln Gln Gly Pro Gly Gly Gln
225                 230                 235                 240

Gly Pro Tyr Gly Pro Gly Ala Ala Ala Ala Ala Ala Ala Ala
            245                 250                 255

<210> SEQ ID NO 20
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Val Phe Ser Ala Gly Gln Gly Ala Thr Pro Trp Glu Asn Ser Gln
1               5                   10                  15

Leu Ala Glu Ser Phe Ile Ser Arg Phe Leu Arg Phe Ile Gly Gln Ser
            20                  25                  30

Gly Ala Phe Ser Pro Asn Gln Leu Asp Asp Met Ser Ser Ile Gly Asp
        35                  40                  45

Thr Leu Lys Thr Ala Ile Glu Lys Met Ala Gln Ser Arg Lys Ser Ser
50                  55                  60

Lys Ser Lys Leu Gln Ala Leu Asn Met Ala Phe Ala Ser Ser Met Ala
65                  70                  75                  80

Glu Ile Ala Val Ala Glu Gln Gly Gly Leu Ser Leu Glu Ala Lys Thr
                85                  90                  95

Asn Ala Ile Ala Ser Ala Leu Ser Ala Ala Phe Leu Glu Thr Thr Gly
            100                 105                 110

Tyr Val Asn Gln Gln Phe Val Asn Glu Ile Lys Thr Leu Ile Phe Met
        115                 120                 125

Ile Ala Gln Ala Ser Ser Asn Glu Ile Ser Gly Ser Ala Ala Ala Ala
130                 135                 140

Gly Gly Ser Ser Gly Gly Gly Gly Ser Gly Gln Gly Gly Tyr Gly
145                 150                 155                 160

Gln Gly Ala Tyr Ala Ser Ala Ser Ala Ala Ala Tyr Gly Ser Ala
                165                 170                 175

Pro Gln Gly Thr Gly Gly Pro Ala Ser Gln Pro Ser Gln Gln Gly
            180                 185                 190

Pro Val Ser Gln Pro Ser Tyr Gly Pro Ser Ala Thr Val Ala Val Thr
        195                 200                 205

Ala Val Gly Gly Arg Pro Gln Gly Pro Ser Ala Pro Arg Gln Gln Gly
210                 215                 220

Pro Ser Gln Gln Gly Pro Gly Gln Gln Gly Pro Gly Gly Arg Gly Pro
225                 230                 235                 240

Tyr Gly Pro Ser Ala Ala Ala Ala Ala Ala Ala Ala
            245                 250

<210> SEQ ID NO 21
<211> LENGTH: 252
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 21

Gly Ala Gly Ala Gly Ala Gly Ala Gly Ala Gly Ala Gly Ala Gly Ala
1               5                   10                  15

Gly Ser Gly Ala Ser Thr Ser Val Ser Thr Ser Ser Ser Gly Ser
            20                  25                  30

Gly Ala Gly Ala Gly Ala Gly Ser Gly Ala Gly Ser Gly Ala Gly Ala
        35                  40                  45

Gly Ser Gly Ala Gly Ala Gly Ala Gly Ala Gly Ala Gly Ala Gly
    50                  55                  60

Phe Gly Ser Gly Leu Gly Leu Gly Tyr Gly Val Gly Leu Ser Ser Ala
65                  70                  75                  80

Gln Ala Gln Ala Gln Ala Gln Ala Ala Ala Gln Ala Gln Ala Gln Ala
                85                  90                  95

Gln Ala Gln Ala Tyr Ala Ala Ala Gln Ala Gln Ala Gln Ala Gln Ala
            100                 105                 110

Gln Ala Gln Ala Ala Ala Ala Ala Ala Ala Ala Ala Ala Gly Ala
            115                 120                 125

Gly Ala Gly Ala Gly Ala Gly Ala Gly Ala Gly Ala Gly Ala Gly Ser
        130                 135                 140

Gly Ala Ser Thr Ser Val Ser Thr Ser Ser Ser Gly Ser Gly Ala
145                 150                 155                 160

Gly Ala Gly Ala Gly Ser Gly Ala Gly Ser Gly Ala Gly Ala Gly Ser
            165                 170                 175

Gly Ala Gly Ala Gly Ala Gly Ala Gly Ala Gly Ala Gly Phe Gly
        180                 185                 190

Ser Gly Leu Gly Leu Gly Tyr Gly Val Gly Leu Ser Ser Ala Gln Ala
        195                 200                 205

Gln Ala Gln Ala Gln Ala Ala Ala Gln Ala Gln Ala Gln Ala Gln Ala
    210                 215                 220

Gln Ala Tyr Ala Ala Ala Gln Ala Gln Ala Gln Ala Gln Ala Gln Ala
225                 230                 235                 240

Gln Ala Ala Ala Ala Ala Ala Ala Ala Ala Ala
            245                 250

<210> SEQ ID NO 22
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Ala Gly Ala Gly Ala Gly Ala Gly Ala Gly Ala Gly Ala Gly Ala
1               5                   10                  15

Gly Ser Gly Ala Ser Thr Ser Val Ser Thr Ser Ser Ser Gly Ser
            20                  25                  30

Gly Ala Gly Ala Gly Ala Gly Ser Gly Ala Gly Ser Gly Ala Gly Ala
        35                  40                  45

Gly Ser Gly Ala Gly Ala Gly Ala Gly Ala Gly Ala Gly Ala Ala
    50                  55                  60

Phe Gly Ser Gly Leu Gly Leu Gly Tyr Gly Val Gly Leu Ser Ser Ala
65                  70                  75                  80

Gln Ala Gln Ala Gln Ala Gln Ala Ala Ala Gln Ala Gln Ala Asp Ala

```
                85                  90                  95
Gln Ala Gln Ala Tyr Ala Ala Gln Ala Gln Ala Gln Ala Gln Ala
            100                 105                 110
Gln Ala Gln Ala Ala Ala Ala Ala Ala Ala Ala Gly Ala
            115                 120                 125
Gly Ala Gly Ala Gly Ala Gly Ser Gly Ala Gly Ala Gly Ala Gly Ser
130                 135                 140
Gly Ala Ser Thr Ser Val Ser Thr Ser Ser Ser Gly Ser Gly Ala
145                 150                 155                 160
Gly Ala Gly Ala Gly Ser Gly Ala Gly Ser Gly Ala Gly Ala Gly Ser
                165                 170                 175
Gly Ala Gly Ala Gly Ala Gly Ala Gly Gly Ala Gly Ala Gly Phe Gly
                180                 185                 190
Ser Gly Leu Gly Leu Gly Tyr Gly Val Gly Leu Ser Ser Ala Gln Ala
                195                 200                 205
Gln Ala Gln Ala Gln Ala Ala Gln Ala Gln Ala Asp Ala Gln Ala
            210                 215                 220
Gln Ala Tyr Ala Ala Ala Gln Ala Gln Ala Gln Ala Gln Ala Gln Ala
225                 230                 235                 240
Gln Ala Ala Ala Ala Ala Ala Ala Ala Ala
                245                 250

<210> SEQ ID NO 23
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Ala Gly Ala Gly Ala Gly Ala Gly Ser Gly Ala Gly Ala Gly Ala
1               5                   10                  15
Gly Ser Gly Ala Ser Thr Ser Val Ser Thr Ser Ser Ser Ser Gly Ser
                20                  25                  30
Gly Ala Gly Ala Gly Ala Gly Ser Gly Ala Gly Ser Gly Ala Gly Ala
                35                  40                  45
Gly Ser Gly Ala Gly Ala Gly Ala Gly Ala Gly Gly Ala Gly Ala Gly
                50                  55                  60
Phe Gly Ser Gly Leu Gly Leu Gly Tyr Gly Val Gly Leu Ser Ser Ala
65                  70                  75                  80
Gln Ala Gln Ala Gln Ser Ala Ala Ala Arg Ala Gln Ala Asp Ala
            85                  90                  95
Gln Ala Gln Ala Tyr Ala Ala Ala Gln Ala Gln Ala Gln Ala Gln Ala
            100                 105                 110
Gln Ala Gln Ala Ala Ala Ala Ala Ala Ala Ala Ala Gly Ala
            115                 120                 125
Gly Ala Gly Ala Gly Ala Gly Ala Gly Ala Gly Ala Gly Ala Gly Ser
                130                 135                 140
Gly Ala Ser Thr Ser Val Ser Thr Ser Ser Ser Ala Ser Gly Ala
145                 150                 155                 160
Gly Ala Gly Ala Gly Ser Gly Ala Gly Ser Gly Ala Gly Ala Gly Ser
                165                 170                 175
Gly Ala Gly Ala Gly Ala Gly Ala Gly Gly Ala Gly Ala Gly Phe Gly
                180                 185                 190
```

```
Ser Gly Leu Gly Leu Gly Tyr Gly Val Gly Leu Ser Ser Ala Gln Ala
            195                 200                 205

Gln Ala Gln Ala Gln Ala Ala Gln Ala Gln Ala Gln Ala Gln Ala
    210                 215                 220

Gln Ala Leu Ala Ala Gln Ala Gln Ala Gln Ala Gln Ala Gln Ala
225                 230                 235                 240

Gln Ala Ala Ala Thr Ala Ala Ala Ala Ala
            245                 250

<210> SEQ ID NO 24
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Gly Tyr Gly Pro Gly Ala Gly Gln Gln Gly Pro Gly Gly Ala Gly
1               5                   10                  15

Gln Gln Gly Pro Gly Ser Gln Gly Pro Gly Gly Gln Gly Pro Tyr Gly
            20                  25                  30

Pro Gly Ala Gly Gln Gln Gly Pro Gly Ser Gln Gly Pro Gly Ser Gly
        35                  40                  45

Gly Gln Gln Gly Pro Gly Gln Gly Pro Tyr Gly Pro Ser Ala Ala
    50                  55                  60

Ala Ala Ala Ala Ala Ala Gly Gly Tyr Gly Pro Gly Ala Gly Gln Gln
65                  70                  75                  80

Gly Pro Gly Ser Gln Gly Pro Gly Ser Gly Gly Gln Gln Gly Pro Gly
                85                  90                  95

Ser Gln Gly Pro Gly Ser Gly Gly Gln Gln Gly Pro Gly Gly Gln Gly
            100                 105                 110

Pro Tyr Gly Pro Ser Ala Ala Ala Ala Ala Ala Ala Ala Gly Gly
        115                 120                 125

Tyr Gly Pro Gly Ala Gly Gln Gln Gly Pro Gly Ser Gln Gly Pro Gly
    130                 135                 140

Ser Gly Gly Gln Gln Gly Pro Gly Gln Gly Pro Tyr Gly Pro Gly
145                 150                 155                 160

Ala Ala Ala Ala Ala Ala Ala Val Gly Gly Tyr Gly Pro Gly Ala Gly
                165                 170                 175

Gln Gln Gly Pro Gly Ser Gln Gly Pro Gly Ser Gly Gly Gln Gln Gly
            180                 185                 190

Pro Gly Gly Gln Gly Pro Tyr Gly Pro Ser Ala Ala Ala Ala Ala
        195                 200                 205

Ala Ala Gly Gly Tyr Gly Pro Gly Ala Gly Gln Gln Gly Pro Gly Ser
    210                 215                 220

Gln Gly Pro Gly Ser Gly Gly Gln Gln Gly Pro Gly Gly Gln Gly Pro
225                 230                 235                 240

Tyr Gly Pro Ser Ala Ala Ala Ala Ala Ala Ala
                245                 250

<210> SEQ ID NO 25
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 25

```
Gly Gly Tyr Gly Pro Gly Ala Gly Gln Gln Gly Pro Gly Gly Ala Gly
1               5                   10                  15
Gln Gln Gly Pro Gly Ser Gln Gly Pro Gly Gly Gln Gly Pro Tyr Gly
            20                  25                  30
Pro Gly Ala Gly Gln Gln Gly Pro Gly Ser Gln Gly Pro Gly Ser Gly
        35                  40                  45
Gly Gln Gln Gly Pro Gly Gly Gln Gly Pro Tyr Gly Pro Ser Ala Ala
    50                  55                  60
Ala Ala Ala Ala Ala Gly Gly Tyr Gly Pro Gly Ala Gly Gln Gln
65                  70                  75                  80
Gly Pro Gly Ser Gln Gly Pro Gly Ser Gly Gly Gln Gln Gly Pro Gly
            85                  90                  95
Ser Gln Gly Pro Gly Ser Gly Gly Gln Gln Gly Pro Gly Gly Gln Gly
                100                 105                 110
Pro Tyr Gly Pro Ser Ala Ala Ala Ala Ala Ala Gly Gly Tyr
            115                 120                 125
Gly Pro Gly Ala Gly Gln Gln Gly Pro Gly Ser Gln Gly Pro Gly Ser
    130                 135                 140
Gly Gly Gln Gln Gly Pro Gly Gly Gln Gly Pro Tyr Gly Pro Gly Ala
145                 150                 155                 160
Ala Ala Ala Ala Ala Val Gly Gly Tyr Gly Pro Gly Ala Gly Gln
                165                 170                 175
Gln Gly Pro Gly Ser Gln Gly Pro Gly Ser Gly Gly Gln Gln Gly Pro
            180                 185                 190
Gly Gly Gln Gly Pro Tyr Gly Pro Ser Ala Ala Ala Ala Ala Ala
        195                 200                 205
Ala Gly Gly Tyr Gly Pro Gly Ala Gly Gln Gln Gly Pro Gly Ser Gln
210                 215                 220
Gly Pro Gly Ser Gly Gly Gln Gln Gly Pro Gly Gly Gln Gly Pro Tyr
225                 230                 235                 240
Gly Pro Ser Ala Ala Ala Ala Ala Ala Ala
                245                 250
```

<210> SEQ ID NO 26
<211> LENGTH: 248
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

```
Gly His Gln Gly Pro His Arg Lys Thr Pro Trp Glu Thr Pro Glu Met
1               5                   10                  15
Ala Glu Asn Phe Met Asn Asn Val Arg Glu Asn Leu Glu Ala Ser Arg
            20                  25                  30
Ile Phe Pro Asp Glu Leu Met Lys Asp Met Glu Ala Ile Thr Asn Thr
        35                  40                  45
Met Ile Ala Ala Val Asp Gly Leu Glu Ala Gln His Arg Ser Ser Tyr
    50                  55                  60
Ala Ser Leu Gln Ala Met Asn Thr Ala Phe Ala Ser Ser Met Ala Gln
65                  70                  75                  80
Leu Phe Ala Thr Glu Gln Asp Tyr Val Asp Thr Glu Val Ile Ala Gly
            85                  90                  95
```

```
Ala Ile Gly Lys Ala Tyr Gln Gln Ile Thr Gly Tyr Glu Asn Pro His
                100                 105                 110

Leu Ala Ser Glu Val Thr Arg Leu Ile Gln Leu Phe Arg Glu Glu Asp
            115                 120                 125

Asp Leu Glu Asn Glu Val Glu Ile Ser Phe Ala Asp Thr Asp Asn Ala
        130                 135                 140

Ile Ala Arg Ala Ala Ala Gly Ala Ala Ala Gly Ser Ala Ala Ala Ser
145                 150                 155                 160

Ser Ser Ala Asp Ala Ser Ala Thr Ala Glu Gly Ala Ser Gly Asp Ser
                165                 170                 175

Gly Phe Leu Phe Ser Thr Gly Thr Phe Gly Arg Gly Gly Ala Gly Ala
            180                 185                 190

Gly Ala Gly Ala Ala Ala Ala Ser Ala Ala Ala Ser Ala Ala Ala
            195                 200                 205

Ala Gly Ala Glu Gly Asp Arg Gly Leu Phe Phe Ser Thr Gly Asp Phe
        210                 215                 220

Gly Arg Gly Gly Ala Gly Ala Gly Ala Gly Ala Ala Ala Ala Ser Ala
225                 230                 235                 240

Ala Ala Ala Ser Ala Ala Ala Ala
                245
```

<210> SEQ ID NO 27
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gly Gly Ala Gln Lys His Pro Ser Gly Glu Tyr Ser Val Ala Thr Ala
1               5                   10                  15

Ser Ala Ala Ala Thr Ser Val Thr Ser Gly Gly Ala Pro Val Gly Lys
                20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
        50                  55                  60

Gly Pro Ile Gly Gly Val Gly Glu Ser Asn Thr Phe Ser Ser Ser Phe
65                  70                  75                  80

Ala Ser Ala Leu Gly Gly Asn Arg Gly Phe Ser Gly Val Ile Ser Ser
                85                  90                  95

Ala Ser Ala Thr Ala Val Ala Ser Ala Phe Gln Lys Gly Leu Ala Pro
                100                 105                 110

Tyr Gly Thr Ala Phe Ala Leu Ser Ala Ala Ser Ala Ala Ala Asp Ala
            115                 120                 125

Tyr Asn Ser Ile Gly Ser Gly Ala Ser Ala Ser Ala Tyr Ala Gln Ala
        130                 135                 140

Phe Ala Arg Val Leu Tyr Pro Leu Leu Gln Gln Tyr Gly Leu Ser Ser
145                 150                 155                 160

Ser Ala Asp Ala Ser Ala Phe Ala Ser Ala Ile Ala Ser Ser Phe Ser
                165                 170                 175

Thr Gly Val Ala Gly Gln Gly Pro Ser Val Pro Tyr Val Gly Gln Gln
            180                 185                 190

Gln Pro Ser Ile Met Val Ser Ala Ala Ser Ala Ser Ala Ala Ala Ser
```

```
                195                 200                 205
Ala Ala Ala Val Gly Gly Pro Val Val Gln Gly Pro Tyr Asp Gly
        210                 215                 220

Gly Gln Pro Gln Gln Pro Asn Ile Ala Ala Ser Ala Ala Ala Ala
225                 230                 235                 240

Thr Ala Thr Ser Ser
                245

<210> SEQ ID NO 28
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Gly Gln Gly Gly Arg Gly Gly Phe Gly Gly Leu Gly Ser Gln Gly
1               5                   10                  15

Glu Gly Gly Ala Gly Gln Gly Gly Ala Gly Ala Ala Ala Ala Ala Ala
            20                  25                  30

Ala Ala Gly Ala Asp Gly Gly Phe Gly Leu Gly Gly Tyr Gly Ala Gly
        35                  40                  45

Arg Gly Tyr Gly Ala Gly Leu Gly Gly Ala Gly Ala Gly Ala Ala
50                  55                  60

Ser Ala Ala Ala Ala Gly Gly Gln Gly Gly Arg Ser Phe Gly
65                  70                  75                  80

Gly Leu Gly Ser Gln Gly Ala Gly Gly Ala Gln Gly Gly Ala Gly
                85                  90                  95

Ala Ala Ala Ala Ala Ala Ala Gly Ala Asp Gly Gly Ser Gly Leu
            100                 105                 110

Gly Gly Tyr Gly Ala Gly Arg Gly Tyr Gly Ala Ser Leu Gly Gly Ala
        115                 120                 125

Asp Gly Ala Gly Ala Ala Ser Ala Ala Ala Ala Gly Gly Gln Gly
        130                 135                 140

Gly Arg Gly Gly Phe Gly Gly Leu Gly Ser Gln Gly Ala Gly Gly Ala
145                 150                 155                 160

Gly Gln Gly Gly Ala Gly Ala Ala Ala Ala Ala Ala Ala Ser Gly
            165                 170                 175

Asp Gly Gly Ser Gly Leu Gly Gly Tyr Gly Ala Gly Arg Gly Tyr Gly
        180                 185                 190

Ala Gly Leu Gly Gly Ala Gly Ala Gly Ala Ala Ser Ala Ala Ala
        195                 200                 205

Ala Ala Gly Gly Glu Gly Gly Arg Gly Gly Phe Gly Gly Leu Gly Ser
        210                 215                 220

Gln Gly Ala Gly Gly Ala Gly Gln Gly Gly Ser Leu Ala Ala Ala
225                 230                 235                 240

Ala Ala Ala Ala

<210> SEQ ID NO 29
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

Gly Pro Gly Gly Tyr Gly Gly Pro Gly Gln Pro Gly Pro Gly Gln Gly
1               5                   10                  15

Gln Tyr Gly Pro Gly Pro Gln Gln Gly Pro Arg Gln Gly Gly Gln
            20                  25                  30

Gln Gly Pro Ala Ser Ala Ala Ala Ala Ala Ala Gly Pro Gly Gly
            35                  40                  45

Tyr Gly Gly Pro Gly Gln Gln Gly Pro Arg Gln Gly Gln Gln Gly
    50                  55                  60

Pro Ala Ser Ala Ala Ala Ala Ala Ala Ala Ala Gly Pro Arg
65                  70                  75              80

Gly Tyr Gly Gly Pro Gly Gln Gln Gly Pro Val Gln Gly Gln Gln
                85                  90                  95

Gly Pro Ala Ser Ala Ala Ala Ala Ala Ala Gly Val Gly Gly
            100                 105                 110

Tyr Gly Gly Pro Gly Gln Gln Gly Pro Gly Gln Gly Gln Tyr Gly Pro
            115                 120                 125

Gly Thr Gly Gln Gln Gly Gln Gly Pro Ser Gly Gln Gln Gly Pro Ala
    130                 135                 140

Gly Ala Ala Ala Ala Ala Gly Gly Ala Ala Gly Pro Gly Gly Tyr
145                 150                 155                 160

Gly Gly Pro Gly Gln Gln Gly Pro Gly Gln Gly Gln Tyr Gly Pro Gly
                165                 170                 175

Thr Gly Gln Gln Gly Gln Gly Pro Ser Gly Gln Gln Gly Pro Ala Gly
            180                 185                 190

Ala Ala Ala Ala Ala Ala Ala Gly Pro Gly Gly Tyr Gly Gly
            195                 200                 205

Pro Gly Gln Gln Gly Pro Gly Gln Gly Gln Tyr Gly Pro Gly Ala Gly
    210                 215                 220

Gln Gln Gly Gln Gly Pro Gly Ser Gln Gln Gly Pro Ala Ser Ala Ala
225                 230                 235                 240

Ala Ala Ala Ala

<210> SEQ ID NO 30
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Ser Gly Ala Gly Gln Gly Thr Gly Ala Gly Ala Gly Ala Ala Ala
1               5                   10                  15

Ala Ala Ala Gly Ala Ala Gly Ser Gly Ala Gly Gln Gly Ala Gly Ser
            20                  25                  30

Gly Ala Gly Ala Ala Ala Ala Ala Ala Ala Ser Ala Ala Gly Ala
            35                  40                  45

Gly Gln Gly Ala Gly Ser Gly Ser Gly Ala Gly Ala Ala Ala Ala
    50                  55                  60

Ala Ala Ala Ala Gly Ala Gly Gln Gly Ala Gly Ser Gly Ser Gly Ala
65                  70                  75                  80

Gly Ala Ala Ala Ala Ala Ala Ala Ala Ala Ala Gln Gln Gln
                85                  90                  95

Gln Gln Gln Gln Ala Ala Ala Ala Ala Ala Ala Ala Ala Ala Ala Ala
            100                 105                 110

```
Ala Gly Ser Gly Gln Gly Ala Ser Phe Gly Val Thr Gln Gln Phe Gly
        115                 120                 125

Ala Pro Ser Gly Ala Ala Ser Ser Ala Ala Ala Ala Ala Ala Ala Ala
130                 135                 140

Ala Ala Ala Ala Ala Gly Ser Gly Ala Gly Gln Glu Ala Gly Thr Gly
145                 150                 155                 160

Ala Gly Ala Ala Ala Ala Ala Ala Gly Ala Ala Gly Ser Gly
        165                 170                 175

Ala Gly Gln Gly Ala Gly Ser Gly Ala Gly Ala Ala Ala Ala Ala Ala
        180                 185                 190

Ala Ala Ala Ser Ala Ala Gly Ala Gly Gln Gly Ala Gly Ser Gly Ser
        195                 200                 205

Gly Ala Gly Ala Ala Ala Ala Ala Ala Ala Ala Ala Ala Ala Ala Gln
        210                 215                 220

Gln Gln Gln Gln Gln Ala Ala Ala Ala Ala Ala Ala Ala Ala Ala Ala
225                 230                 235                 240

Ala Ala Ala

<210> SEQ ID NO 31
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Gly Ala Gln Lys Gln Pro Ser Gly Glu Ser Ser Val Ala Thr Ala
1               5                   10                  15

Ser Ala Ala Ala Thr Ser Val Thr Ser Ala Gly Ala Pro Val Gly Lys
            20                  25                  30

Pro Gly Val Pro Ala Pro Ile Phe Tyr Pro Gln Gly Pro Leu Gln Gln
        35                  40                  45

Gly Pro Ala Pro Gly Pro Ser Tyr Val Gln Pro Ala Thr Ser Gln Gln
    50                  55                  60

Gly Pro Ile Gly Gly Ala Gly Arg Ser Asn Ala Phe Ser Ser Ser Phe
65                  70                  75                  80

Ala Ser Ala Leu Ser Gly Asn Arg Gly Phe Ser Glu Val Ile Ser Ser
            85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
        115                 120                 125

Tyr Asn Ser Ile Gly Ser Gly Ala Asn Ala Phe Ala Tyr Ala Gln Ala
    130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
            165                 170                 175

Ser Gly Ala Ala Gly Gln Gly Gln Ser Ile Pro Tyr Gly Gly Gln Gln
            180                 185                 190

Gln Pro Pro Met Thr Ile Ser Ala Ala Ser Ser Ala Gly Ala Ser
        195                 200                 205

Ala Ala Ala Val Lys Gly Gly Gln Val Gly Gln Gly Pro Tyr Gly Gly
    210                 215                 220
```

Gln Gln Gln Ser Thr Ala Ala Ser Ala Ser Ala Ala Thr Thr Ala
225                 230                 235                 240

Thr Ala

<210> SEQ ID NO 32
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Ala Asp Gly Gly Ser Gly Leu Gly Gly Tyr Gly Ala Gly Arg Gly
1               5                   10                  15

Tyr Gly Ala Gly Leu Gly Gly Ala Asp Gly Ala Gly Ala Ala Ser Ala
            20                  25                  30

Ala Ala Ala Gly Gly Gln Gly Gly Arg Gly Gly Phe Gly Arg Leu
        35                  40                  45

Gly Ser Gln Gly Ala Gly Ala Gly Gln Gly Gly Ala Gly Ala Ala
    50                  55                  60

Ala Ala Val Ala Ala Ala Gly Gly Asp Gly Gly Ser Gly Leu Gly Gly
65                  70                  75                  80

Tyr Gly Ala Gly Arg Gly Tyr Gly Ala Gly Leu Gly Gly Ala Gly Gly
                85                  90                  95

Ala Gly Ala Ala Ser Ala Ala Ala Ala Gly Gly Gln Gly Gly Arg
            100                 105                 110

Gly Gly Phe Gly Gly Leu Gly Ser Gln Gly Ala Gly Ala Gly Gln
        115                 120                 125

Gly Gly Ala Gly Ala Ala Ser Gly Asp Gly Gly Ser Gly Leu Gly
    130                 135                 140

Gly Tyr Gly Ala Gly Arg Gly Tyr Gly Ala Gly Leu Gly Gly Ala Asp
145                 150                 155                 160

Gly Ala Gly Ala Ala Ser Ala Ala Ser Ala Ala Gly Gly Gln Gly Gly
                165                 170                 175

Arg Gly Gly Phe Gly Gly Leu Gly Ser Gln Gly Ala Gly Ala Gly
            180                 185                 190

Gln Gly Gly Ala Gly Ala Ala Ala Ala Ala Thr Ala Gly Gly Asp
        195                 200                 205

Gly Gly Ser Gly Leu Gly Gly Tyr Gly Ala Gly Arg Gly Tyr Gly Ala
    210                 215                 220

Gly Leu Gly Gly Ala Gly Gly Ala Gly Ala Ala Ser Ala Ala Ala Ala
225                 230                 235                 240

Ala

<210> SEQ ID NO 33
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Ala Gly Ala Gly Gln Gly Gly Arg Gly Gly Tyr Gly Gln Gly Gly
1               5                   10                  15

Phe Gly Gly Gln Gly Ser Gly Ala Gly Ala Gly Ala Ser Ala Ala Ala

```
                    20                  25                  30
Gly Ala Gly Ala Gly Gln Gly Gly Arg Gly Gly Tyr Gly Gln Gly Gly
            35                  40                  45
Phe Gly Gly Gln Gly Ser Gly Ala Gly Ala Gly Ala Ser Ala Ala Ala
        50                  55                  60
Gly Ala Gly Ala Gly Gln Gly Gly Arg Gly Gly Tyr Gly Gln Gly Gly
65                  70                  75                  80
Phe Gly Gly Gln Gly Ser Gly Ala Gly Ala Gly Ala Ser Ala Ala Ala
                85                  90                  95
Ala Ala Gly Ala Gly Gln Gly Gly Arg Gly Gly Tyr Gly Gln Gly Gly
            100                 105                 110
Leu Gly Gly Ser Gly Ser Gly Ala Gly Ala Gly Ala Gly Ala Ala Ala
        115                 120                 125
Ala Ala Ala Ala Gly Ala Gly Gly Tyr Gly Gln Gly Gly Leu Gly Gly
    130                 135                 140
Tyr Gly Gln Gly Ala Gly Ala Gly Gln Gly Gly Leu Gly Gly Tyr Gly
145                 150                 155                 160
Ser Gly Ala Gly Ala Gly Ala Ser Ala Ala Ala Ala Gly Ala Gly
                165                 170                 175
Gly Ala Gly Gln Gly Gly Leu Gly Gly Tyr Gly Gln Gly Gly Ala Gly
            180                 185                 190
Gly Gln Gly Gly Leu Gly Gly Tyr Gly Ser Gly Ala Gly Ala Gly Ala
        195                 200                 205
Ala Ala Ala Ala Ala Gly Ala Gly Gly Ser Gly Gln Gly Gly Leu
    210                 215                 220
Gly Gly Tyr Gly Ser Gly Gly Ala Gly Gly Ala Ser Ala Ala Ala
225                 230                 235                 240
Ala
```

<210> SEQ ID NO 34
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Gly Ala Tyr Ala Tyr Ala Tyr Ile Ala Asn Ala Phe Ala Ser Ile
1               5                   10                  15
Leu Ala Asn Thr Gly Leu Leu Ser Val Ser Ala Ala Ser Val Ala
            20                  25                  30
Ser Ser Val Ala Ser Ala Ile Ala Thr Ser Val Ser Ser Ser Ala
        35                  40                  45
Ala Ala Ala Ala Ser Ala Ser Ala Ala Ala Ala Ser Ala Gly Ala
    50                  55                  60
Ser Ala Ala Ser Ser Ala Ser Ala Ser Ser Ala Ser Ala Ala Ala
65                  70                  75                  80
Gly Ala Gly Ala Gly Ala Gly Ala Gly Ala Ser Gly Ala Ser Gly Ala
                85                  90                  95
Ala Gly Gly Ser Gly Gly Phe Gly Leu Ser Ser Gly Phe Gly Ala Gly
            100                 105                 110
Ile Gly Gly Leu Gly Gly Tyr Pro Ser Gly Ala Leu Gly Gly Leu Gly
        115                 120                 125
Ile Pro Ser Gly Leu Leu Ser Ser Gly Leu Leu Ser Pro Ala Ala Asn
```

```
            130                 135                 140
Gln Arg Ile Ala Ser Leu Ile Pro Leu Ile Leu Ser Ala Ile Ser Pro
145                 150                 155                 160

Asn Gly Val Asn Phe Gly Val Ile Gly Ser Asn Ile Ala Ser Leu Ala
                165                 170                 175

Ser Gln Ile Ser Gln Ser Gly Gly Gly Ile Ala Ala Ser Gln Ala Phe
                180                 185                 190

Thr Gln Ala Leu Leu Glu Leu Val Ala Ala Phe Ile Gln Val Leu Ser
            195                 200                 205

Ser Ala Gln Ile Gly Ala Val Ser Ser Ser Ala Ser Ala Gly Ala
            210                 215                 220

Thr Ala Asn Ala Phe Ala Gln Ser Leu Ser Ser Ala Phe Ala Gly
225                 230                 235

<210> SEQ ID NO 35
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Ala Ala Gln Lys Gln Pro Ser Gly Glu Ser Ser Val Ala Thr Ala
1               5                   10                  15

Ser Ala Ala Ala Thr Ser Val Thr Ser Gly Gly Ala Pro Val Gly Lys
                20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
        50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
                85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
            115                 120                 125

Tyr Asn Ser Ile Gly Ser Gly Ala Asn Ala Phe Ala Tyr Ala Gln Ala
        130                 135                 140

Phe Ala Arg Val Leu Tyr Pro Leu Val Arg Gln Tyr Gly Leu Ser Ser
145                 150                 155                 160

Ser Gly Lys Ala Ser Ala Phe Ala Ser Ala Ile Ala Ser Ser Phe Ser
                165                 170                 175

Ser Gly Thr Ser Gly Gln Gly Pro Ser Ile Gly Gln Gln Gln Pro Pro
            180                 185                 190

Val Thr Ile Ser Ala Ala Ser Ala Ser Ala Gly Ala Ser Ala Ala Ala
            195                 200                 205

Val Gly Gly Gly Gln Val Gly Gln Gly Pro Tyr Gly Gly Gln Gln Gln
        210                 215                 220

Ser Thr Ala Ala Ser Ala Ser Ala Ala Ala Thr Ala Thr Ser
225                 230                 235

<210> SEQ ID NO 36
<211> LENGTH: 239
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Ala Ala Gln Lys Gln Pro Ser Gly Glu Ser Ser Val Ala Thr Ala
1               5                   10                  15

Ser Ala Ala Ala Thr Ser Val Thr Ser Gly Gly Ala Pro Val Gly Lys
                20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
        50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
                85                  90                  95

Ala Ser Ala Thr Ala Val Ala Ser Ala Phe Gln Lys Gly Leu Ala Pro
                100                 105                 110

Tyr Gly Thr Ala Phe Ala Leu Ser Ala Ala Ser Ala Ala Ala Asp Ala
            115                 120                 125

Tyr Asn Ser Ile Gly Ser Gly Ala Asn Ala Phe Ala Tyr Ala Gln Ala
        130                 135                 140

Phe Ala Arg Val Leu Tyr Pro Leu Val Arg Gln Tyr Gly Leu Ser Ser
145                 150                 155                 160

Ser Gly Lys Ala Ser Ala Phe Ala Ser Ala Ile Ala Ser Ser Phe Ser
                165                 170                 175

Ser Gly Thr Ser Gly Gln Gly Pro Ser Ile Gly Gln Gln Gln Pro Pro
                180                 185                 190

Val Thr Ile Ser Ala Ala Ser Ala Ser Ala Gly Ala Ser Ala Ala Ala
            195                 200                 205

Val Gly Gly Gly Gln Val Gly Gln Gly Pro Tyr Gly Gly Gln Gln Gln
        210                 215                 220

Ser Thr Ala Ala Ser Ala Ser Ala Ala Ala Thr Ala Thr Ser
225                 230                 235

<210> SEQ ID NO 37
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Ala Ala Gln Lys Gln Pro Ser Gly Glu Ser Ser Val Ala Thr Ala
1               5                   10                  15

Ser Ala Ala Ala Thr Ser Val Thr Ser Gly Gly Ala Pro Val Gly Lys
                20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
        50                  55                  60

Gly Pro Ile Gly Gly Val Gly Gly Ser Asn Ala Phe Ser Ser Ser Phe
65                  70                  75                  80
```

Ala Ser Ala Leu Ser Leu Asn Arg Gly Phe Thr Glu Val Ile Ser Ser
                 85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
            115                 120                 125

Tyr Asn Ser Ile Gly Ser Gly Ala Asn Ala Phe Ala Tyr Ala Gln Ala
        130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
                165                 170                 175

Ser Gly Thr Ser Gly Gln Gly Pro Ser Ile Gly Gln Gln Gln Pro Pro
            180                 185                 190

Val Thr Ile Ser Ala Ala Ser Ala Ser Ala Gly Ala Ser Ala Ala Ala
            195                 200                 205

Val Gly Gly Gly Gln Val Gly Gln Gly Pro Tyr Gly Gly Gln Gln Gln
        210                 215                 220

Ser Thr Ala Ala Ser Ala Ser Ala Ala Ala Thr Ala Thr Ser
225                 230                 235

<210> SEQ ID NO 38
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Gly Ala Gln Lys Gln Pro Ser Gly Glu Ser Ser Val Ala Thr Ala
1               5                   10                  15

Ser Ala Ala Ala Thr Ser Val Thr Ser Ala Gly Ala Pro Val Gly Lys
                20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
        50                  55                  60

Gly Pro Ile Gly Gly Val Gly Gly Ser Asn Ala Phe Ser Ser Ser Phe
65                  70                  75                  80

Ala Ser Ala Leu Ser Leu Asn Arg Gly Phe Thr Glu Val Ile Ser Ser
                85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
            115                 120                 125

Tyr Asn Ser Ile Gly Ser Gly Ala Asn Ala Phe Ala Tyr Ala Gln Ala
        130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
                165                 170                 175

Ser Gly Thr Ser Gly Gln Gly Pro Ser Asn Gly Gln Gln Gln Pro Pro
            180                 185                 190

Val Thr Ile Ser Ala Ala Ser Ala Ser Ala Gly Ala Ser Ala Ala Ala
            195                 200                 205

```
Val Gly Gly Gly Gln Val Ser Gln Gly Pro Tyr Gly Gln Gln Gln
        210                 215                 220

Ser Thr Ala Ala Ser Ala Ser Ala Ala Ala Thr Ala Thr Ser
225                 230                 235
```

<210> SEQ ID NO 39
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Gly Gly Ala Gln Lys Gln Pro Ser Gly Glu Ser Ser Val Ala Thr Ala
1               5                   10                  15

Ser Ala Ala Ala Thr Ser Val Thr Ser Ala Gly Ala Pro Gly Gly Lys
                20                  25                  30

Pro Gly Val Pro Ala Pro Ile Phe Tyr Pro Gln Gly Pro Leu Gln Gln
            35                  40                  45

Gly Pro Ala Pro Gly Pro Ser Asn Val Gln Pro Gly Thr Ser Gln Gln
50                  55                  60

Gly Pro Ile Gly Gly Val Gly Ser Asn Ala Phe Ser Ser Ser Phe
65                  70                  75                  80

Ala Ser Ala Leu Ser Leu Asn Arg Gly Phe Thr Glu Val Ile Ser Ser
                85                  90                  95

Ala Ser Ala Thr Ala Val Ala Ser Ala Phe Gln Lys Gly Leu Ala Pro
            100                 105                 110

Tyr Gly Thr Ala Phe Ala Leu Ser Ala Ala Ser Ala Ala Ala Asp Ala
            115                 120                 125

Tyr Asn Ser Ile Gly Ser Gly Ala Asn Ala Phe Ala Tyr Ala Gln Ala
130                 135                 140

Phe Ala Arg Val Leu Tyr Pro Leu Val Gln Gln Tyr Gly Leu Ser Ser
145                 150                 155                 160

Ser Ala Lys Ala Ser Ala Phe Ala Ser Ala Ile Ala Ser Ser Phe Ser
                165                 170                 175

Ser Gly Thr Ser Gly Gln Gly Pro Ser Ile Gly Gln Gln Pro Pro
            180                 185                 190

Val Thr Ile Ser Ala Ala Ser Ala Ser Ala Gly Ala Ser Ala Ala Ala
            195                 200                 205

Val Gly Gly Gly Gln Val Gly Gln Gly Pro Tyr Gly Gln Gln Gln
        210                 215                 220

Ser Thr Ala Ala Ser Ala Ser Ala Ala Ala Thr Ala Thr Ser
225                 230                 235
```

<210> SEQ ID NO 40
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Gly Pro Gly Gly Tyr Gly Gly Pro Gly Gln Gln Gly Pro Gly Gln Gly
1               5                   10                  15

Gln Gln Gln Gly Pro Ala Ser Ala Ala Ala Ala Ala Ala Ala Ala Gly
                20                  25                  30
```

Pro Gly Gly Tyr Gly Gly Pro Gly Gln Gln Gly Pro Gly Gln Gly Gln
        35                  40                  45

Gln Gln Gly Pro Ala Ser Ala Ala Ala Ala Ala Ala Ala Ala Ala Gly
50                  55                  60

Pro Gly Gly Tyr Gly Gly Pro Gly Gln Gln Arg Pro Gly Gln Ala Gln
65                  70                  75                  80

Tyr Gly Arg Gly Thr Gly Gln Gln Gly Gln Pro Gly Ala Gln Gln
                85                  90                  95

Gly Pro Ala Ser Ala Ala Ala Ala Ala Ala Gly Ala Gly Leu Tyr
            100                 105                 110

Gly Gly Pro Gly Gln Gln Gly Pro Gly Gln Gly Gln Gln Gly Pro
            115                 120                 125

Ala Ser Ala Ala Ala Ala Ala Ala Ala Ala Ala Ala Gly Pro Gly
            130                 135                 140

Gly Tyr Gly Gly Pro Gly Gln Gln Gly Pro Gly Gln Ala Gln Gln
145                 150                 155                 160

Gly Pro Ala Ser Ala Ala Ala Ala Ala Ala Gly Pro Gly Gly Tyr
                165                 170                 175

Ser Gly Pro Gly Gln Gln Gly Pro Gly Gln Ala Gln Gln Gly Pro
            180                 185                 190

Ala Ser Ala Ala Ala Ala Ala Ala Ala Gly Pro Gly Gly Tyr
                195                 200                 205

Gly Gly Pro Gly Gln Gln Gly Pro Gly Gln Gly Gln Gln Gly Pro
            210                 215                 220

Ala Ser Ala Ala Ala Ala Ala Ala Thr Ala Ala
225                 230                 235

<210> SEQ ID NO 41
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Ala Gly Gly Asp Gly Gly Leu Phe Leu Ser Ser Gly Asp Phe Gly
1               5                   10                  15

Arg Gly Gly Ala Gly Ala Gly Ala Gly Ala Ala Ala Ser Ala Ala
                20                  25                  30

Ala Ala Ser Ser Ala Ala Ala Gly Ala Arg Gly Gly Ser Gly Phe Gly
            35                  40                  45

Val Gly Thr Gly Gly Phe Gly Arg Gly Ala Gly Asp Gly Ala Ser
50                  55                  60

Ala Ala Ala Ala Ser Ala Ala Ala Ser Ala Ala Ala Gly Ala
65                  70                  75                  80

Gly Gly Asp Ser Gly Leu Phe Leu Ser Ser Gly Asp Phe Gly Arg Gly
                85                  90                  95

Gly Ala Gly Ala Gly Ala Gly Ala Ala Ala Ser Ala Ala Ala Ala
            100                 105                 110

Ser Ala Ala Ala Gly Thr Gly Gly Val Gly Gly Leu Phe Leu Ser
            115                 120                 125

Ser Gly Asp Phe Gly Arg Gly Gly Ala Gly Ala Gly Ala Gly Ala Ala
            130                 135                 140

Ala Ala Ser Ala Ala Ala Ala Ser Ser Ala Ala Ala Gly Ala Arg Gly

```
                145                 150                 155                 160
Gly Ser Gly Phe Gly Val Gly Thr Gly Phe Gly Arg Gly Gly Pro
                    165                 170                 175
Gly Ala Gly Thr Gly Ala Ala Ala Ser Ala Ala Ala Ser Ala
                180                 185                 190
Ala Ala Ala Gly Ala Gly Gly Asp Ser Gly Leu Phe Leu Ser Ser Glu
                195                 200                 205
Asp Phe Gly Arg Gly Gly Ala Gly Ala Gly Thr Gly Ala Ala Ala
210                 215                 220
Ser Ala Ala Ala Ala Ser Ala Ala Ala Ala
225                 230

<210> SEQ ID NO 42
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Ala Gly Arg Gly Tyr Gly Gly Gly Tyr Gly Gly Gly Ala Ala Ala
1               5                   10                  15
Gly Ala Gly Ala Gly Ala Gly Ala Gly Arg Gly Tyr Gly Gly Gly Tyr
                20                  25                  30
Gly Gly Gly Ala Gly Ser Gly Ala Gly Ser Gly Ala Gly Ala Gly Gly
                35                  40                  45
Gly Ser Gly Tyr Gly Arg Gly Ala Gly Ala Gly Ala Gly Ala Gly Ala
        50                  55                  60
Ala Ala Ala Ala Gly Ala Gly Ala Gly Gly Ala Gly Gly Tyr Gly Gly
65                  70                  75                  80
Gly Ala Gly Ala Gly Ala Gly Ala Ser Ala Gly Ala Gly Ala Gly Ala
                85                  90                  95
Gly Ala Gly Gly Ala Gly Gly Tyr Gly Gly Tyr Gly Gly Gly Ala
                100                 105                 110
Gly Ala Gly Ala Gly Ala Gly Ala Ala Ala Ala Ala Gly Ala Gly Ala
                115                 120                 125
Gly Ala Gly Ala Gly Arg Gly Tyr Gly Gly Gly Phe Gly Gly Gly Ala
                130                 135                 140
Gly Ser Gly Ala Gly Ala Gly Ala Gly Ala Gly Gly Ser Gly Tyr
145                 150                 155                 160
Gly Arg Gly Ala Gly Gly Tyr Gly Gly Tyr Gly Gly Ala Gly
                165                 170                 175
Thr Gly Ala Gly Ala Ala Ala Thr Gly Ala Gly Ala Gly Ala Gly
                180                 185                 190
Ala Gly Arg Gly Tyr Gly Gly Gly Tyr Gly Gly Gly Ala Gly Ala Gly
                195                 200                 205
Ala Gly Ala Gly Ala Gly Ala Gly Gly Gly Ser Gly Tyr Gly Arg Gly
                210                 215                 220
Ala Gly Ala Gly Ala Ser Val Ala Ala
225                 230

<210> SEQ ID NO 43
<211> LENGTH: 231
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 43

Gly Ala Leu Gly Gln Gly Ala Ser Val Trp Ser Ser Pro Gln Met Ala
1               5                   10                  15

Glu Asn Phe Met Asn Gly Phe Ser Met Ala Leu Ser Gln Ala Gly Ala
            20                  25                  30

Phe Ser Gly Gln Glu Met Lys Asp Phe Asp Asp Val Arg Asp Ile Met
        35                  40                  45

Asn Ser Ala Met Asp Lys Met Ile Arg Ser Gly Lys Ser Gly Arg Gly
50                  55                  60

Ala Met Arg Ala Met Asn Ala Ala Phe Gly Ser Ala Ile Ala Glu Ile
65                  70                  75                  80

Val Ala Ala Asn Gly Gly Lys Glu Tyr Gln Ile Gly Ala Val Leu Asp
                85                  90                  95

Ala Val Thr Asn Thr Leu Leu Gln Leu Thr Gly Asn Ala Asp Asn Gly
            100                 105                 110

Phe Leu Asn Glu Ile Ser Arg Leu Ile Thr Leu Phe Ser Ser Val Glu
        115                 120                 125

Ala Asn Asp Val Ser Ala Ser Ala Gly Ala Asp Ala Ser Gly Ser Ser
130                 135                 140

Gly Pro Val Gly Gly Tyr Ser Ser Gly Ala Gly Ala Val Gly Gln
145                 150                 155                 160

Gly Thr Ala Gln Ala Val Gly Tyr Gly Gly Ala Gln Gly Val Ala
                165                 170                 175

Ser Ser Ala Ala Ala Gly Ala Thr Asn Tyr Ala Gln Gly Val Ser Thr
            180                 185                 190

Gly Ser Thr Gln Asn Val Ala Thr Ser Thr Val Thr Thr Thr Thr Asn
        195                 200                 205

Val Ala Gly Ser Thr Ala Thr Gly Tyr Asn Thr Gly Tyr Gly Ile Gly
210                 215                 220

Ala Ala Ala Gly Ala Ala Ala
225                 230

<210> SEQ ID NO 44
<211> LENGTH: 231
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Gly Gly Gln Gly Gly Gln Gly Gly Tyr Asp Gly Leu Gly Ser Gln Gly
1               5                   10                  15

Ala Gly Gln Gly Gly Tyr Gly Gln Gly Gly Ala Ala Ala Ala Ala
            20                  25                  30

Ala Ala Ser Gly Ala Gly Ser Ala Gln Arg Gly Gly Leu Gly Ala Gly
        35                  40                  45

Gly Ala Gly Gln Gly Tyr Gly Ala Gly Ser Gly Gln Gly Gly Ala
50                  55                  60

Gly Gln Gly Gly Ala Ala Ala Thr Ala Ala Ala Ala Gly Gln
65                  70                  75                  80

Gly Gly Gln Gly Gly Tyr Gly Gly Leu Gly Ser Gln Gly Ser Gly Gln
                85                  90                  95

```
Gly Gly Tyr Gly Gln Gly Ala Ala Ala Ala Ala Ala Ser
            100                 105                 110

Gly Asp Gly Gly Ala Gly Gln Glu Gly Leu Gly Ala Gly Gly Ala Gly
        115                 120                 125

Gln Gly Tyr Gly Ala Gly Leu Gly Gly Gln Gly Gly Ala Gly Gln Gly
        130                 135                 140

Gly Ala Ala Ala Ala Ala Ala Ala Gly Gly Gln Gly Gln
145                 150                 155                 160

Gly Gly Tyr Gly Gly Leu Gly Ser Gln Gly Ala Gly Gln Gly Tyr
            165                 170                 175

Gly Gln Gly Gly Ala Ala Ala Ala Ala Ala Ser Gly Ala Gly
        180                 185                 190

Gly Ala Gly Gln Gly Gly Leu Gly Ala Ala Gly Ala Gly Gln Gly Tyr
            195                 200                 205

Gly Ala Gly Ser Gly Gly Gln Gly Ala Gly Gln Gly Gly Ala Ala
        210                 215                 220

Ala Ala Ala Ala Ala Ala Ala
225                 230

<210> SEQ ID NO 45
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gly Gly Gln Gly Gly Gln Gly Gly Tyr Gly Gly Leu Gly Ser Gln Gly
1               5                   10                  15

Ala Gly Gln Gly Gly Tyr Gly Gln Gly Gly Val Ala Ala Ala Ala Ala
                20                  25                  30

Ala Ala Ser Gly Ala Gly Gly Ala Gly Arg Gly Gly Leu Gly Ala Gly
            35                  40                  45

Gly Ala Gly Gln Glu Tyr Gly Ala Val Ser Gly Gly Gln Gly Gly Ala
        50                  55                  60

Gly Gln Gly Gly Glu Ala Ala Ala Ala Ala Ala Ala Gly Gly Gln
65                  70                  75                  80

Gly Gly Gln Gly Gly Tyr Gly Gly Leu Gly Ser Gln Gly Ala Gly Gln
                85                  90                  95

Gly Gly Tyr Gly Gln Gly Gly Ala Ala Ala Ala Ala Ala Ala Ser
            100                 105                 110

Gly Ala Gly Gly Ala Arg Arg Gly Gly Leu Gly Ala Gly Gly Ala Gly
        115                 120                 125

Gln Gly Tyr Gly Ala Gly Leu Gly Gly Gln Gly Gly Ala Gly Gln Gly
        130                 135                 140

Ser Ala Ser Ala Ala Ala Ala Ala Ala Gly Gly Gln Gly Gly Gln
145                 150                 155                 160

Gly Gly Tyr Gly Gly Leu Gly Ser Gln Gly Ser Gly Gln Gly Tyr
            165                 170                 175

Gly Gln Gly Gly Ala Ala Ala Ala Ala Ala Ala Ser Gly Ala Gly
        180                 185                 190

Gly Ala Gly Arg Gly Ser Leu Gly Ala Gly Gly Ala Gly Gln Gly Tyr
            195                 200                 205

Gly Ala Gly Leu Gly Gly Gln Gly Gly Ala Gly Gln Gly Gly Ala Ala
        210                 215                 220
```

```
Ala Ala Ala Ser Ala Ala Ala
225                 230

<210> SEQ ID NO 46
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Pro Gly Gly Tyr Gly Gly Pro Gly Gln Gln Gly Pro Gly Gln Gly
1               5                   10                  15

Gln Tyr Gly Pro Gly Thr Gly Gln Gln Gly Gln Gly Pro Gly Gly Gln
                20                  25                  30

Gln Gly Pro Val Gly Ala Ala Ala Ala Ala Ala Ala Val Ser Ser
                35                  40                  45

Gly Gly Tyr Gly Ser Gln Gly Ala Gly Gln Gly Gln Gln Gly Ser
        50                  55                  60

Gly Gln Arg Gly Pro Ala Ala Ala Gly Pro Gly Gly Tyr Ser Gly Pro
65                  70                  75                  80

Gly Gln Gln Gly Pro Gly Gly Gly Gln Gln Gly Pro Ala Ser Ala
                85                  90                  95

Ala Ala Ala Ala Ala Ala Ala Gly Pro Gly Gly Tyr Gly Gly Ser
            100                 105                 110

Gly Gln Gln Gly Pro Gly Gln Gly Arg Gly Thr Gly Gln Gln Gly Gln
            115                 120                 125

Gly Pro Gly Gly Gln Gln Gly Pro Ala Ser Ala Ala Ala Ala Ala Ala
            130                 135                 140

Ala Gly Pro Gly Gly Tyr Gly Gly Pro Gly Gln Gln Gly Pro Gly Gln
145                 150                 155                 160

Gly Gln Tyr Gly Pro Gly Thr Gly Gln Gln Gly Gln Gly Pro Ala Ser
                165                 170                 175

Ala Ala Ala Ala Ala Ala Ala Gly Pro Gly Gly Tyr Gly Gly Pro Gly
            180                 185                 190

Gln Gln Gly Pro Gly Gln Gly Gln Tyr Gly Pro Gly Thr Gly Gln Gln
        195                 200                 205

Gly Gln Gly Pro Gly Gly Gln Gln Gly Pro Gly Gly Ala Ser Ala Ala
        210                 215                 220

Ala Ala Ala Ala Ala
225

<210> SEQ ID NO 47
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Gly Tyr Gly Pro Gly Ala Gly Gln Gln Gly Pro Gly Ser Gly Gly
1               5                   10                  15

Gln Gln Gly Pro Gly Gly Gln Gly Pro Tyr Gly Ser Gly Gln Gln Gly
                20                  25                  30

Pro Gly Gly Ala Gly Gln Gln Gly Pro Gly Gly Gln Gly Pro Tyr Gly
            35                  40                  45
```

```
Pro Gly Ala Ala Ala Ala Ala Ala Ala Gly Gly Tyr Gly Pro
    50                  55                  60

Gly Ala Gly Gln Gln Gly Pro Gly Ala Gly Gln Gln Gly Pro Gly
 65                  70                  75                  80

Ser Gln Gly Pro Gly Gly Gln Gly Pro Tyr Gly Pro Gly Ala Gly Gln
                 85                  90                  95

Gln Gly Pro Gly Ser Gln Gly Pro Gly Ser Gly Gly Gln Gln Gly Pro
            100                 105                 110

Gly Gly Gln Gly Pro Tyr Gly Pro Ser Ala Ala Ala Ala Ala Ala
            115                 120                 125

Ala Ala Gly Gly Tyr Gly Pro Gly Ala Gly Gln Arg Ser Gln Gly Pro
130                 135                 140

Gly Gly Gln Gly Pro Tyr Gly Pro Gly Ala Gly Gln Gln Gly Pro Gly
145                 150                 155                 160

Ser Gln Gly Pro Gly Ser Gly Gly Gln Gln Gly Pro Gly Gly Gln Gly
                165                 170                 175

Pro Tyr Gly Pro Ser Ala Ala Ala Ala Ala Ala Ala Gly Pro Gly
            180                 185                 190

Ala Gly Arg Gln Gly Pro Gly Ser Gln Gly Pro Gly Ser Gly Gly Gln
            195                 200                 205

Gln Gly Pro Gly Gly Gln Gly Pro Tyr Gly Pro Ser Ala Ala Ala Ala
            210                 215                 220

Ala Ala Ala Ala
225

<210> SEQ ID NO 48
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Gln Gly Gly Gln Gly Gly Gln Gly Gly Leu Gly Gln Gly Gly Tyr
 1               5                  10                  15

Gly Gln Gly Ala Gly Ser Ser Ala Ala Ala Ala Ala Ala Ala Ala
                 20                  25                  30

Ala Ala Ala Ala Ala Gly Arg Gly Gln Gly Tyr Gly Gln Gly Ser
             35                  40                  45

Gly Gly Asn Ala Ala Ala Ala Ala Ala Ala Ala Ala Ala Ala Ser
    50                  55                  60

Gly Gln Gly Ser Gln Gly Gly Gln Gly Gly Gln Gly Gly Tyr
 65                  70                  75                  80

Gly Gln Gly Ala Gly Ser Ser Ala Ala Ala Ala Ala Ala Ala Ala
                 85                  90                  95

Ala Ala Ala Ala Ser Gly Arg Gly Gln Gly Gly Tyr Gly Gln Gly Ala
            100                 105                 110

Gly Gly Asn Ala Ala Ala Ala Ala Ala Ala Ala Ala Ala Ala Ala
            115                 120                 125

Ala Gly Gln Gly Gly Gln Gly Gly Tyr Gly Gly Leu Gly Gln Gly Gly
            130                 135                 140

Tyr Gly Gln Gly Ala Gly Ser Ser Ala Ala Ala Ala Ala Ala Ala
145                 150                 155                 160

Ala Ala Ala Ala Gly Gly Gln Gly Gly Gln Gly Gln Gly Gly Tyr Gly
```

```
              165                 170                 175
Gln Gly Ser Gly Gly Ser Ala Ala Ala Ala Ala Ala Ala Ala
            180                 185                 190

Ala Ala Ala Ala Ala Gly Arg Gly Gln Gly Tyr Gly Gln Gly Ser
        195                 200                 205

Gly Gly Asn Ala Ala Ala Ala Ala Ala Ala Ala Ala Ala Ala
        210                 215                 220

Ala
225

<210> SEQ ID NO 49
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Arg Gly Pro Gly Gly Tyr Gly Pro Gly Gln Gln Gly Pro Gly Gly
1               5                   10                  15

Pro Gly Ala Ala Ala Ala Ala Gly Pro Gly Gly Tyr Gly Pro Gly
            20                  25                  30

Gly Tyr Gly Pro Gly Gln Gln Gly Pro Gly Pro Gly Ala Ala Ala
        35                  40                  45

Ala Ala Ala Ala Gly Arg Gly Pro Gly Gly Tyr Gly Pro Gly Gln Gln
50                  55                  60

Gly Pro Gly Gln Gln Gly Pro Gly Gly Ser Gly Ala Ala Ala Ala
65                  70                  75                  80

Ala Gly Arg Gly Pro Gly Gly Tyr Gly Pro Gly Gln Gln Gly Pro Gly
                85                  90                  95

Gly Pro Gly Ala Ala Ala Ala Ala Ala Gly Pro Gly Gly Tyr Gly Pro
            100                 105                 110

Gly Gln Gln Gly Pro Gly Ala Ala Ala Ala Ala Ala Ala Gly Arg
        115                 120                 125

Gly Pro Gly Gly Tyr Gly Pro Gly Gln Gln Gly Pro Gly Pro Gly
    130                 135                 140

Ala Ala Ala Ala Ala Ala Ala Gly Arg Gly Pro Gly Gly Tyr Gly Pro
145                 150                 155                 160

Gly Gln Gln Gly Pro Gly Gln Gly Pro Gly Gly Ser Gly Ala Ala
                165                 170                 175

Ala Ala Ala Ala Gly Arg Gly Pro Gly Gly Tyr Gly Pro Gly Gln Gln
            180                 185                 190

Gly Pro Gly Gly Pro Gly Ala Ala Ala Ala Ala Gly Pro Gly Gly
        195                 200                 205

Tyr Gly Pro Gly Gln Gln Gly Pro Gly Ala Ala Ala Ala Ala Ala
    210                 215                 220

Ala
225

<210> SEQ ID NO 50
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 50

Gly Arg Gly Pro Gly Tyr Gly Pro Gly Gln Gln Gly Pro Gly Gly
1               5                   10                  15

Ser Gly Ala Ala Ala Ala Ala Gly Arg Gly Pro Gly Gly Tyr Gly
                20                  25                  30

Pro Gly Gln Gln Gly Pro Gly Pro Gly Ala Ala Ala Ala Ala Ala
                35                  40                  45

Gly Pro Gly Gly Tyr Gly Pro Gly Gln Gln Gly Thr Gly Ala Ala
                50                  55                  60

Ala Ala Ala Ala Gly Ser Gly Ala Gly Tyr Gly Pro Gly Gln Gln
65                  70                  75                  80

Gly Pro Gly Gly Pro Gly Ala Ala Ala Ala Ala Gly Pro Gly Gly
                    85                  90                  95

Tyr Gly Pro Gly Gln Gln Gly Pro Gly Ala Ala Ala Ala Ala Ala
                100                 105                 110

Gly Ser Gly Pro Gly Gly Tyr Gly Pro Gly Gln Gln Gly Pro Gly Gly
                    115                 120                 125

Ser Ser Ala Ala Ala Ala Ala Gly Pro Gly Arg Tyr Gly Pro Gly
    130                 135                 140

Gln Gln Gly Pro Gly Ala Ala Ala Ala Ser Ala Gly Arg Gly Pro
145                 150                 155                 160

Gly Gly Tyr Gly Pro Gly Gln Gln Gly Pro Gly Pro Gly Ala Ala
                    165                 170                 175

Ala Ala Ala Ala Gly Pro Gly Gly Tyr Gly Pro Gly Gln Gln Gly Pro
                    180                 185                 190

Gly Ala Ala Ala Ala Ala Ala Gly Ser Gly Pro Gly Gly Tyr Gly
                    195                 200                 205

Pro Gly Gln Gln Gly Pro Gly Pro Gly Ala Ala Ala Ala Ala Ala
        210                 215                 220

Ala
225

<210> SEQ ID NO 51
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Ala Ala Ala Thr Ala Gly Ala Gly Ser Val Ala Gly Gly Tyr
1               5                   10                  15

Gly Gly Gly Ala Gly Ala Ala Gly Ala Gly Ala Gly Gly Tyr Gly
                20                  25                  30

Gly Gly Tyr Gly Ala Val Ala Gly Ser Gly Ala Gly Ala Ala Ala
                35                  40                  45

Ala Ser Ser Gly Ala Gly Gly Ala Ala Gly Tyr Gly Arg Gly Tyr Gly
    50                  55                  60

Ala Gly Ser Gly Ala Gly Ala Gly Thr Val Ala Ala Tyr Gly
65                  70                  75                  80

Gly Ala Gly Gly Val Ala Thr Ser Ser Ser Ala Thr Ala Ser Gly
                    85                  90                  95

Ser Arg Ile Val Thr Ser Gly Gly Tyr Gly Tyr Gly Thr Ser Ala Ala
                100                 105                 110

```
Ala Gly Ala Gly Val Ala Ala Gly Ser Tyr Ala Gly Val Asn Arg
            115                 120                 125

Leu Ser Ser Ala Glu Ala Ala Ser Arg Val Ser Asn Ile Ala Ala
    130                 135                 140

Ile Ala Ser Gly Gly Ala Ser Ala Leu Pro Ser Val Ile Ser Asn Ile
145                 150                 155                 160

Tyr Ser Gly Val Val Ala Ser Gly Val Ser Ser Asn Glu Ala Leu Ile
                165                 170                 175

Gln Ala Leu Leu Glu Leu Leu Ser Ala Leu Val His Val Leu Ser Ser
            180                 185                 190

Ala Ser Ile Gly Asn Val Ser Ser Val Gly Val Asp Ser Thr Leu Asn
            195                 200                 205

Val Val Gln Asp Ser Val Gly Gln Tyr Val Gly
    210                 215

<210> SEQ ID NO 52
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Gly Gln Gly Gly Phe Ser Gly Gln Gly Gln Gly Gly Phe Gly Pro
1               5                   10                  15

Gly Ala Gly Ser Ser Ala Ala Ala Ala Ala Ala Ala Ala Ala Ala Ala
                20                  25                  30

Arg Gln Gly Gln Gly Gln Gly Gln Gly Phe Gly Gln Gly Ala Gly Gly
            35                  40                  45

Asn Ala Ala Ala Ala Ala Ala Ala Ala Ala Ala Ala Ala Ala Ala Gln
        50                  55                  60

Gln Gly Gln Gly Gly Phe Ser Gly Arg Gly Gln Gly Gly Phe Gly
65                  70                  75                  80

Pro Gly Ala Gly Ser Ser Ala Ala Ala Ala Ala Gly Gln Gly Gly
            85                  90                  95

Gln Gly Gln Gly Gly Phe Gly Gln Gly Ala Gly Gly Asn Ala Ala Ala
            100                 105                 110

Ala Ala Ala Ala Ala Ala Ala Ala Ala Ala Ala Gly Gln Gly Gly
            115                 120                 125

Gln Gly Arg Gly Gly Phe Gly Gln Gly Ala Gly Gly Asn Ala Ala Ala
        130                 135                 140

Ala Ala Ala Ala Ala Ala Ala Ala Ala Ala Gln Gln Gly Gly
145                 150                 155                 160

Gln Gly Gly Phe Gly Gly Arg Gly Gln Gly Gly Phe Gly Pro Gly Ala
                165                 170                 175

Gly Ser Ser Ala Ala Ala Ala Ala Ala Gly Gln Gly Gly Gln Gly Arg
            180                 185                 190

Gly Gly Phe Gly Gln Gly Ala Gly Gly Asn Ala Ala Ala Ala Ser Ala
        195                 200                 205

Ala Ala Ala Ala Ser Ala Ala Ala Ala Gly Gln
    210                 215

<210> SEQ ID NO 53
<211> LENGTH: 218
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 53

Gly Gly Tyr Gly Pro Gly Ala Gly Gln Gln Gly Pro Gly Gly Ala Gly
1               5                   10                  15

Gln Gln Gly Pro Gly Ser Gln Gly Pro Gly Gly Ala Gly Gln Gln Gly
            20                  25                  30

Pro Gly Gly Gln Gly Pro Tyr Gly Pro Gly Ala Ala Ala Ala Ala Ala
        35                  40                  45

Ala Val Gly Gly Tyr Gly Pro Gly Ala Gly Gln Gln Gly Pro Gly Ser
    50                  55                  60

Gln Gly Pro Gly Ser Gly Gln Gln Gly Pro Gly Gly Gln Gly Pro
65                  70                  75                  80

Tyr Gly Pro Ser Ala Ala Ala Ala Ala Ala Ala Gly Gly Tyr Gly
                85                  90                  95

Pro Gly Ala Gly Gln Gln Gly Pro Gly Ser Gln Gly Pro Gly Ser Gly
                100                 105                 110

Gly Gln Gln Gly Pro Gly Gly Leu Gly Pro Tyr Gly Pro Ser Ala Ala
            115                 120                 125

Ala Ala Ala Ala Ala Gly Gly Tyr Gly Pro Gly Ala Gly Gln Gln
            130                 135                 140

Gly Pro Gly Ser Gln Gly Pro Gly Ser Gly Gly Gln Gln Arg Pro Gly
145                 150                 155                 160

Gly Leu Gly Pro Tyr Gly Pro Ser Ala Ala Ala Ala Ala Ala Ala
            165                 170                 175

Gly Gly Tyr Gly Pro Gly Ala Gly Gln Gln Gly Pro Gly Ser Gln Gly
            180                 185                 190

Pro Gly Ser Gly Gly Gln Gln Arg Pro Gly Gly Leu Gly Pro Tyr Gly
        195                 200                 205

Pro Ser Ala Ala Ala Ala Ala Ala Ala
        210                 215

<210> SEQ ID NO 54
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Ala Gly Ala Gly Gly Gly Tyr Gly Gly Tyr Ser Ala Gly Gly
1               5                   10                  15

Gly Ala Gly Ala Gly Ser Gly Ala Ala Ala Gly Ala Gly Ala Gly Arg
            20                  25                  30

Gly Gly Ala Gly Gly Tyr Ser Ala Gly Ala Gly Thr Gly Ala Gly Ala
        35                  40                  45

Ala Ala Gly Ala Gly Thr Ala Gly Gly Tyr Ser Gly Gly Tyr Gly Ala
    50                  55                  60

Gly Ala Ser Ser Ala Gly Ser Ser Phe Ile Ser Ser Ser Met
65                  70                  75                  80

Ser Ser Ser Gln Ala Thr Gly Tyr Ser Ser Ser Gly Tyr Gly Gly
                85                  90                  95

Gly Ala Ala Ser Ala Ala Ala Gly Ala Gly Ala Ala Ala Gly Gly Tyr
                100                 105                 110
```

-continued

```
Gly Gly Gly Tyr Gly Ala Gly Ala Gly Ala Ala Ala Ser
            115                 120                 125

Gly Ala Thr Gly Arg Val Ala Asn Ser Leu Gly Ala Met Ala Ser Gly
            130                 135                 140

Gly Ile Asn Ala Leu Pro Gly Val Phe Ser Asn Ile Phe Ser Gln Val
145                 150                 155                 160

Ser Ala Ala Ser Gly Gly Ala Ser Gly Gly Ala Val Leu Val Gln Ala
                165                 170                 175

Leu Thr Glu Val Ile Ala Leu Leu Leu His Ile Leu Ser Ser Ala Ser
            180                 185                 190

Ile Gly Asn Val Ser Ser Gln Gly Leu Glu Gly Ser Met Ala Ile Ala
            195                 200                 205

Gln Gln Ala Ile Gly Ala Tyr Ala Gly
            210                 215

<210> SEQ ID NO 55
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Ala Gly Ala Gly Gly Ala Gly Gly Tyr Ala Gln Gly Tyr Gly Ala
1               5                   10                  15

Gly Ala Gly Ala Gly Ala Gly Ala Gly Thr Gly Ala Gly Gly Ala Gly
            20                  25                  30

Gly Tyr Gly Gln Gly Tyr Gly Ala Gly Ser Gly Ala Gly Ala Gly Gly
            35                  40                  45

Ala Gly Gly Tyr Gly Ala Gly Ala Gly Ala Gly Ala Gly Ala Gly Asp
        50                  55                  60

Ala Ser Gly Tyr Gly Gln Gly Tyr Gly Asp Gly Ala Gly Ala Gly Ala
65                  70                  75                  80

Gly Ala Ala Ala Ala Ala Gly Ala Ala Ala Gly Ala Arg Gly Ala Gly
                85                  90                  95

Gly Tyr Gly Gly Gly Ala Gly Ala Gly Ala Gly Ala Gly Ala Gly Ala
            100                 105                 110

Ala Gly Gly Tyr Gly Gln Gly Tyr Gly Ala Gly Ala Gly Glu Gly Ala
            115                 120                 125

Gly Ala Gly Ala Gly Ala Gly Ala Val Ala Gly Ala Gly Ala Ala Ala
            130                 135                 140

Ala Ala Gly Ala Gly Ala Gly Ala Gly Gly Ala Glu Gly Tyr Gly Ala
145                 150                 155                 160

Gly Ala Gly Ala Gly Gly Ala Gly Tyr Gly Gln Ser Tyr Gly Asp
                165                 170                 175

Gly Ala Ala Ala Ala Gly Ser Gly Ala Gly Ala Gly Gly Ser Gly
            180                 185                 190

Gly Tyr Gly Ala Gly Ala Gly Ala Gly Ser Gly Ala Gly Ala Ala Gly
            195                 200                 205

Gly Tyr Gly Gly Gly Ala Gly Ala
            210                 215

<210> SEQ ID NO 56
<211> LENGTH: 216
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 56

Gly Pro Gly Gly Tyr Gly Pro Gly Gln Gln Gly Pro Gly Gly Tyr Gly
1               5                   10                  15

Pro Gly Gln Gln Gly Pro Gly Arg Tyr Gly Pro Gly Gln Gln Gly Pro
            20                  25                  30

Ser Gly Pro Gly Ser Ala Ala Ala Ala Ala Gly Ser Gly Gln Gln
        35                  40                  45

Gly Pro Gly Gly Tyr Gly Pro Arg Gln Gln Gly Pro Gly Gly Tyr Gly
    50                  55                  60

Gln Gly Gln Gln Gly Pro Ser Gly Pro Gly Ser Ala Ala Ala Ala Ser
65                  70                  75                  80

Ala Ala Ala Ser Ala Glu Ser Gly Gln Gln Gly Pro Gly Gly Tyr Gly
                85                  90                  95

Pro Gly Gln Gln Gly Pro Gly Gly Tyr Gly Pro Gly Gln Gln Gly Pro
            100                 105                 110

Gly Gly Tyr Gly Pro Gly Gln Gln Gly Pro Ser Gly Pro Gly Ser Ala
        115                 120                 125

Ala Ala Ala Ala Ala Ala Ser Gly Pro Gly Gln Gln Gly Pro Gly
    130                 135                 140

Gly Tyr Gly Pro Gly Gln Gln Gly Pro Gly Gly Tyr Gly Pro Gly Gln
145                 150                 155                 160

Gln Gly Pro Ser Gly Pro Gly Ser Ala Ala Ala Ala Ala Ala Ala
            165                 170                 175

Ser Gly Pro Gly Gln Gln Gly Pro Gly Gly Tyr Gly Pro Gly Gln Gln
        180                 185                 190

Gly Pro Gly Gly Tyr Gly Pro Gly Gln Gln Gly Leu Ser Gly Pro Gly
    195                 200                 205

Ser Ala Ala Ala Ala Ala Ala Ala
    210                 215

<210> SEQ ID NO 57
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Gly Arg Gly Pro Gly Gly Tyr Gly Gln Gly Gln Gln Gly Pro Gly Gly
1               5                   10                  15

Pro Gly Ala Ala Ala Ala Ala Ala Gly Pro Gly Gly Tyr Gly Pro Gly
            20                  25                  30

Gln Gln Gly Pro Gly Ala Ala Ala Ala Ala Ala Gly Ser Gly Pro
        35                  40                  45

Gly Gly Tyr Gly Pro Gly Gln Gln Gly Pro Gly Arg Ser Gly Ala Ala
    50                  55                  60

Ala Ala Ala Ala Gly Arg Gly Pro Gly Gly Tyr Gly Pro Gly
65                  70                  75                  80

Gln Gln Gly Pro Gly Gly Pro Gly Ala Ala Ala Ala Ala Gly Pro
            85                  90                  95

Gly Gly Tyr Gly Pro Gly Gln Gln Gly Pro Gly Ala Ala Ala Ala Ala

```
                    100                 105                 110
Ser Ala Gly Arg Gly Pro Gly Gly Tyr Gly Pro Gly Gln Gln Gly Pro
                115                 120                 125
Gly Gly Ser Gly Ala Ala Ala Ala Ala Gly Arg Gly Pro Gly Gly
            130                 135                 140
Tyr Gly Pro Gly Gln Gln Gly Pro Gly Gly Pro Gly Ala Ala Ala Ala
145                 150                 155                 160
Ala Ala Ala Gly Arg Gly Pro Gly Gly Tyr Gly Pro Gly Gln Gln Gly
                165                 170                 175
Pro Gly Gln Gln Gly Pro Gly Ser Gly Ala Ala Ala Ala Ala
            180                 185                 190
Gly Arg Gly Pro Gly Gly Tyr Gly Pro Gly Gln Gln Gly Pro Gly Gly
                195                 200                 205
Pro Gly Ala Ala Ala Ala Ala Ala
            210                 215

<210> SEQ ID NO 58
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Val Gly Ala Gly Gly Glu Gly Gly Tyr Asp Gln Gly Tyr Gly Ala
1               5                   10                  15
Gly Ala Gly Ala Gly Ser Gly Gly Ala Gly Gly Ala Gly Gly Tyr
                20                  25                  30
Gly Gly Gly Ala Gly Ala Gly Ser Gly Gly Ala Gly Gly Ala Gly
            35                  40                  45
Gly Tyr Gly Gly Gly Ala Gly Ala Gly Ala Gly Ala Gly Gly
        50                  55                  60
Ala Gly Gly Tyr Gly Gly Gly Ala Gly Ala Gly Thr Gly Ala Arg Ala
65                  70                  75                  80
Gly Ala Gly Gly Val Gly Gly Tyr Gly Gln Ser Tyr Gly Ala Gly Ala
                85                  90                  95
Ser Ala Ala Gly Ala Gly Val Gly Ala Gly Ala Gly Ala Gly
            100                 105                 110
Gly Ala Gly Gly Tyr Gly Gln Gly Tyr Gly Ala Gly Ala Gly Ile Gly
        115                 120                 125
Ala Gly Asp Ala Gly Tyr Gly Gly Gly Ala Gly Ala Ser
    130                 135                 140
Ala Gly Ala Gly Gly Tyr Gly Gly Gly Ala Gly Ala Gly Ala Gly Gly
145                 150                 155                 160
Val Gly Gly Tyr Gly Lys Gly Tyr Gly Ala Gly Ser Gly Ala Gly Ala
                165                 170                 175
Ala Ala Ala Ala Gly Ala Gly Ala Ser Ala Gly Gly Tyr Gly Arg
            180                 185                 190
Gly Asp Gly Ala Gly Ala Gly Ala Ser Gly Tyr Gly Gln Gly Tyr
        195                 200                 205
Gly Ala Gly Ala Ala Ala
    210

<210> SEQ ID NO 59
<211> LENGTH: 212
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Tyr Gly Ala Gly Ala Gly Arg Gly Tyr Gly Ala Gly Ala Gly Ala
1               5                   10                  15

Gly Ala Gly Ala Val Ala Ala Ser Gly Ala Gly Ala Gly Ala Gly Tyr
                20                  25                  30

Gly Ala Gly Ala Gly Ala Gly Ala Gly Ala Tyr Gly Ala Gly Ala
            35                  40                  45

Gly Arg Gly Tyr Gly Ala Gly Ala Gly Ala Gly Ala Gly Ser Gly Ala
        50                  55                  60

Ala Ser Gly Ala Gly Ala Gly Ala Gly Tyr Gly Ala Gly Ala Gly Ala
65                  70                  75                  80

Gly Ala Gly Tyr Gly Ala Gly Ala Gly Ser Gly Tyr Gly Thr Gly Ala
                85                  90                  95

Gly Ala Gly Ala Gly Ala Ala Ala Gly Gly Ala Gly Ala Gly Ala
            100                 105                 110

Gly Tyr Gly Ala Gly Ala Gly Arg Gly Tyr Gly Ala Gly Ala Gly Ala
        115                 120                 125

Gly Ala Ala Ser Gly Ala Gly Ala Gly Ala Gly Ala Gly Ala Ala Ser
    130                 135                 140

Gly Ala Gly Ala Gly Ser Gly Tyr Gly Ala Gly Ala Ala Ala Ala Gly
145                 150                 155                 160

Gly Ala Gly Ala Gly Ala Gly Gly Tyr Gly Ala Gly Ala Gly Arg
                165                 170                 175

Gly Tyr Gly Ala Gly Ala Gly Ala Gly Ala Gly Ala Gly Ser Gly Ser
            180                 185                 190

Gly Ser Ala Ala Gly Tyr Gly Gln Gly Tyr Gly Ser Gly Ser Gly Ala
        195                 200                 205

Gly Ala Ala Ala
    210

<210> SEQ ID NO 60
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gly Gln Gly Thr Asp Ser Ser Ala Ser Ser Val Ser Thr Ser Thr Ser
1               5                   10                  15

Val Ser Ser Ser Ala Thr Gly Pro Asp Thr Gly Tyr Pro Val Gly Tyr
                20                  25                  30

Tyr Gly Ala Gly Gln Ala Glu Ala Ala Ala Ser Ala Ala Ala Ala Ala
            35                  40                  45

Ala Ala Ser Ala Ala Glu Ala Ala Thr Ile Ala Gly Leu Gly Tyr Gly
50                  55                  60

Arg Gln Gly Gln Gly Thr Asp Ser Ser Ala Ser Ser Val Ser Thr Ser
65                  70                  75                  80

Thr Ser Val Ser Ser Ser Ala Thr Gly Pro Asp Met Gly Tyr Pro Val
                85                  90                  95
```

```
Gly Asn Tyr Gly Ala Gly Gln Ala Glu Ala Ala Ser Ala Ala Ala
                100                 105                 110

Ala Ala Ala Ala Ser Ala Ala Glu Ala Thr Ile Ala Ser Leu Gly
            115                 120                 125

Tyr Gly Arg Gln Gly Gln Gly Thr Asp Ser Ser Ala Ser Val Ser
    130                 135                 140

Thr Ser Thr Ser Val Ser Ser Ala Thr Gly Pro Gly Ser Arg Tyr
145                 150                 155                 160

Pro Val Arg Asp Tyr Gly Ala Asp Gln Ala Glu Ala Ala Ser Ala
                165                 170                 175

Ala Ala Ala Ala Ala Ala Ala Ser Ala Ala Glu Glu Ile Ala Ser
            180                 185                 190

Leu Gly Tyr Gly Arg Gln
        195

<210> SEQ ID NO 61
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Gln Gly Thr Asp Ser Val Ala Ser Ser Ala Ser Ser Ala Ser
1               5                   10                  15

Ala Ser Ser Ala Thr Gly Pro Asp Thr Gly Tyr Pro Val Gly Tyr
            20                  25                  30

Tyr Gly Ala Gly Gln Ala Glu Ala Ala Ser Ala Ala Ala Ala Ala
        35                  40                  45

Ala Ala Ser Ala Ala Glu Ala Thr Ile Ala Gly Leu Gly Tyr Gly
        50                  55                  60

Arg Gln Gly Gln Gly Thr Asp Ser Ser Ala Ser Ser Val Ser Thr Ser
65                  70                  75                  80

Thr Ser Val Ser Ser Ala Thr Gly Pro Gly Ser Arg Tyr Pro Val
                85                  90                  95

Arg Asp Tyr Gly Ala Asp Gln Ala Glu Ala Ala Ser Ala Thr Ala
                100                 105                 110

Ala Ala Ala Ala Ala Ala Ser Ala Ala Glu Glu Ile Ala Ser Leu Gly
            115                 120                 125

Tyr Gly Arg Gln Gly Gln Gly Thr Asp Ser Val Ala Ser Ser Ala Ser
    130                 135                 140

Ser Ser Ala Ser Ala Ser Ser Ala Thr Gly Pro Asp Thr Gly Tyr
145                 150                 155                 160

Pro Val Gly Tyr Tyr Gly Ala Gly Gln Ala Glu Ala Ala Ala Ser Ala
                165                 170                 175

Ala Ala Ala Ala Ala Ser Ala Ala Glu Ala Ala Thr Ile Ala Gly
            180                 185                 190

Leu Gly Tyr Gly Arg Gln
        195

<210> SEQ ID NO 62
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 62

```
Gly Gln Gly Gly Gln Gly Gly Tyr Gly Gly Leu Gly Gln Gly Gly Tyr
1               5                   10                  15
Gly Gln Gly Ala Gly Ser Ser Ala Ala Ala Ala Ala Ala Ala Ala Ala
            20                  25                  30
Ala Ala Ala Ala Gly Gly Gln Gly Gly Gln Gly Gln Gly Arg Tyr Gly
        35                  40                  45
Gln Gly Ala Gly Ser Ser Ala Ala Ala Ala Ala Ala Ala Ala Ala Ala
    50                  55                  60
Ala Ala Ala Ala Gly Arg Gly Gln Gly Gly Tyr Gly Gln Gly Ser Gly
65                  70                  75                  80
Gly Asn Ala Ala Ala Ala Ala Ala Ala Ala Ala Ala Ala Ala Ser Gly
                85                  90                  95
Gln Gly Ser Gln Gly Gly Gln Gly Gly Gln Gly Gln Gly Gly Tyr Gly
                100                 105                 110
Gln Gly Ala Gly Ser Ser Ala Ala Ala Ala Ala Ala Ala Ala Ala Ala
            115                 120                 125
Ala Ala Ala Ser Gly Arg Gly Gln Gly Gly Tyr Gly Gln Gly Ala Gly
        130                 135                 140
Gly Asn Ala Ala Ala Ala Ala Ala Ala Ala Ala Ala Ala Ala Ala Ala
145                 150                 155                 160
Gly Gln Gly Gly Gln Gly Gly Tyr Gly Gly Leu Gly Gln Gly Gly Tyr
                165                 170                 175
Gly Gln Gly Ala Gly Ser Ser Ala Ala Ala Ala Ala Ala Ala Ala Ala
            180                 185                 190
Ala Ala Ala
        195
```

<210> SEQ ID NO 63
<211> LENGTH: 193
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

```
Gly Gly Leu Gly Gly Gln Gly Gly Leu Gly Gly Leu Gly Ser Gln Gly
1               5                   10                  15
Ala Gly Leu Gly Gly Tyr Gly Gln Gly Gly Ala Gly Gln Gly Gly Ala
            20                  25                  30
Ala Ala Ala Ala Ala Ala Ala Gly Gly Leu Gly Gly Gln Gly Gly Arg
        35                  40                  45
Gly Gly Leu Gly Ser Gln Gly Ala Gly Gln Gly Gly Tyr Gly Gln Gly
    50                  55                  60
Gly Ala Gly Gln Gly Gly Ala Ala Ala Ala Ala Ala Ala Ala Gly Gly
65                  70                  75                  80
Leu Gly Gly Gln Gly Gly Leu Gly Ala Leu Gly Ser Gln Gly Ala Gly
                85                  90                  95
Gln Gly Gly Ala Gly Gln Gly Gly Tyr Gly Gln Gly Gly Ala Ala Ala
                100                 105                 110
Ala Ala Ala Gly Gly Leu Gly Gly Gln Gly Gly Leu Gly Gly Leu Gly
            115                 120                 125
Ser Gln Gly Ala Gly Gln Gly Gly Tyr Gly Gln Gly Gly Ala Gly Gln
        130                 135                 140
```

Gly Gly Ala Ala Ala Ala Ala Ala Gly Gly Leu Gly Gly Gln
145                 150                 155                 160

Gly Gly Leu Gly Gly Leu Gly Ser Gln Gly Ala Gly Pro Gly Tyr
                165                 170                 175

Gly Gln Gly Gly Ala Gly Gln Gly Gly Ala Ala Ala Ala Ala Ala
            180                 185                 190

Ala

<210> SEQ ID NO 64
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Gly Gln Gly Arg Gly Gly Phe Gly Gln Gly Ala Gly Gly Asn Ala
1               5                   10                  15

Ala Ala Ala Ala Ala Ala Ala Ala Ala Ala Ala Ala Ala Gln Gln Val
                20                  25                  30

Gly Gln Phe Gly Phe Gly Gly Arg Gly Gln Gly Gly Phe Gly Pro Phe
            35                  40                  45

Ala Gly Ser Ser Ala Ala Ala Ala Ala Ala Ser Ala Ala Ala Gly
        50                  55                  60

Gln Gly Gly Gln Gly Gln Gly Gly Phe Gly Gln Gly Ala Gly Gly Asn
65                  70                  75                  80

Ala Ala Ala Ala Ala Ala Ala Ala Ala Ala Ala Arg Gln Gly Gly
                85                  90                  95

Gln Gly Gln Gly Gly Phe Ser Gln Gly Ala Gly Gly Asn Ala Ala Ala
            100                 105                 110

Ala Ala Ala Ala Ala Ala Ala Ala Ala Ala Gln Gln Gly Gly
        115                 120                 125

Gln Gly Gly Phe Gly Gly Arg Gly Gln Gly Gly Phe Gly Pro Gly Ala
            130                 135                 140

Gly Ser Ser Ala Ala Ala Ala Ala Ala Thr Ala Ala Ala Gly Gln
145                 150                 155                 160

Gly Gly Gln Gly Arg Gly Gly Phe Gly Gln Gly Ala Gly Ser Asn Ala
                165                 170                 175

Ala Ala Ala Ala Ala Ala Ala Ala Ala Ala Ala Ala Ala Gly Gln
            180                 185                 190

<210> SEQ ID NO 65
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Gly Gln Gly Gly Gln Gly Gly Tyr Gly Gly Leu Gly Ser Gln Gly
1               5                   10                  15

Ala Gly Gln Gly Gly Tyr Gly Ala Gly Gln Gly Ala Ala Ala Ala Ala
                20                  25                  30

Ala Ala Ala Gly Gly Ala Gly Gly Ala Gly Arg Gly Gly Leu Gly Ala
            35                  40                  45

Gly Gly Ala Gly Gln Gly Tyr Gly Ala Gly Leu Gly Gln Gly Gly
            50                  55                  60

Ala Gly Gln Ala Ala Ala Ala Ala Ala Gly Gly Ala Gly Gly Ala
65                  70                  75                  80

Arg Gln Gly Gly Leu Gly Ala Gly Gly Ala Gly Gln Gly Tyr Gly Ala
                85                  90                  95

Gly Leu Gly Gly Gln Gly Gly Ala Gly Gln Gly Gly Ala Ala Ala Ala
                100                 105                 110

Ala Ala Ala Ala Gly Gly Gln Gly Gln Gly Gly Tyr Gly Gly Leu
            115                 120                 125

Gly Ser Gln Gly Ala Gly Gln Gly Gly Tyr Gly Ala Gly Gln Gly Gly
130                 135                 140

Ala Ala Ala Ala Ala Ala Ala Gly Gly Gln Gly Gln Gly Gly
145                 150                 155                 160

Tyr Gly Gly Leu Gly Ser Gln Gly Ala Gly Gln Gly Gly Tyr Gly Gly
                165                 170                 175

Arg Gln Gly Gly Ala Gly Ala Ala Ala Ala Ala Ala Ala
            180                 185                 190

<210> SEQ ID NO 66
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Gly Ala Gly Gln Arg Gly Tyr Gly Gly Leu Gly Asn Gln Gly Ala
1               5                   10                  15

Gly Arg Gly Gly Leu Gly Gly Gln Gly Ala Gly Ala Ala Ala Ala Ala
                20                  25                  30

Ala Ala Gly Gly Ala Gly Gln Gly Gly Tyr Gly Gly Leu Gly Asn Gln
            35                  40                  45

Gly Ala Gly Arg Gly Gly Gln Gly Ala Ala Ala Ala Gly Gly Ala
50                  55                  60

Gly Gln Gly Gly Tyr Gly Gly Leu Gly Ser Gln Gly Ala Gly Arg Gly
65                  70                  75                  80

Gly Gln Gly Ala Gly Ala Ala Ala Ala Ala Val Gly Ala Gly Gln
            85                  90                  95

Glu Gly Ile Arg Gly Gln Gly Ala Gly Gln Gly Gly Tyr Gly Gly Leu
                100                 105                 110

Gly Ser Gln Gly Ser Gly Arg Gly Gly Leu Gly Gly Gln Gly Ala Gly
            115                 120                 125

Ala Ala Ala Ala Ala Gly Gly Ala Gly Gln Gly Gly Leu Gly Gly
            130                 135                 140

Gln Gly Ala Gly Gln Gly Ala Gly Ala Ala Ala Ala Ala Gly Gly
145                 150                 155                 160

Val Arg Gln Gly Gly Tyr Gly Gly Leu Gly Ser Gln Gly Ala Gly Arg
                165                 170                 175

Gly Gly Gln Gly Ala Gly Ala Ala Ala Ala Ala
            180                 185

<210> SEQ ID NO 67
<211> LENGTH: 186
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 67

Gly Gly Ala Gly Gln Gly Gly Leu Gly Gly Gln Gly Ala Gly Gln Gly
1               5                   10                  15

Ala Gly Ala Ser Ala Ala Ala Ala Gly Gly Ala Gly Gln Gly Gly Tyr
            20                  25                  30

Gly Gly Leu Gly Ser Gln Gly Ala Gly Arg Gly Gly Glu Gly Ala Gly
        35                  40                  45

Ala Ala Ala Ala Ala Ala Gly Gly Ala Gly Gln Gly Gly Tyr Gly Gly
    50                  55                  60

Leu Gly Gly Gln Gly Ala Gly Gln Gly Gly Tyr Gly Gly Leu Gly Ser
65                  70                  75                  80

Gln Gly Ala Gly Arg Gly Gly Leu Gly Gly Gln Gly Ala Gly Ala Ala
            85                  90                  95

Ala Ala Gly Gly Ala Gly Gln Gly Gly Leu Gly Gly Gln Gly Ala Gly
            100                 105                 110

Gln Gly Ala Gly Ala Ala Ala Ala Ala Gly Gly Ala Gly Gln Gly
        115                 120                 125

Gly Tyr Gly Gly Leu Gly Ser Gln Gly Ala Gly Arg Gly Gly Leu Gly
    130                 135                 140

Gly Gln Gly Ala Gly Ala Val Ala Ala Ala Ala Gly Gly Ala Gly
145                 150                 155                 160

Gln Gly Gly Tyr Gly Gly Leu Gly Ser Gln Gly Ala Gly Arg Gly Gly
            165                 170                 175

Gln Gly Ala Gly Ala Ala Ala Ala Ala Ala
        180                 185

<210> SEQ ID NO 68
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Ala Gly Ala Gly Ala Gly Ala Gly Ser Gly Ala Gly Ala Ala Gly
1               5                   10                  15

Gly Tyr Gly Gly Gly Ala Gly Ala Gly Val Gly Ala Gly Gly Ala Gly
            20                  25                  30

Gly Tyr Asp Gln Gly Tyr Gly Ala Gly Ala Gly Ala Gly Ser Gly Ala
        35                  40                  45

Gly Ala Gly Gly Ala Gly Gly Tyr Gly Gly Gly Ala Gly Ala Gly Ala
    50                  55                  60

Asp Ala Gly Ala Gly Gly Ala Gly Gly Tyr Gly Gly Gly Ala Gly Ala
65                  70                  75                  80

Gly Ala Gly Ala Arg Ala Gly Ala Gly Val Gly Tyr Gly Gln
            85                  90                  95

Ser Tyr Gly Ala Gly Ala Gly Ala Gly Ala Gly Val Gly Ala Gly Gly
            100                 105                 110

Ala Gly Ala Gly Gly Ala Asp Gly Tyr Gly Gln Gly Tyr Gly Ala Gly
        115                 120                 125

Ala Gly Thr Gly Ala Gly Asp Ala Gly Gly Tyr Gly Gly Gly Ala Gly
        130                 135                 140
```

```
Ala Gly Ala Ser Ala Gly Ala Gly Gly Tyr Gly Gly Ala Gly Ala
145                 150                 155                 160

Gly Gly Val Gly Val Tyr Gly Lys Gly Tyr Gly Ser Gly Ser Gly Ala
                165                 170                 175

Gly Ala Ala Ala Ala Ala
            180
```

<210> SEQ ID NO 69
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Gly Gly Ala Gly Gly Tyr Gly Val Gly Gln Gly Tyr Gly Ala Gly Ala
1               5                   10                  15

Gly Ala Gly Ala Ala Ala Gly Ala Gly Ala Gly Ala Gly Gly Tyr
            20                  25                  30

Gly Ala Gly Gln Gly Tyr Gly Ala Gly Ala Gly Val Gly Ala Ala Ala
            35                  40                  45

Ala Ala Gly Ala Gly Ala Gly Val Gly Ala Gly Gly Tyr Gly Arg
50                  55                  60

Gly Gly Ala Gly Ala Gly Ala Gly Ala Gly Ala Ala Ala Gly Ala
65                  70                  75                  80

Gly Ala Gly Ala Ala Ala Gly Ala Gly Ala Gly Ala Gly Gly Tyr
                85                  90                  95

Gly Ala Gly Gln Gly Tyr Gly Ala Gly Ala Gly Val Gly Ala Ala Ala
                100                 105                 110

Ala Ala Gly Ala Gly Ala Gly Val Gly Gly Ala Gly Gly Tyr Gly Arg
        115                 120                 125

Gly Ala Gly Ala Gly Ala Gly Ala Gly Ala Gly Ala Gly Ala Gly Tyr
        130                 135                 140

Gly Arg Gly Ala Gly Ala Gly Ala Gly Ala Gly Ala Gly Ala Gly Gly
145                 150                 155                 160

Ala Gly Gly Tyr Gly Ala Gly Gln Gly Tyr Gly Ala Gly Ala Gly Ala
                165                 170                 175

Gly Ala Ala Ala Ala Ala
            180
```

<210> SEQ ID NO 70
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Gly Glu Ala Phe Ser Ala Ser Ala Ser Ser Ala Val Val Phe Glu
1               5                   10                  15

Ser Ala Gly Pro Gly Glu Glu Ala Gly Ser Ser Gly Asp Gly Ala Ser
            20                  25                  30

Ala Ala Ala Ser Ala Ala Ala Ala Gly Ala Gly Ser Gly Arg Arg
        35                  40                  45

Gly Pro Gly Gly Ala Arg Ser Arg Gly Gly Ala Gly Ala Gly Ala Gly
50                  55                  60
```

Ala Gly Ser Gly Val Gly Gly Tyr Gly Ser Gly Ser Gly Ala Gly Ala
65                  70                  75                  80

Gly Ala Gly Ala Gly Ala Gly Ala Gly Glu Gly Gly Phe Gly Glu
            85                  90                  95

Gly Gln Gly Tyr Gly Ala Gly Ala Gly Ala Gly Phe Gly Ser Gly Ala
            100                 105                 110

Gly Ala Gly Ala Gly Ala Gly Ser Gly Ala Gly Ala Gly Glu Gly Val
            115                 120                 125

Gly Ser Gly Ala Gly Ala Gly Ala Gly Ala Gly Phe Gly Val Gly Ala
            130                 135                 140

Gly Ala Gly Ala Gly Ala Gly Ala Gly Phe Gly Ser Gly Ala Gly Ala
145                 150                 155                 160

Gly Ser Gly Ala Gly Ala Gly Tyr Gly Ala Gly Arg Ala Gly Gly Arg
                165                 170                 175

Gly Arg Gly Gly Arg Gly
            180

<210> SEQ ID NO 71
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Glu Ala Phe Ser Ala Ser Ser Ala Ser Ser Ala Val Val Phe Glu
1               5                   10                  15

Ser Ala Gly Pro Gly Glu Glu Ala Gly Ser Ser Gly Gly Gly Ala Ser
            20                  25                  30

Ala Ala Ala Ser Ala Ala Ala Ala Gly Ala Gly Ser Gly Arg Arg
            35                  40                  45

Gly Pro Gly Gly Ala Arg Ser Arg Gly Gly Ala Gly Ala Gly Ala Gly
            50                  55                  60

Ala Gly Ser Gly Val Gly Gly Tyr Gly Ser Gly Ser Gly Ala Gly Ala
65                  70                  75                  80

Gly Ala Gly Ala Gly Ala Gly Ala Gly Glu Gly Gly Phe Gly Glu
            85                  90                  95

Gly Gln Gly Tyr Gly Ala Gly Ala Gly Ala Gly Phe Gly Ser Gly Ala
            100                 105                 110

Gly Ala Gly Ala Gly Ala Gly Ser Gly Ala Gly Ala Gly Glu Gly Val
            115                 120                 125

Gly Ser Gly Ala Gly Ala Gly Ala Gly Ala Gly Phe Gly Val Gly Ala
            130                 135                 140

Gly Ala Gly Ala Gly Ala Gly Ala Gly Phe Gly Ser Gly Ala Gly Ala
145                 150                 155                 160

Gly Ser Gly Ala Gly Ala Gly Tyr Gly Ala Gly Arg Ala Gly Gly Arg
                165                 170                 175

Gly Arg Gly Gly Arg Gly
            180

<210> SEQ ID NO 72
<211> LENGTH: 182
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 72

Gly Asn Gly Leu Gly Gln Ala Leu Leu Ala Asn Gly Val Leu Asn Ser
1               5                   10                  15

Gly Asn Tyr Leu Gln Leu Ala Asn Ser Leu Ala Tyr Ser Phe Gly Ser
            20                  25                  30

Ser Leu Ser Gln Tyr Ser Ser Ala Ala Gly Ala Ser Ala Ala Gly
        35                  40                  45

Ala Ala Ser Gly Ala Ala Gly Ala Gly Ala Ala Ser Ser Gly
    50                  55                  60

Gly Ser Ser Gly Ser Ala Ser Ser Thr Thr Thr Thr Thr Thr
65                  70                  75                  80

Ser Thr Ser Ala Ala Ala Ala Ala Ala Ala Ala Ala Ala Ser
                85                  90                  95

Ala Ala Ala Ser Thr Ser Ala Ser Ala Ser Ala Ser Ala Ser
            100                 105                 110

Ala Ser Ala Phe Ser Gln Thr Phe Val Gln Thr Val Leu Gln Ser Ala
            115                 120                 125

Ala Phe Gly Ser Tyr Phe Gly Gly Asn Leu Ser Leu Gln Ser Ala Gln
        130                 135                 140

Ala Ala Ala Ser Ala Ala Ala Gln Ala Ala Ala Gln Gln Ile Gly Leu
145                 150                 155                 160

Gly Ser Tyr Gly Tyr Ala Leu Ala Asn Ala Val Ala Ser Ala Phe Ala
                165                 170                 175

Ser Ala Gly Ala Asn Ala
            180

<210> SEQ ID NO 73
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Asn Gly Leu Gly Gln Ala Leu Leu Ala Asn Gly Val Leu Asn Ser
1               5                   10                  15

Gly Asn Tyr Leu Gln Leu Ala Asn Ser Leu Ala Tyr Ser Phe Gly Ser
            20                  25                  30

Ser Leu Ser Gln Tyr Ser Ser Ala Ala Gly Ala Ser Ala Ala Gly
        35                  40                  45

Ala Ala Ser Gly Ala Ala Gly Ala Gly Ala Ala Ser Ser Gly
    50                  55                  60

Gly Ser Ser Gly Ser Ala Ser Ser Thr Thr Thr Thr Thr Thr
65                  70                  75                  80

Ser Thr Ser Ala Ala Ala Ala Ala Ala Ala Ala Ala Ala Ser
                85                  90                  95

Ala Ala Ala Ser Thr Ser Ala Ser Ala Ser Ala Ser Ala Ser
            100                 105                 110

Ala Ser Ala Phe Ser Gln Thr Phe Val Gln Thr Val Leu Gln Ser Ala
            115                 120                 125

Ala Phe Gly Ser Tyr Phe Gly Gly Asn Leu Ser Leu Gln Ser Ala Gln
        130                 135                 140

Ala Ala Ala Ser Ala Ala Ala Gln Ala Ala Ala Gln Gln Ile Gly Leu

```
145                 150                 155                 160
Gly Ser Tyr Gly Tyr Ala Leu Ala Asn Ala Val Ala Ser Ala Phe Ala
                165                 170                 175

Ser Ala Gly Ala Asn Ala
            180

<210> SEQ ID NO 74
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Asn Gly Leu Gly Gln Ala Leu Leu Ala Asn Gly Val Leu Asn Ser
1               5                   10                  15

Gly Asn Tyr Leu Gln Leu Ala Asn Ser Leu Ala Tyr Ser Phe Gly Ser
            20                  25                  30

Ser Leu Ser Gln Tyr Ser Ser Ala Ala Gly Ala Ser Ala Ala Gly
        35                  40                  45

Ala Ala Ser Gly Ala Ala Gly Ala Gly Ala Gly Ala Ala Ser Ser Gly
50                  55                  60

Gly Ser Ser Gly Ser Ala Ser Ser Ser Thr Thr Thr Thr Thr Thr
65                  70                  75                  80

Ser Thr Ser Ala Ala Ala Ala Ala Ala Ala Ala Ala Ala Ala Ser
                85                  90                  95

Ala Ala Ala Ser Thr Ser Ala Ser Ala Ser Ala Ser Ala Ser
                100                 105                 110

Ala Ser Ala Phe Ser Gln Thr Phe Val Gln Thr Val Leu Gln Ser Ala
                115                 120                 125

Ala Phe Gly Ser Tyr Phe Gly Gly Asn Leu Ser Leu Gln Ser Ala Gln
            130                 135                 140

Ala Ala Ala Ser Ala Ala Ala Gln Ala Ala Gln Gln Ile Gly Leu
145                 150                 155                 160

Gly Ser Tyr Gly Tyr Ala Leu Ala Asn Ala Val Ala Ser Ala Phe Ala
                165                 170                 175

Ser Ala Gly Ala Asn Ala
            180

<210> SEQ ID NO 75
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Ala Ser Gly Ala Gly Gln Gly Gln Gly Tyr Gly Gln Gln Gly Gln
1               5                   10                  15

Gly Gly Ser Ser Ala Ala Ala Ala Ala Ala Ala Ala Ala Ala
            20                  25                  30

Ala Ala Ala Gln Gly Gln Gly Gly Tyr Gly Gln Gly Gln Gly
        35                  40                  45

Ser Ala Ala Ala Ala Ala Ala Ala Ala Gly Ala Ser Gly Ala
50                  55                  60

Gly Gln Gly Gln Gly Tyr Gly Gln Gln Gly Gln Gly Ser Ala Ala Ala
```

```
                65                  70                  75                  80
Ala Ala Ala Ala Ala Ala Gly Ala Ser Gly Ala Gly Gln Gly Gln
                    85                  90                  95

Gly Tyr Gly Gln Gln Gly Gln Gly Gly Ser Ser Ala Ala Ala Ala
                    100                 105                 110

Ala Ala Ala Ala Ala Ala Ala Ala Ala Ala Gln Gly Gln Gly Tyr
                    115                 120                 125

Gly Gln Gln Gly Gln Gly Ser Ala Ala Ala Ala Ala Ala Ala Ala
                    130                 135                 140

Gly Ala Ser Gly Ala Gly Gln Gly Gln Gly Tyr Gly Gln Gln Gly Gln
145                 150                 155                 160

Gly Gly Ser Ser Ala Ala Ala Ala Ala Ala Ala Ala Ala Ala
                    165                 170                 175

Ala Ala Ala Ala
            180

<210> SEQ ID NO 76
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gly Arg Gly Gln Gly Gly Tyr Gly Gln Gly Ser Gly Gly Asn Ala Ala
1               5                   10                  15

Ala Ala Ala Ala Ala Gly Gln Gly Gly Phe Gly Gln Glu Gly Asn
                    20                  25                  30

Gly Gln Gly Ala Gly Ser Ala Ala Ala Ala Ala Ala Ala Ala Ala
                35                  40                  45

Ala Ala Gly Gly Ser Gly Gln Gly Arg Tyr Gly Gly Arg Gly Gln Gly
                50                  55                  60

Gly Tyr Gly Gln Gly Ala Gly Ala Ala Ala Ser Ala Ala Ala Ala Ala
65                  70                  75                  80

Ala Ala Ala Ala Ala Gly Gln Gly Gly Phe Gly Gly Gln Glu Gly Asn
                    85                  90                  95

Gly Gln Gly Ala Gly Ser Ala Ala Ala Ala Ala Ala Ala Ala Ala
                    100                 105                 110

Ala Ala Gly Gly Ser Gly Gln Gly Gly Tyr Gly Gly Arg Gly Gln Gly
                    115                 120                 125

Gly Tyr Gly Gln Gly Ala Gly Ala Ala Ala Ala Ala Ala Ala Ala
                    130                 135                 140

Ala Ala Ala Ala Ala Gly Gln Gly Gly Gln Gly Gly Phe Gly Ser Gln
145                 150                 155                 160

Gly Gly Asn Gly Gln Gly Ala Gly Ser Ala Ala Ala Ala Ala Ala Ala
                    165                 170                 175

Ala Ala Ala

<210> SEQ ID NO 77
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77
```

Gly Gln Asn Thr Pro Trp Ser Ser Thr Glu Leu Ala Asp Ala Phe Ile
1               5                   10                  15

Asn Ala Phe Met Asn Glu Ala Gly Arg Thr Gly Ala Phe Thr Ala Asp
            20                  25                  30

Gln Leu Asp Asp Met Ser Thr Ile Gly Asp Thr Ile Lys Thr Ala Met
        35                  40                  45

Asp Lys Met Ala Arg Ser Asn Lys Ser Ser Lys Gly Lys Leu Gln Ala
    50                  55                  60

Leu Asn Met Ala Phe Ala Ser Ser Met Ala Glu Ile Ala Ala Val Glu
65                  70                  75                  80

Gln Gly Gly Leu Ser Val Asp Ala Lys Thr Asn Ala Ile Ala Asp Ser
                85                  90                  95

Leu Asn Ser Ala Phe Tyr Gln Thr Thr Gly Ala Ala Asn Pro Gln Phe
                100                 105                 110

Val Asn Glu Ile Arg Ser Leu Ile Asn Met Phe Ala Gln Ser Ser Ala
            115                 120                 125

Asn Glu Val Ser Tyr Gly Gly Tyr Gly Gly Gln Ser Ala Gly Ala
            130                 135                 140

Ala Ala Ser Ala Ala Ala Ala Gly Gly Gly Gln Gly Gly Tyr Gly
145                 150                 155                 160

Asn Leu Gly Gly Gln Gly Ala Gly Ala Ala Ala Ala Ala Ala Ser
                165                 170                 175

Ala Ala

<210> SEQ ID NO 78
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Gln Asn Thr Pro Trp Ser Ser Thr Glu Leu Ala Asp Ala Phe Ile
1               5                   10                  15

Asn Ala Phe Leu Asn Glu Ala Gly Arg Thr Gly Ala Phe Thr Ala Asp
            20                  25                  30

Gln Leu Asp Asp Met Ser Thr Ile Gly Asp Thr Leu Lys Thr Ala Met
        35                  40                  45

Asp Lys Met Ala Arg Ser Asn Lys Ser Ser Gln Ser Lys Leu Gln Ala
    50                  55                  60

Leu Asn Met Ala Phe Ala Ser Ser Met Ala Glu Ile Ala Ala Val Glu
65                  70                  75                  80

Gln Gly Gly Leu Ser Val Ala Glu Lys Thr Asn Ala Ile Ala Asp Ser
                85                  90                  95

Leu Asn Ser Ala Phe Tyr Gln Thr Thr Gly Ala Val Asn Val Gln Phe
                100                 105                 110

Val Asn Glu Ile Arg Ser Leu Ile Ser Met Phe Ala Gln Ser Ala
            115                 120                 125

Asn Glu Val Ser Tyr Gly Gly Tyr Gly Gly Gln Gly Gly Gln
            130                 135                 140

Ser Ala Gly Ala Ala Ala Ala Ser Gly Ala Gly Gln Gly
145                 150                 155                 160

Gly Tyr Gly Gly Leu Gly Gly Gln Gly Ala Gly Ser Ala Ala Ala Ala
                165                 170                 175

<210> SEQ ID NO 79
<211> LENGTH: 177
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

Gly Gly Gln Gly Gly Gln Gly Gly Tyr Gly Gly Leu Gly Ser Gln Gly
1               5                   10                  15

Ala Gly Gln Gly Gly Tyr Gly Gln Gly Gly Ala Ala Ala Ala Ala Ala
            20                  25                  30

Ser Ala Gly Gly Gln Gly Gly Gln Gly Gly Tyr Gly Gly Leu Gly Ser
        35                  40                  45

Gln Gly Ala Gly Gln Gly Gly Tyr Gly Gly Ala Phe Ser Gly Gln
    50                  55                  60

Gln Gly Gly Ala Ala Ser Val Ala Thr Ala Ser Ala Ala Ser Arg
65                  70                  75                  80

Leu Ser Ser Pro Gly Ala Ala Ser Arg Val Ser Ser Ala Val Thr Ser
                85                  90                  95

Leu Val Ser Ser Gly Gly Pro Thr Asn Ser Ala Ala Leu Ser Asn Thr
            100                 105                 110

Ile Ser Asn Val Val Ser Gln Ile Ser Ser Ser Asn Pro Gly Leu Ser
        115                 120                 125

Gly Cys Asp Val Leu Val Gln Ala Leu Leu Glu Ile Val Ser Ala Leu
    130                 135                 140

Val His Ile Leu Gly Ser Ala Asn Ile Gly Gln Val Asn Ser Ser Gly
145                 150                 155                 160

Val Gly Arg Ser Ala Ser Ile Val Gly Gln Ser Ile Asn Gln Ala Phe
                165                 170                 175

Ser

<210> SEQ ID NO 80
<211> LENGTH: 177
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

Gly Gly Ala Gly Gln Gly Gly Tyr Gly Gly Leu Gly Gly Gln Gly Ala
1               5                   10                  15

Gly Ala Ala Ala Ala Ala Gly Gly Ala Gly Gln Gly Gly Tyr Gly
            20                  25                  30

Gly Gln Gly Ala Gly Gln Gly Ala Ala Ala Ala Ala Ser Gly Ala
        35                  40                  45

Gly Gln Gly Gly Tyr Glu Gly Pro Gly Ala Gly Gln Gly Ala Gly Ala
    50                  55                  60

Ala Ala Ala Ala Gly Ala Gly Gln Gly Gly Tyr Gly Gly Leu
65                  70                  75                  80

Gly Gly Gln Gly Ala Gly Gln Gly Ala Gly Ala Ala Ala Ala Ala
                85                  90                  95

Gly Gly Ala Gly Gln Gly Gly Tyr Gly Gly Leu Gly Gly Gln Gly Ala

```
                100                 105                 110
Gly Gln Gly Ala Gly Ala Ala Ala Ala Ala Gly Gly Ala Gly Gln
            115                 120                 125
Gly Gly Tyr Gly Gly Gln Gly Ala Gln Gly Ala Ala Ala Ala
            130                 135                 140
Ala Gly Gly Ala Gly Gln Gly Gly Tyr Gly Leu Gly Ser Gly Gln
145                 150                 155                 160
Gly Gly Tyr Gly Arg Gln Gly Ala Gly Ala Ala Ala Ala Ala Ala
                165                 170                 175
Ala

<210> SEQ ID NO 81
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Ala Ser Ser Ala Ala Ala Ala Ala Ala Thr Ala Thr Ser Gly
1               5                   10                  15
Gly Ala Pro Gly Gly Tyr Gly Gly Tyr Gly Pro Gly Ile Gly Gly Ala
            20                  25                  30
Phe Val Pro Ala Ser Thr Thr Gly Thr Gly Ser Gly Ser Ser Gly
            35                  40                  45
Ala Gly Ala Ala Gly Ser Gly Gly Leu Gly Gly Leu Gly Ser Ser Gly
50                  55                  60
Gly Ser Gly Gly Leu Gly Gly Gly Asn Gly Ser Gly Ala Ser Ala
65                  70                  75                  80
Ala Ala Ser Ala Ala Ala Ser Ser Ser Pro Gly Ser Gly Gly Tyr
                85                  90                  95
Gly Pro Gly Gln Gly Val Gly Ser Gly Ser Gly Ser Ala Ala Gly
            100                 105                 110
Gly Ser Gly Thr Gly Ser Gly Ala Gly Gly Pro Gly Ser Gly Gly Tyr
            115                 120                 125
Gly Gly Pro Gln Phe Phe Ala Ser Ala Tyr Gly Gly Gln Leu Leu
            130                 135                 140
Gly Thr Ser Gly Tyr Gly Asn Gly Gln Gly Gly Ala Ser Gly Thr Gly
145                 150                 155                 160
Ser Gly Gly Val Gly Gly Ser Gly Ser Gly Ala Gly Ser Asn Ser
                165                 170                 175

<210> SEQ ID NO 82
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Gln Pro Ile Trp Thr Asn Pro Asn Ala Ala Met Thr Met Thr Asn
1               5                   10                  15
Asn Leu Val Gln Cys Ala Ser Arg Ser Gly Val Leu Thr Ala Asp Gln
            20                  25                  30
Met Asp Asp Met Gly Met Met Ala Asp Ser Val Asn Ser Gln Met Gln
            35                  40                  45
```

```
Lys Met Gly Pro Asn Pro Gln His Arg Leu Arg Ala Met Asn Thr
    50                  55                  60

Ala Met Ala Ala Glu Val Ala Glu Val Val Ala Thr Ser Pro Pro Gln
65                  70                  75                  80

Ser Tyr Ser Ala Val Leu Asn Thr Ile Gly Ala Cys Leu Arg Glu Ser
                85                  90                  95

Met Met Gln Ala Thr Gly Ser Val Asp Asn Ala Phe Thr Asn Glu Val
            100                 105                 110

Met Gln Leu Val Lys Met Leu Ser Ala Asp Ser Ala Asn Glu Val Ser
        115                 120                 125

Thr Ala Ser Ala Ser Gly Ala Ser Tyr Ala Thr Ser Thr Ser Ser Ala
    130                 135                 140

Val Ser Ser Ser Gln Ala Thr Gly Tyr Ser Thr Ala Ala Gly Tyr Gly
145                 150                 155                 160

Asn Ala Ala Gly Ala Gly Ala Gly Ala Ala Ala Ala Val Ser
                165                 170
```

```
<210> SEQ ID NO 83
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83
```

```
Gly Gln Lys Ile Trp Thr Asn Pro Asp Ala Ala Met Ala Met Thr Asn
1               5                   10                  15

Asn Leu Val Gln Cys Ala Gly Arg Ser Gly Ala Leu Thr Ala Asp Gln
                20                  25                  30

Met Asp Asp Leu Gly Met Val Ser Asp Ser Val Asn Ser Gln Val Arg
            35                  40                  45

Lys Met Gly Ala Asn Ala Pro Pro His Lys Ile Lys Ala Met Ser Thr
    50                  55                  60

Ala Val Ala Ala Gly Val Ala Glu Val Val Ala Ser Ser Pro Pro Gln
65                  70                  75                  80

Ser Tyr Ser Ala Val Leu Asn Thr Ile Gly Gly Cys Leu Arg Glu Ser
                85                  90                  95

Met Met Gln Val Thr Gly Ser Val Asp Asn Thr Phe Thr Thr Glu Met
            100                 105                 110

Met Gln Met Val Asn Met Phe Ala Ala Asp Asn Ala Asn Glu Val Ser
        115                 120                 125

Ala Ser Ala Ser Gly Ser Gly Ala Ser Tyr Ala Thr Gly Thr Ser Ser
    130                 135                 140

Ala Val Ser Thr Ser Gln Ala Thr Gly Tyr Ser Thr Ala Gly Gly Tyr
145                 150                 155                 160

Gly Thr Ala Ala Gly Ala Gly Ala Gly Ala Ala Ala Ala
                165                 170
```

```
<210> SEQ ID NO 84
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84
```

Gly Ser Gly Tyr Gly Ala Gly Ala Gly Ala Gly Ser Gly Tyr
1               5                   10                  15

Gly Ala Gly Ala Gly Ala Gly Ser Gly Tyr Gly Ala Gly Ala
            20                  25                  30

Gly Ala Gly Ser Gly Tyr Val Ala Gly Ala Gly Ala Gly Ala
            35                  40                  45

Gly Ser Gly Tyr Gly Ala Gly Ala Gly Ala Gly Ser Ser Tyr
        50                  55                  60

Ser Ala Gly Ala Gly Ala Gly Ala Ser Gly Tyr Gly Ala Gly Ser
65                  70                  75                  80

Ser Ala Ser Ala Gly Ser Ala Val Ser Thr Gln Thr Val Ser Ser Ser
                85                  90                  95

Ala Thr Thr Ser Ser Gln Ser Ala Ala Ala Thr Gly Ala Ala Tyr
                100                 105                 110

Gly Thr Arg Ala Ser Thr Gly Ser Gly Ala Ser Ala Gly Ala Ala Ala
            115                 120                 125

Ser Gly Ala Gly Ala Gly Tyr Gly Gly Gln Ala Gly Tyr Gly Gln Gly
    130                 135                 140

Gly Gly Ala Ala Ala Tyr Arg Ala Gly Ala Gly Ser Gln Ala Ala Tyr
145                 150                 155                 160

Gly Gln Gly Ala Ser Gly Ser Ser Gly Ala Ala Ala Ala
                165                 170

<210> SEQ ID NO 85
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gly Gly Gln Gly Gly Arg Gly Gly Phe Gly Gly Leu Ser Ser Gln Gly
1               5                   10                  15

Ala Gly Gly Ala Gly Gln Gly Gly Ser Gly Ala Ala Ala Ala Ala Ala
            20                  25                  30

Ala Ala Gly Gly Asp Gly Gly Ser Gly Leu Gly Asp Tyr Gly Ala Gly
        35                  40                  45

Arg Gly Tyr Gly Ala Gly Leu Gly Gly Ala Gly Gly Ala Gly Val Ala
    50                  55                  60

Ser Ala Ala Ala Ser Ala Ala Ser Arg Leu Ser Ser Pro Ser Ala
65                  70                  75                  80

Ala Ser Arg Val Ser Ser Ala Val Thr Ser Leu Ile Ser Gly Gly
                85                  90                  95

Pro Thr Asn Pro Ala Ala Leu Ser Asn Thr Phe Ser Asn Val Val Tyr
                100                 105                 110

Gln Ile Ser Val Ser Ser Pro Gly Leu Ser Gly Cys Asp Val Leu Ile
            115                 120                 125

Gln Ala Leu Leu Glu Leu Val Ser Ala Leu Val His Ile Leu Gly Ser
    130                 135                 140

Ala Ile Ile Gly Gln Val Asn Ser Ser Ala Ala Gly Glu Ser Ala Ser
145                 150                 155                 160

Leu Val Gly Gln Ser Val Tyr Gln Ala Phe Ser
                165                 170

```
<210> SEQ ID NO 86
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gly Val Gly Gln Ala Ala Thr Pro Trp Glu Asn Ser Gln Leu Ala Glu
1               5                   10                  15

Asp Phe Ile Asn Ser Phe Leu Arg Phe Ile Ala Gln Ser Gly Ala Phe
            20                  25                  30

Ser Pro Asn Gln Leu Asp Asp Met Ser Ser Ile Gly Asp Thr Leu Lys
        35                  40                  45

Thr Ala Ile Glu Lys Met Ala Gln Ser Arg Lys Ser Ser Lys Ser Lys
50                  55                  60

Leu Gln Ala Leu Asn Met Ala Phe Ala Ser Ser Met Ala Glu Ile Ala
65                  70                  75                  80

Val Ala Glu Gln Gly Gly Leu Ser Leu Glu Ala Lys Thr Asn Ala Ile
                85                  90                  95

Ala Asn Ala Leu Ala Ser Ala Phe Leu Glu Thr Thr Gly Phe Val Asn
            100                 105                 110

Gln Gln Phe Val Ser Glu Ile Lys Ser Leu Ile Tyr Met Ile Ala Gln
        115                 120                 125

Ala Ser Ser Asn Glu Ile Ser Gly Ser Ala Ala Ala Gly Gly Gly
130                 135                 140

Ser Gly Gly Gly Gly Ser Gly Gln Gly Gly Tyr Gly Gln Gly Ala
145                 150                 155                 160

Ser Ala Ser Ala Ser Ala Ala Ala Ala
                165

<210> SEQ ID NO 87
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gly Gly Gly Asp Gly Tyr Gly Gln Gly Gly Tyr Gly Asn Gln Arg Gly
1               5                   10                  15

Val Gly Ser Tyr Gly Gln Gly Ala Gly Ala Gly Ala Ala Ala Thr Ser
            20                  25                  30

Ala Ala Gly Gly Ala Gly Ser Gly Arg Gly Gly Tyr Gly Glu Gln Gly
        35                  40                  45

Gly Leu Gly Gly Tyr Gly Gln Gly Ala Gly Ala Gly Ala Ala Ser Thr
50                  55                  60

Ala Ala Gly Gly Gly Asp Gly Tyr Gly Gln Gly Gly Tyr Gly Asn Gln
65                  70                  75                  80

Gly Gly Arg Gly Ser Tyr Gly Gln Gly Ser Gly Ala Gly Ala Gly Ala
                85                  90                  95

Ala Val Ala Ala Ala Ala Gly Gly Ala Val Ser Gly Gln Gly Gly Tyr
            100                 105                 110

Asp Gly Glu Gly Gly Gln Gly Gly Tyr Gly Gln Gly Ser Gly Ala Gly
        115                 120                 125

Ala Ala Val Ala Ala Ala Ser Gly Gly Thr Gly Ala Gly Gln Gly Gly
```

```
                130                 135                 140
Tyr Gly Ser Gln Gly Ser Gln Ala Gly Tyr Gly Gln Gly Ala Gly Phe
145                 150                 155                 160

Arg Ala Ala Ala Thr Ala Ala Ala
                165

<210> SEQ ID NO 88
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gly Ala Gly Ala Gly Tyr Gly Gly Gln Val Gly Tyr Gly Gln Gly Ala
1               5                   10                  15

Gly Ala Ser Ala Gly Ala Ala Ala Gly Ala Gly Ala Gly Tyr Gly
                20                  25                  30

Gly Gln Ala Gly Tyr Gly Gln Gly Ala Gly Ser Ala Gly Ala Ala
            35                  40                  45

Ala Ala Gly Ala Gly Ala Gly Arg Gln Ala Gly Tyr Gly Gln Gly Ala
50                  55                  60

Gly Ala Ser Ala Arg Ala Ala Ala Gly Ala Gly Thr Gly Tyr Gly
65                  70                  75                  80

Gln Gly Ala Gly Ala Ser Ala Gly Ala Ala Ala Gly Ala Gly Ala
                85                  90                  95

Gly Ser Gln Val Gly Tyr Gly Gln Ala Gly Ala Ser Ser Gly Ala
                100                 105                 110

Ala Ala Ala Ala Gly Ala Gly Ala Gly Tyr Gly Gly Gln Val Gly Tyr
            115                 120                 125

Glu Gln Gly Ala Gly Ala Ser Ala Gly Ala Glu Ala Ala Ser Ser
1   130                 135                 140

Ala Gly Ala Gly Tyr Gly Gly Gln Ala Gly Tyr Gly Gln Gly Ala Gly
145                 150                 155                 160

Ala Ser Ala Gly Ala Ala Ala Ala
                165

<210> SEQ ID NO 89
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gly Gly Ala Gly Gln Gly Gly Tyr Gly Gly Leu Gly Gly Gln Gly Ala
1               5                   10                  15

Gly Gln Gly Gly Leu Gly Gly Gln Arg Ala Gly Ala Ala Ala Ala
            20                  25                  30

Ala Gly Gly Ala Gly Gln Gly Gly Tyr Gly Gly Leu Gly Ser Gln Gly
            35                  40                  45

Ala Gly Arg Gly Gly Tyr Gly Gly Val Gly Ser Gly Ala Ser Ala Ala
        50                  55                  60

Ser Ala Ala Ala Ser Arg Leu Ser Ser Pro Glu Ala Ser Ser Arg Val
65                  70                  75                  80

Ser Ser Ala Val Ser Asn Leu Val Ser Ser Gly Pro Thr Asn Ser Ala
```

```
                    85                  90                  95
Ala Leu Ser Ser Thr Ile Ser Asn Val Val Ser Gln Ile Ser Ala Ser
                100                 105                 110

Asn Pro Gly Leu Ser Gly Cys Asp Val Leu Val Gln Ala Leu Leu Glu
            115                 120                 125

Val Val Ser Ala Leu Ile Gln Ile Leu Gly Ser Ser Ser Ile Gly Gln
        130                 135                 140

Val Asn Tyr Gly Thr Ala Gly Gln Ala Ala Gln Ile Val Gly Gln Ser
145                 150                 155                 160

Val Tyr Gln Ala Leu Gly
                165

<210> SEQ ID NO 90
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gly Gly Tyr Gly Pro Gly Ser Gly Gln Gln Gly Pro Gly Gly Ala Gly
1               5                   10                  15

Gln Gln Gly Pro Gly Gly Gln Gly Pro Tyr Gly Pro Gly Ser Ser Ser
            20                  25                  30

Ala Ala Ala Val Gly Gly Tyr Gly Pro Ser Ser Gly Leu Gln Gly Pro
        35                  40                  45

Ala Gly Gln Gly Pro Tyr Gly Pro Gly Ala Ala Ser Ala Ala Ala
    50                  55                  60

Ala Ala Gly Ala Ser Arg Leu Ser Ser Pro Gln Ala Ser Ser Arg Val
65                  70                  75                  80

Ser Ser Ala Val Ser Ser Leu Val Ser Ser Gly Pro Thr Asn Ser Ala
                85                  90                  95

Ala Leu Thr Asn Thr Ile Ser Ser Val Val Ser Gln Ile Ser Ala Ser
                100                 105                 110

Asn Pro Gly Leu Ser Gly Cys Asp Val Leu Ile Gln Ala Leu Leu Glu
            115                 120                 125

Ile Val Ser Ala Leu Val His Ile Leu Gly Tyr Ser Ser Ile Gly Gln
        130                 135                 140

Ile Asn Tyr Asp Ala Ala Gln Tyr Ala Ser Leu Val Gly Gln Ser
145                 150                 155                 160

Val Ala Gln Ala Leu Ala
                165

<210> SEQ ID NO 91
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gly Gly Ala Gly Ala Gly Gln Gly Ser Tyr Gly Gly Gln Gly Gly Tyr
1               5                   10                  15

Gly Gln Gly Gly Ala Gly Ala Ala Thr Ala Thr Ala Ala Ala Gly
            20                  25                  30

Gly Ala Gly Ser Gly Gln Gly Gly Tyr Gly Gly Gln Gly Gly Leu Gly
```

```
            35                  40                  45
Gly Tyr Gly Gln Gly Ala Gly Ala Ala Ala Ala Ala Ala
            50                  55                  60
Ala Ala Gly Gly Ala Gly Ala Gly Gln Gly Gly Tyr Gly Gly Gln Gly
65                  70                  75                  80
Gly Gln Gly Gly Tyr Gly Gln Gly Ala Gly Ala Ala Ala
                85                  90                  95
Ala Ala Gly Gly Ala Gly Ala Gly Gln Gly Gly Tyr Gly Gly Gln Gly
            100                 105                 110
Gly Tyr Gly Gln Gly Gly Ala Gly Ala Ala Ala Ala Ala
            115                 120                 125
Ala Ser Gly Gly Ser Gly Ser Gly Gln Gly Gly Tyr Gly Gly Gln Gly
            130                 135                 140
Gly Leu Gly Gly Tyr Gly Gln Gly Ala Gly Ala Gly Ala Gly Ala Ala
145                 150                 155                 160

Ala Ser Ala Ala Ala Ala
            165

<210> SEQ ID NO 92
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Gln Gly Gly Gln Gly Gly Tyr Gly Arg Gln Ser Gln Gly Ala Gly
1               5                   10                  15
Ser Ala Ala Ala Ala Ala Ala Ala Ala Ala Ala Ala Ala Ala Ala Gly
                20                  25                  30
Ser Gly Gln Gly Gly Tyr Gly Gly Gln Gly Gly Tyr Gly Gln
            35                  40                  45
Ser Ser Ala Ser Ala Ser Ala Ala Ser Ala Ala Ser Thr Val Ala
            50                  55                  60
Asn Ser Val Ser Arg Leu Ser Ser Pro Ser Ala Val Ser Arg Val Ser
65                  70                  75                  80
Ser Ala Val Ser Ser Leu Val Ser Asn Gly Gln Val Asn Met Ala Ala
                85                  90                  95
Leu Pro Asn Ile Ile Ser Asn Ile Ser Ser Val Ser Ala Ser Ala
            100                 105                 110
Pro Gly Ala Ser Gly Cys Glu Val Ile Val Gln Ala Leu Leu Glu Val
            115                 120                 125
Ile Thr Ala Leu Val Gln Ile Val Ser Ser Ser Val Gly Tyr Ile
            130                 135                 140
Asn Pro Ser Ala Val Asn Gln Ile Thr Asn Val Val Ala Asn Ala Met
145                 150                 155                 160

Ala Gln Val Met Gly
            165

<210> SEQ ID NO 93
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 93

```
Gly Gly Ala Gly Gln Gly Gly Tyr Gly Gly Leu Gly Gly Gln Gly Ser
1               5                   10                  15
Gly Ala Ala Ala Ala Gly Thr Gly Gln Gly Gly Tyr Gly Ser Leu Gly
                20                  25                  30
Gly Gln Gly Ala Gly Ala Ala Gly Ala Ala Ala Ala Val Gly Gly
            35                  40                  45
Ala Gly Gln Gly Gly Tyr Gly Ser Val Gly Ser Ala Ala Ala Ser Ala
        50                  55                  60
Ala Ala Ser Arg Leu Ser Ser Pro Glu Ala Ser Ser Arg Val Ser Ser
65                  70                  75                  80
Ala Val Ser Asn Leu Val Ser Ser Gly Pro Thr Asn Ser Ala Ala Leu
                85                  90                  95
Ser Asn Thr Ile Ser Asn Val Val Ser Gln Ile Ser Ser Ser Asn Pro
                100                 105                 110
Gly Leu Ser Gly Cys Asp Val Leu Val Gln Ala Leu Leu Glu Val Val
            115                 120                 125
Ser Ala Leu Ile His Ile Leu Gly Ser Ser Ser Ile Gly Gln Val Asn
        130                 135                 140
Tyr Gly Ser Ala Gly Gln Ala Thr Gln Ile Val Gly Gln Ser Val Tyr
145                 150                 155                 160
Gln Ala Leu Gly
```

<210> SEQ ID NO 94
<211> LENGTH: 164
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Gly Ala Gly Ala Gly Gly Ala Gly Gly Tyr Gly Ala Gly Gln Gly Tyr
1               5                   10                  15
Gly Ala Gly Ala Gly Ala Gly Ala Ala Ala Gly Ala Gly Ala Gly Gly
                20                  25                  30
Ala Arg Gly Tyr Gly Ala Arg Gln Gly Tyr Gly Ser Gly Ala Gly Ala
            35                  40                  45
Gly Ala Gly Ala Arg Ala Gly Gly Ala Gly Gly Tyr Gly Arg Gly Ala
        50                  55                  60
Gly Ala Gly Ala Ala Ala Ala Ser Gly Ala Gly Ala Gly Gly Tyr Gly
65                  70                  75                  80
Ala Gly Gln Gly Tyr Gly Ala Gly Ala Gly Ala Val Ala Ser Ala Ala
                85                  90                  95
Ala Gly Ala Gly Ser Gly Ala Gly Gly Ala Gly Gly Tyr Gly Arg Gly
                100                 105                 110
Ala Gly Ala Val Ala Gly Ala Gly Ala Gly Ala Gly Gly Tyr Gly
            115                 120                 125
Ala Gly Ala Gly Ala Ala Ala Gly Val Gly Ala Gly Gly Ser Gly Gly
        130                 135                 140
Tyr Gly Gly Arg Gln Gly Gly Tyr Ser Ala Gly Ala Gly Ala Gly Ala
145                 150                 155                 160
Ala Ala Ala Ala
```

<210> SEQ ID NO 95

```
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gly Gln Gly Gly Gln Gly Gly Tyr Gly Gly Leu Gly Gln Gly Gly Tyr
1               5                   10                  15

Gly Gln Gly Ala Gly Ser Ser Ala Ala Ala Ala Ala Ala Ala Ala Ala
            20                  25                  30

Ala Ala Gly Arg Gly Gln Gly Gly Tyr Gly Gln Gly Ser Gly Gly Asn
        35                  40                  45

Ala Ala Ala Ala Ala Ala Ala Ala Ala Ala Ser Gly Gln Gly
    50                  55                  60

Gly Gln Gly Gly Gln Gly Gly Gln Gly Gly Gln Gly Tyr Gly Gln Gly
65                  70                  75                  80

Ala Gly Ser Ser Ala Ala Ala Ala Ala Ala Ala Ala Ala Ala Ala Ala
                85                  90                  95

Ala Ala Ala Gly Arg Gly Gln Gly Gly Tyr Gly Gln Gly Ala Gly Gly
            100                 105                 110

Asn Ala Ala Ala Ala Ala Ala Ala Ala Ala Ala Ser Gly Gln
        115                 120                 125

Gly Gly Gln Gly Gly Gln Gly Gly Gln Gly Gly Gly Tyr Gly Gln
    130                 135                 140

Gly Ala Gly Ser Ser Ala Ala Ala Ala Ala Ala Ala Ala Ala Ala Ala
145                 150                 155                 160

Ala Ala Ala

<210> SEQ ID NO 96
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gly Gly Tyr Gly Pro Gly Ser Gly Gln Gln Gly Pro Gly Gln Gln Gly
1               5                   10                  15

Pro Gly Gln Gln Gly Pro Gly Gln Gln Gly Pro Tyr Gly Ala Gly Ala
            20                  25                  30

Ser Ala Ala Ala Ala Ala Gly Gly Tyr Gly Pro Gly Ser Gly Gln
        35                  40                  45

Gln Gly Pro Gly Val Arg Val Ala Ala Pro Val Ala Ser Ala Ala Ala
    50                  55                  60

Ser Arg Leu Ser Ser Ala Ala Ser Ser Arg Val Ser Ser Ala Val
65                  70                  75                  80

Ser Ser Leu Val Ser Ser Gly Pro Thr Thr Pro Ala Ala Leu Ser Asn
                85                  90                  95

Thr Ile Ser Ser Ala Val Ser Gln Ile Ser Ala Ser Asn Pro Gly Leu
            100                 105                 110

Ser Gly Cys Asp Val Leu Val Gln Ala Leu Leu Glu Val Val Ser Ala
        115                 120                 125

Leu Val His Ile Leu Gly Ser Ser Ser Val Gly Gln Ile Asn Tyr Gly
    130                 135                 140
```

```
Ala Ser Ala Gln Tyr Ala Gln Met Val Gly Gln Ser Val Thr Gln Ala
145                 150                 155                 160

Leu Val

<210> SEQ ID NO 97
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gly Ala Gly Ala Gly Gly Ala Gly Tyr Gly Arg Gly Ala Gly Ala Gly
1               5                   10                  15

Ala Gly Ala Ala Ala Gly Ala Gly Ala Ala Ala Gly Ala Gly
            20                  25                  30

Ala Gly Ala Gly Gly Tyr Gly Gly Gln Gly Gly Tyr Gly Ala Gly Ala
        35                  40                  45

Gly Ala Gly Ala Ala Ala Ala Gly Ala Gly Ala Gly Ala Ala
        50                  55                  60

Gly Tyr Ser Arg Gly Gly Arg Ala Gly Ala Ala Gly Ala Gly Ala Gly
65                  70                  75                  80

Ala Ala Ala Gly Ala Gly Ala Gly Gly Tyr Gly Gly Gln Gly
                85                  90                  95

Gly Tyr Gly Ala Gly Ala Gly Ala Ala Ala Ala Gly Ala
            100                 105                 110

Gly Ser Gly Gly Ala Gly Gly Tyr Gly Arg Gly Ala Gly Ala Gly Ala
            115                 120                 125

Ala Ala Gly Ala Gly Ala Ala Gly Ala Gly Ala Gly Ala Gly Gly
        130                 135                 140

Tyr Gly Gly Gln Gly Gly Tyr Gly Ala Gly Ala Ala Ala Ala
145                 150                 155                 160

Ala

<210> SEQ ID NO 98
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gly Ala Gly Ala Gly Arg Gly Gly Tyr Gly Arg Gly Ala Gly Ala Gly
1               5                   10                  15

Gly Tyr Gly Gly Gln Gly Gly Tyr Gly Ala Gly Ala Gly Ala
            20                  25                  30

Ala Ala Ala Ala Gly Ala Gly Ala Gly Gly Tyr Gly Asp Lys Glu Ile
        35                  40                  45

Ala Cys Trp Ser Arg Cys Arg Tyr Thr Val Ala Ser Thr Thr Ser Arg
50                  55                  60

Leu Ser Ser Ala Glu Ala Ser Ser Arg Ile Ser Ser Ala Ser Thr
65                  70                  75                  80

Leu Val Ser Gly Gly Tyr Leu Asn Thr Ala Ala Leu Pro Ser Val Ile
                85                  90                  95

Ser Asp Leu Phe Ala Gln Val Gly Ala Ser Ser Pro Gly Val Ser Asp
                100                 105                 110
```

Ser Glu Val Leu Ile Gln Val Leu Glu Ile Val Ser Ser Leu Ile
        115                 120                 125

His Ile Leu Ser Ser Ser Val Gly Gln Val Asp Phe Ser Ser Val
    130                 135                 140

Gly Ser Ser Ala Ala Val Gly Gln Ser Met Gln Val Val Met Gly
145                 150                 155                 160

<210> SEQ ID NO 99
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gly Ala Gly Ala Gly Ala Gly Ala Gly Tyr Gly Arg Gly Ala
1               5                   10                  15

Gly Ala Gly Ala Gly Ala Gly Ala Gly Ala Ala Gly Gln Gly Tyr
                20                  25                  30

Gly Ser Gly Ala Gly Ala Gly Ala Gly Ala Ser Ala Gly Ala Gly
            35                  40                  45

Ser Tyr Gly Arg Gly Ala Gly Ala Gly Ala Ala Ala Ser Gly Ala
50                  55                  60

Gly Ala Gly Gly Tyr Gly Ala Gly Gln Gly Tyr Gly Ala Gly Ala
65                  70                  75                  80

Ala Val Ala Ser Ala Ala Gly Ala Gly Ser Gly Ala Gly Gly Ala
                85                  90                  95

Gly Gly Tyr Gly Arg Gly Ala Val Ala Gly Ser Gly Ala Gly Ala Gly
                100                 105                 110

Ala Gly Ala Gly Gly Ala Gly Tyr Gly Ala Gly Ala Gly Ala Gly
            115                 120                 125

Ala Ala Ala Gly Ala Val Ala Gly Gly Ser Gly Gly Tyr Gly Gly Arg
        130                 135                 140

Gln Gly Gly Tyr Ser Ala Gly Ala Gly Ala Gly Ala Ala Ala Ala
145                 150                 155                 160

<210> SEQ ID NO 100
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gly Pro Gly Gly Tyr Gly Pro Val Gln Gln Gly Pro Ser Gly Pro Gly
1               5                   10                  15

Ser Ala Ala Gly Pro Gly Gly Tyr Gly Pro Ala Gln Gln Gly Pro Ala
                20                  25                  30

Arg Tyr Gly Pro Gly Ser Ala Ala Ala Ala Ala Ala Gly Ser
            35                  40                  45

Ala Gly Tyr Gly Pro Gly Pro Gln Ala Ser Ala Ala Ser Arg Leu
50                  55                  60

Ala Ser Pro Asp Ser Gly Ala Arg Val Ala Ser Ala Val Ser Asn Leu
65                  70                  75                  80

Val Ser Ser Gly Pro Thr Ser Ser Ala Ala Leu Ser Ser Val Ile Ser
                85                  90                  95

Asn Ala Val Ser Gln Ile Gly Ala Ser Asn Pro Gly Leu Ser Gly Cys
            100                 105                 110

Asp Val Leu Ile Gln Ala Leu Leu Glu Ile Val Ser Ala Cys Val Thr
            115                 120                 125

Ile Leu Ser Ser Ser Ile Gly Gln Val Asn Tyr Gly Ala Ala Ser
130                 135                 140

Gln Phe Ala Gln Val Val Gly Gln Ser Val Leu Ser Ala Phe Ser
145                 150                 155

<210> SEQ ID NO 101
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gly Thr Gly Gly Val Gly Gly Leu Phe Leu Ser Ser Gly Asp Phe Gly
1               5                   10                  15

Arg Gly Gly Ala Gly Ala Gly Ala Gly Ala Ala Ala Ser Ala Ala
            20                  25                  30

Ala Ala Ser Ser Ala Ala Ala Gly Ala Arg Gly Gly Ser Gly Phe Gly
        35                  40                  45

Val Gly Thr Gly Gly Phe Gly Arg Gly Gly Ala Gly Ala Gly Thr Gly
    50                  55                  60

Ala Ala Ala Ala Ser Ala Ala Ala Ser Ala Ala Ala Ala Gly Ala
65                  70                  75                  80

Gly Gly Asp Gly Gly Leu Phe Leu Ser Ser Gly Asp Phe Gly Arg Gly
                85                  90                  95

Gly Ala Gly Ala Gly Ala Gly Ala Ala Ala Ser Ala Ala Ala Ala
            100                 105                 110

Ser Ser Ala Ala Ala Gly Ala Arg Gly Gly Ser Gly Phe Gly Val Gly
        115                 120                 125

Thr Gly Gly Phe Gly Arg Gly Gly Ala Gly Asp Gly Ala Ser Ala Ala
    130                 135                 140

Ala Ala Ser Ala Ala Ala Ala Ser Ala Ala Ala Ala
145                 150                 155

<210> SEQ ID NO 102
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gly Gly Tyr Gly Pro Gly Ala Gly Gln Gln Gly Pro Gly Gly Ala Gly
1               5                   10                  15

Gln Gln Gly Pro Gly Gly Gln Gly Pro Tyr Gly Pro Ser Val Ala Ala
            20                  25                  30

Ala Ala Ser Ala Ala Gly Gly Tyr Gly Pro Gly Ala Gly Gln Gln Gly
        35                  40                  45

Pro Val Ala Ser Ala Ala Val Ser Arg Leu Ser Ser Pro Gln Ala Ser
    50                  55                  60

Ser Arg Val Ser Ser Ala Val Ser Ser Leu Val Ser Ser Gly Pro Thr
65                  70                  75                  80

Asn Pro Ala Ala Leu Ser Asn Ala Met Ser Ser Val Ser Gln Val
                85                  90                  95

Ser Ala Ser Asn Pro Gly Leu Ser Gly Cys Asp Val Leu Val Gln Ala
            100                 105                 110

Leu Leu Glu Ile Val Ser Ala Leu Val His Ile Leu Gly Ser Ser Ser
        115                 120                 125

Ile Gly Gln Ile Asn Tyr Ala Ala Ser Ser Gln Tyr Ala Gln Met Val
    130                 135                 140

Gly Gln Ser Val Ala Gln Ala Leu Ala
145                 150

<210> SEQ ID NO 103
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Gly Ala Gly Gln Gly Gly Tyr Gly Gly Leu Gly Ser Gln Gly Ala
1               5                   10                  15

Gly Arg Gly Gly Tyr Gly Gly Gln Gly Ala Gly Ala Ala Ala Ala Ala
            20                  25                  30

Thr Gly Gly Ala Gly Gln Gly Gly Tyr Gly Gly Val Gly Ser Gly Ala
        35                  40                  45

Ser Ala Ala Ser Ala Ala Ala Ser Arg Leu Ser Ser Pro Gln Ala Ser
    50                  55                  60

Ser Arg Val Ser Ser Ala Val Ser Asn Leu Val Ala Ser Gly Pro Thr
65                  70                  75                  80

Asn Ser Ala Ala Leu Ser Ser Thr Ile Ser Asn Ala Val Ser Gln Ile
                85                  90                  95

Gly Ala Ser Asn Pro Gly Leu Ser Gly Cys Asp Val Leu Ile Gln Ala
            100                 105                 110

Leu Leu Glu Val Val Ser Ala Leu Ile His Ile Leu Gly Ser Ser Ser
        115                 120                 125

Ile Gly Gln Val Asn Tyr Gly Ser Ala Gly Gln Ala Thr Gln Ile Val
    130                 135                 140

Gly Gln Ser Val Tyr Gln Ala Leu Gly
145                 150

<210> SEQ ID NO 104
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gly Gly Ala Gly Gln Gly Gly Tyr Gly Gly Leu Gly Ser Gln Gly Ala
1               5                   10                  15

Gly Arg Gly Gly Tyr Gly Gly Gln Gly Ala Gly Ala Ala Val Ala Ala
            20                  25                  30

Ile Gly Gly Val Gly Gln Gly Gly Tyr Gly Gly Val Gly Ser Gly Ala
        35                  40                  45

Ser Ala Ala Ser Ala Ala Ala Ser Arg Leu Ser Ser Pro Glu Ala Ser
    50                  55                  60

```
Ser Arg Val Ser Ser Ala Val Ser Asn Leu Val Ser Ser Gly Pro Thr
 65                  70                  75                  80

Asn Ser Ala Ala Leu Ser Ser Thr Ile Ser Asn Val Val Ser Gln Ile
                 85                  90                  95

Gly Ala Ser Asn Pro Gly Leu Ser Gly Cys Asp Val Leu Ile Gln Ala
            100                 105                 110

Leu Leu Glu Val Val Ser Ala Leu Val His Ile Leu Gly Ser Ser Ser
        115                 120                 125

Ile Gly Gln Val Asn Tyr Gly Ser Ala Gly Gln Ala Thr Gln Ile Val
130                 135                 140

Gly Gln Ser Val Tyr Gln Ala Leu Gly
145                 150
```

<210> SEQ ID NO 105
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Gly Ala Ser Gly Gly Tyr Gly Gly Ala Gly Glu Gly Ala Gly Ala
1               5                   10                  15

Ala Ala Ala Ala Gly Ala Gly Ala Gly Ala Gly Tyr Gly Gly
            20                  25                  30

Gly Ala Gly Ser Gly Ala Gly Ala Val Ala Arg Ala Gly Ala Gly Gly
            35                  40                  45

Ala Gly Gly Tyr Gly Ser Gly Ile Gly Gly Tyr Gly Ser Gly Ala
        50                  55                  60

Gly Ala Ala Ala Gly Ala Gly Ala Gly Ala Gly Ala Tyr Gly Gly
 65                  70                  75                  80

Gly Tyr Gly Thr Gly Ala Gly Ala Gly Ala Arg Gly Ala Asp Ser Ala
                85                  90                  95

Gly Ala Ala Ala Gly Tyr Gly Gly Val Gly Thr Gly Thr Gly Ser
            100                 105                 110

Ser Ala Gly Tyr Gly Arg Gly Ala Gly Ala Gly Ala Gly Ala
        115                 120                 125

Ala Ala Gly Ser Gly Ala Gly Ala Ala Gly Gly Tyr Gly Gly Gly Tyr
            130                 135                 140

Gly Ala Gly Ala Gly Ala Gly Ala
145                 150
```

<210> SEQ ID NO 106
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Gly Ala Gly Ser Gly Gln Gly Gly Tyr Gly Gly Gln Gly Gly Leu Gly
1               5                   10                  15

Gly Tyr Gly Gln Gly Ala Gly Ala Gly Ala Ala Ala Gly Ala Ser Gly
            20                  25                  30

Ser Gly Ser Gly Gly Ala Gly Gln Gly Gly Leu Gly Gly Tyr Gly Gln
        35                  40                  45
```

```
Gly Ala Gly Ala Gly Ala Ala Ala Ala Gly Ala Ser Gly Ala
        50                  55                  60

Gly Gln Gly Gly Phe Gly Pro Tyr Gly Ser Ser Tyr Gln Ser Ser Thr
65                  70                  75                  80

Ser Tyr Ser Val Thr Ser Gln Gly Ala Ala Gly Gly Leu Gly Gly Tyr
                85                  90                  95

Gly Gln Gly Ser Gly Ala Gly Ala Ala Ala Gly Ala Ala Gly Gln
            100                 105                 110

Gly Gly Gln Gly Gly Tyr Gly Gln Gly Ala Gly Ala Gly Ala Gly Ala
            115                 120                 125

Gly Ala Gly Gln Gly Gly Leu Gly Gly Tyr Gly Gln Gly Ala Gly Ser
        130                 135                 140

Ser Ala Ala Ser Ala Ala Ala Ala
145                 150
```

<210> SEQ ID NO 107
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Gly Gly Ala Gly Gln Gly Gly Tyr Gly Gly Leu Gly Gly Gln Gly Val
1               5                   10                  15

Gly Arg Gly Gly Leu Gly Gly Gln Gly Ala Gly Ala Ala Ala Ala Gly
            20                  25                  30

Gly Ala Gly Gln Gly Gly Tyr Gly Gly Val Gly Ser Gly Ala Ser Ala
        35                  40                  45

Ala Ser Ala Ala Ala Ser Arg Leu Ser Ser Pro Gln Ala Ser Ser Arg
    50                  55                  60

Leu Ser Ser Ala Val Ser Asn Leu Val Ala Thr Gly Pro Thr Asn Ser
65                  70                  75                  80

Ala Ala Leu Ser Ser Thr Ile Ser Asn Val Val Ser Gln Ile Gly Ala
                85                  90                  95

Ser Asn Pro Gly Leu Ser Gly Cys Asp Val Leu Ile Gln Ala Leu Leu
            100                 105                 110

Glu Val Val Ser Ala Leu Ile Gln Ile Leu Gly Ser Ser Ser Ile Gly
            115                 120                 125

Gln Val Asn Tyr Gly Ser Ala Gly Gln Ala Thr Gln Ile Val Gly Gln
        130                 135                 140

Ser Val Tyr Gln Ala Leu Gly
145                 150
```

<210> SEQ ID NO 108
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Gly Ala Gly Ser Gly Gly Ala Gly Gly Tyr Gly Arg Gly Ala Gly Ala
1               5                   10                  15

Gly Ala Gly Ala Ala Ala Gly Ala Gly Ala Gly Ala Gly Ser Tyr Gly
            20                  25                  30
```

```
Gly Gln Gly Gly Tyr Gly Ala Gly Ala Gly Ala Ala Ala Ala
        35                  40                  45

Ala Gly Ala Gly Ala Gly Gly Tyr Gly Arg Gly Ala Gly Ala
    50                  55                  60

Gly Ala Gly Ala Gly Ala Ala Ala Arg Ala Gly Ala Gly Ala
65                  70                  75                  80

Gly Gly Ala Gly Tyr Gly Gly Gln Gly Gly Tyr Gly Ala Gly Ala Gly
                85                  90                  95

Ala Gly Ala Ala Ala Ala Gly Ala Gly Ala Gly Ala Gly Gly
        100                 105                 110

Tyr Gly Arg Gly Ala Gly Ala Gly Ala Gly Ala Ala Gly Ala Gly
            115                 120                 125

Ala Gly Ala Gly Gly Tyr Gly Gly Gln Ser Gly Tyr Gly Ala Gly Ala
    130                 135                 140

Gly Ala Ala Ala Ala Ala
145                 150

<210> SEQ ID NO 109
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gly Ala Ser Gly Ala Gly Gln Gly Gln Gly Tyr Gly Gln Gln Gly Gln
1               5                   10                  15

Gly Gly Ser Ser Ala Ala Ala Ala Ala Ala Ala Ala Ala Gln
        20                  25                  30

Gly Gln Gly Gln Gly Tyr Gly Gln Gln Gly Gln Gly Tyr Gly Gln Gln
        35                  40                  45

Gly Gln Gly Gly Ser Ser Ala Ala Ala Ala Ala Ala Ala Ala
        50                  55                  60

Ala Ala Ala Gln Gly Gln Gly Gln Gly Tyr Gly Gln Gln Gly Gln Gly
65                  70                  75                  80

Ser Ala Ala Ala Ala Ala Ala Ala Gly Ala Ser Gly Ala Gly
                85                  90                  95

Gln Gly Gln Gly Tyr Gly Gln Gln Gly Gln Gly Ser Ser Ala Ala
        100                 105                 110

Ala Ala Ala Ala Ala Ala Ala Ala Ala Ala Gln Gly Gln
            115                 120                 125

Gly Tyr Gly Gln Gln Gly Gln Gly Ser Ala Ala Ala Ala Ala
        130                 135                 140

Ala Ala Ala Ala Ala Ala
145                 150

<210> SEQ ID NO 110
<211> LENGTH: 945
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gly Gly Tyr Gly Pro Gly Ala Gly Gln Gln Gly Pro Gly Ser Gly Gly
1               5                   10                  15
```

```
Gln Gln Gly Pro Gly Gly Gln Gly Pro Tyr Gly Ser Gly Gln Gln Gly
            20                  25                  30

Pro Gly Gly Ala Gly Gln Gln Gly Pro Gly Gln Gly Pro Tyr Gly
        35                  40                  45

Pro Gly Ala Ala Ala Ala Ala Ala Ala Gly Gly Tyr Gly Pro
    50                  55                  60

Gly Ala Gly Gln Gln Gly Pro Gly Ala Gly Gln Gln Gly Pro Gly
65                  70                  75                  80

Ser Gln Gly Pro Gly Gly Gln Gly Pro Tyr Gly Pro Gly Ala Gly Gln
                85                  90                  95

Gln Gly Pro Gly Ser Gln Gly Pro Gly Ser Gly Gly Gln Gly Pro
            100                 105                 110

Gly Gly Gln Gly Pro Tyr Gly Pro Ser Ala Ala Ala Ala Ala Ala
            115                 120                 125

Ala Ala Gly Gly Tyr Gly Pro Gly Ala Gly Gln Arg Ser Gln Gly Pro
130                 135                 140

Gly Gly Gln Gly Pro Tyr Gly Pro Gly Ala Gly Gln Gln Gly Pro Gly
145                 150                 155                 160

Ser Gln Gly Pro Gly Ser Gly Gln Gln Gly Pro Gly Gln Gly
                165                 170                 175

Pro Tyr Gly Pro Ser Ala Ala Ala Ala Ala Ala Ala Gly Gly Tyr
            180                 185                 190

Gly Pro Gly Ala Gly Gln Gln Gly Pro Gly Ser Gln Gly Pro Gly Ser
        195                 200                 205

Gly Gly Gln Gln Gly Pro Gly Gly Gln Gly Pro Tyr Gly Pro Gly Ala
210                 215                 220

Ala Ala Ala Ala Ala Val Gly Gly Tyr Gly Pro Gly Ala Gly Gln
225                 230                 235                 240

Gln Gly Pro Gly Ser Gln Gly Pro Gly Ser Gly Gly Gln Gln Gly Pro
            245                 250                 255

Gly Gly Gln Gly Pro Tyr Gly Pro Ser Ala Ala Ala Ala Ala Ala
            260                 265                 270

Ala Gly Gly Tyr Gly Pro Gly Ala Gly Gln Gln Gly Pro Gly Ser Gln
        275                 280                 285

Gly Pro Gly Ser Gly Gly Gln Gln Gly Pro Gly Gly Gln Gly Pro Tyr
        290                 295                 300

Gly Pro Ser Ala Ala Ala Ala Ala Ala Ala Gly Gly Tyr Gly Pro
305                 310                 315                 320

Gly Ala Gly Gln Gln Gly Pro Gly Ser Gly Gln Gln Gly Pro Gly
            325                 330                 335

Gly Gln Gly Pro Tyr Gly Ser Gly Gln Gln Gly Pro Gly Gly Ala Gly
            340                 345                 350

Gln Gln Gly Pro Gly Gly Gln Gly Pro Tyr Gly Pro Gly Ala Ala Ala
            355                 360                 365

Ala Ala Ala Ala Ala Gly Gly Tyr Gly Pro Gly Ala Gly Gln Gln
            370                 375                 380

Gly Pro Gly Gly Ala Gly Gln Gln Gly Pro Gly Ser Gln Gly Pro Gly
385                 390                 395                 400

Gly Gln Gly Pro Tyr Gly Pro Gly Ala Gly Gln Gln Gly Pro Gly Ser
                405                 410                 415

Gln Gly Pro Gly Ser Gly Gly Gln Gly Pro Gly Gln Gly Pro
            420                 425                 430
```

-continued

```
Tyr Gly Pro Ser Ala Ala Ala Ala Ala Ala Ala Gly Gly Tyr
        435                 440                 445

Gly Pro Gly Ala Gly Gln Arg Ser Gln Gly Pro Gly Gly Gln Gly Pro
    450                 455                 460

Tyr Gly Pro Gly Ala Gly Gln Gln Gly Pro Gly Ser Gln Gly Pro Gly
465                 470                 475                 480

Ser Gly Gly Gln Gln Gly Pro Gly Gly Gln Gly Pro Tyr Gly Pro Ser
                485                 490                 495

Ala Ala Ala Ala Ala Ala Ala Gly Gly Tyr Gly Pro Gly Ala Gly
            500                 505                 510

Gln Gln Gly Pro Gly Ser Gln Gly Pro Gly Ser Gly Gly Gln Gln Gly
            515                 520                 525

Pro Gly Gly Gln Gly Pro Tyr Gly Pro Gly Ala Ala Ala Ala Ala
    530                 535                 540

Ala Val Gly Gly Tyr Gly Pro Gly Ala Gly Gln Gln Gly Pro Gly Ser
545                 550                 555                 560

Gln Gly Pro Gly Ser Gly Gly Gln Gln Gly Pro Gly Gly Gln Gly Pro
                565                 570                 575

Tyr Gly Pro Ser Ala Ala Ala Ala Ala Ala Ala Gly Gly Tyr Gly
            580                 585                 590

Pro Gly Ala Gly Gln Gln Gly Pro Gly Ser Gln Gly Pro Gly Ser Gly
    595                 600                 605

Gly Gln Gln Gly Pro Gly Gly Gln Gly Pro Tyr Gly Pro Ser Ala Ala
            610                 615                 620

Ala Ala Ala Ala Ala Ala Gly Gly Tyr Gly Pro Gly Ala Gly Gln Gln
625                 630                 635                 640

Gly Pro Gly Ser Gly Gly Gln Gln Gly Pro Gly Gly Gln Gly Pro Tyr
                645                 650                 655

Gly Ser Gly Gln Gln Gly Pro Gly Ala Gly Gln Gln Gly Pro Gly
            660                 665                 670

Gly Gln Gly Pro Tyr Gly Pro Gly Ala Ala Ala Ala Ala Ala Ala
    675                 680                 685

Ala Gly Gly Tyr Gly Pro Gly Ala Gly Gln Gln Gly Pro Gly Gly Ala
690                 695                 700

Gly Gln Gln Gly Pro Gly Ser Gln Gly Pro Gly Gly Gln Gly Pro Tyr
705                 710                 715                 720

Gly Pro Gly Ala Gly Gln Gln Gly Pro Gly Ser Gln Gly Pro Gly Ser
                725                 730                 735

Gly Gly Gln Gln Gly Pro Gly Gly Gln Gly Pro Tyr Gly Pro Ser Ala
            740                 745                 750

Ala Ala Ala Ala Ala Ala Ala Gly Gly Tyr Gly Pro Gly Ala Gly
            755                 760                 765

Gln Arg Ser Gln Gly Pro Gly Gly Gln Gly Pro Tyr Gly Pro Gly Ala
    770                 775                 780

Gly Gln Gln Gly Pro Gly Ser Gln Gly Pro Gly Ser Gly Gly Gln Gln
785                 790                 795                 800

Gly Pro Gly Gly Gln Gly Pro Tyr Gly Pro Ser Ala Ala Ala Ala
                805                 810                 815

Ala Ala Ala Gly Gly Tyr Gly Pro Gly Ala Gly Gln Gln Gly Pro Gly
            820                 825                 830

Ser Gln Gly Pro Gly Ser Gly Gly Gln Gln Gly Pro Gly Gly Gln Gly
    835                 840                 845

Pro Tyr Gly Pro Gly Ala Ala Ala Ala Ala Ala Ala Val Gly Gly Tyr
```

```
                    850                 855                 860
Gly Pro Gly Ala Gly Gln Gln Gly Pro Gly Ser Gln Gly Pro Gly Ser
865                 870                 875                 880

Gly Gly Gln Gln Gly Pro Gly Gln Gly Pro Tyr Gly Pro Ser Ala
                885                 890                 895

Ala Ala Ala Ala Ala Ala Gly Gly Tyr Gly Pro Gly Ala Gly Gln
                900                 905                 910

Gln Gly Pro Gly Ser Gln Gly Pro Gly Ser Gly Gln Gln Gly Pro
            915                 920                 925

Gly Gly Gln Gly Pro Tyr Gly Pro Ser Ala Ala Ala Ala Ala Ala
            930                 935                 940

Ala
945

<210> SEQ ID NO 111
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Asp Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Asn Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Thr Ser Gly Glu Gln Arg Ile Lys Ala Trp Thr His Phe Gln Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Val Asn Gly Asn
            180                 185                 190

Tyr Asp Tyr Leu Met Tyr Ala Asp Ile Asp Tyr Asp His Pro Asp Ala
        195                 200                 205

Thr Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255
```

```
Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Tyr Asp Met
290                 295                 300

Arg Lys Leu Leu Asn Gly Thr Val Val Ser Lys His Pro Val Lys Ala
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ala Gly Tyr Pro Gln Ile Phe Tyr Gly Asp Met Tyr Gly
            355                 360                 365

Thr Lys Gly Ala Ser Gln Arg Glu Ile Pro Ala Leu Lys His Lys Ile
        370                 375                 380

Glu Pro Ile Leu Lys Ala Arg Ile Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Thr Lys Arg Met Tyr Val Gly Arg Gln Asn Ala Gly Glu Thr
        435                 440                 445

Trp His Asp Ile Thr Gly Asn Arg Ser Asp Ser Val Val Ile Asn Ala
450                 455                 460

Glu Gly Trp Gly Glu Phe His Val Asn Gly Gly Ser Val Ser Ile Tyr
465                 470                 475                 480

Val Gln Arg

<210> SEQ ID NO 112
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Thr Ala Leu Thr Glu Gly Ala Lys Leu Phe Glu Lys Glu Ile Pro Tyr
1               5                   10                  15

Ile Thr Glu Leu Glu Gly Asp Val Glu Gly Met Lys Phe Ile Ile Lys
            20                  25                  30

Gly Glu Gly Thr Gly Asp Ala Thr Thr Gly Thr Ile Lys Ala Lys Tyr
        35                  40                  45

Ile Cys Thr Thr Gly Asp Leu Pro Val Pro Trp Ala Thr Leu Val Ser
50                  55                  60

Thr Leu Ser Tyr Gly Val Gln Cys Phe Ala Lys Tyr Pro Ser His Ile
65                  70                  75                  80

Lys Asp Phe Phe Lys Ser Ala Met Pro Glu Gly Tyr Thr Gln Glu Arg
                85                  90                  95

Thr Ile Ser Phe Glu Gly Asp Gly Val Tyr Lys Thr Arg Ala Met Val
            100                 105                 110

Thr Tyr Glu Arg Gly Ser Ile Tyr Asn Arg Val Thr Leu Thr Gly Glu
        115                 120                 125
```

```
Asn Phe Lys Lys Asp Gly His Ile Leu Arg Lys Asn Val Ala Phe Gln
            130                 135                 140

Cys Pro Pro Ser Ile Leu Tyr Ile Leu Pro Asp Thr Val Asn Asn Gly
145                 150                 155                 160

Ile Arg Val Glu Phe Asn Gln Ala Tyr Asp Ile Glu Gly Val Thr Glu
                165                 170                 175

Lys Leu Val Thr Lys Cys Ser Gln Met Asn Arg Pro Leu Ala Gly Ser
            180                 185                 190

Ala Ala Val His Ile Pro Arg Tyr His His Ile Thr Tyr His Thr Lys
        195                 200                 205

Leu Ser Lys Asp Arg Asp Glu Arg Arg Asp His Met Cys Leu Val Glu
210                 215                 220

Val Val Lys Ala Val Asp Leu Asp Thr Tyr Gln
225                 230                 235

<210> SEQ ID NO 113
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(64)
<223> OTHER INFORMATION: This region may encompass 4-8 "GPG-X1"
      repeating units, wherein X1 is "SGGQQ," "GAGQQ," "GQGPY," "AGQQ"
      or "SQ," and some positions may be absent
<220> FEATURE:
<221> NAME/KEY: MISC_FEATURE
<222> LOCATION: (4)..(8)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (12)..(16)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (20)..(24)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (28)..(32)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (36)..(40)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (44)..(48)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (52)..(56)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (60)..(64)
<223> OTHER INFORMATION: This region may encompass "SGGQQ," "GAGQQ,"
      "GQGPY," "AGQQ" or "SQ," wherein some positions may be absent

<400> SEQUENCE: 113

Gly Pro Gly Xaa Xaa Xaa Xaa Xaa Gly Pro Gly Xaa Xaa Xaa Xaa Xaa
```

```
                1               5                  10                 15
Gly Pro Gly Xaa Xaa Xaa Xaa Gly Pro Gly Xaa Xaa Xaa Xaa Xaa
                20                 25                 30

Gly Pro Gly Xaa Xaa Xaa Xaa Gly Pro Gly Xaa Xaa Xaa Xaa Xaa
                35                 40                 45

Gly Pro Gly Xaa Xaa Xaa Xaa Gly Pro Gly Xaa Xaa Xaa Xaa Xaa
                50                 55                 60
```

<210> SEQ ID NO 114
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 6-20 residues

<400> SEQUENCE: 114

```
Ala Ala Ala Ala Ala Ala Ala Ala Ala Ala Ala Ala Ala Ala Ala
1               5                  10                 15

Ala Ala Ala Ala
                20
```

<210> SEQ ID NO 115
<211> LENGTH: 1800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1800)
<223> OTHER INFORMATION: This sequence may encompass 2-20
      "GGY-[GPG-X1]n1-GPS-(A)n2" repeating units, wherein X1 is "SGGQQ,"
      "GAGQQ," "GQGPY," "AGQQ" or "SQ," n1 is 4-8 and n2 is 6-20 and
      some positions may be absent
<220> FEATURE:
<221> NAME/KEY: MISC_FEATURE
<222> LOCATION: (4)..(67)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:

-continued

```
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (71)..(90)
<223> OTHER INFORMATION: This region may encompass 6-20 residues
<220> FEATURE:
<221> NAME/KEY: MISC_FEATURE
<222> LOCATION: (94)..(157)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (97)..(101)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (105)..(109)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (113)..(117)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (121)..(125)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (129)..(133)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (137)..(141)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (145)..(149)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (153)..(157)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (161)..(180)
<223> OTHER INFORMATION: This region may encompass 6-20 residues
<220> FEATURE:
<221> NAME/KEY: MISC_FEATURE
<222> LOCATION: (184)..(247)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (187)..(191)
<223> OTHER INFORMATION: This region may encompass "SGGQQ," "GAGQQ,"
      "GQGPY," "AGQQ" or "SQ," wherein some positions may be absent
```

```
<220> FEATURE:
<221> NAME/KEY: MISC_FEATURE
<222> LOCATION: (195)..(199)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (203)..(207)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (211)..(215)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (219)..(223)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (227)..(231)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (235)..(239)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (243)..(247)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (251)..(270)
<223> OTHER INFORMATION: This region may encompass 6-20 residues
<220> FEATURE:
<221> NAME/KEY: MISC_FEATURE
<222> LOCATION: (274)..(337)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (277)..(281)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (285)..(289)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (293)..(297)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (301)..(305)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (309)..(313)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (317)..(321)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (325)..(329)
<223> OTHER INFORMATION: This region may encompass "SGGQQ," "GAGQQ,"
```

```
      "GQGPY," "AGQQ" or "SQ," wherein some positions may be absent
<220> FEATURE:
<221> NAME/KEY: MISC_FEATURE
<222> LOCATION: (333)..(337)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (341)..(360)
<223> OTHER INFORMATION: This region may encompass 6-20 residues
<220> FEATURE:
<221> NAME/KEY: MISC_FEATURE
<222> LOCATION: (364)..(427)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (367)..(371)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (375)..(379)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (383)..(387)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (391)..(395)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (399)..(403)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (407)..(411)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (415)..(419)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (423)..(427)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (431)..(450)
<223> OTHER INFORMATION: This region may encompass 6-20 residues
<220> FEATURE:
<221> NAME/KEY: MISC_FEATURE
<222> LOCATION: (454)..(517)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (457)..(461)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (465)..(469)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (473)..(477)
```

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (481)..(485)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (489)..(493)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (497)..(501)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (505)..(509)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (513)..(517)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (521)..(540)
<223> OTHER INFORMATION: This region may encompass 6-20 residues
<220> FEATURE:
<221> NAME/KEY: MISC_FEATURE
<222> LOCATION: (544)..(607)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (547)..(551)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (555)..(559)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (563)..(567)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (571)..(575)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (579)..(583)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (587)..(591)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (595)..(599)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (603)..(607)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

```
<222> LOCATION: (611)..(630)
<223> OTHER INFORMATION: This region may encompass 6-20 residues
<220> FEATURE:
<221> NAME/KEY: MISC_FEATURE
<222> LOCATION: (634)..(697)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (637)..(641)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (645)..(649)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (653)..(657)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (661)..(665)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (669)..(673)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (677)..(681)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (685)..(689)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (693)..(697)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (701)..(720)
<223> OTHER INFORMATION: This region may encompass 6-20 residues
<220> FEATURE:
<221> NAME/KEY: MISC_FEATURE
<222> LOCATION: (724)..(787)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (727)..(731)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (735)..(739)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (743)..(747)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (751)..(755)
<223> OTHER INFORMATION: This region may encompass "SGGQQ," "GAGQQ,"
      "GQGPY," "AGQQ" or "SQ," wherein some positions may be absent
<220> FEATURE:
```

-continued

```
<221> NAME/KEY: MISC_FEATURE
<222> LOCATION: (759)..(763)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (767)..(771)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (775)..(779)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (783)..(787)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (791)..(810)
<223> OTHER INFORMATION: This region may encompass 6-20 residues
<220> FEATURE:
<221> NAME/KEY: MISC_FEATURE
<222> LOCATION: (814)..(877)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (817)..(821)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (825)..(829)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (833)..(837)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (841)..(845)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (849)..(853)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (857)..(861)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (865)..(869)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (873)..(877)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (881)..(900)
<223> OTHER INFORMATION: This region may encompass 6-20 residues
<220> FEATURE:
<221> NAME/KEY: MISC_FEATURE
<222> LOCATION: (904)..(967)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
```

```
<220> FEATURE:
<221> NAME/KEY: MISC_FEATURE
<222> LOCATION: (907)..(911)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (915)..(919)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (923)..(927)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (931)..(935)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (939)..(943)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (947)..(951)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (955)..(959)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (963)..(967)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (971)..(990)
<223> OTHER INFORMATION: This region may encompass 6-20 residues
<220> FEATURE:
<221> NAME/KEY: MISC_FEATURE
<222> LOCATION: (994)..(1057)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (997)..(1001)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1005)..(1009)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1013)..(1017)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1021)..(1025)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1029)..(1033)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1037)..(1041)
<223> OTHER INFORMATION: This region may encompass "SGGQQ," "GAGQQ,"
```

-continued

```
      "GQGPY," "AGQQ" or "SQ," wherein some positions may be absent
<220> FEATURE:
<221> NAME/KEY: MISC_FEATURE
<222> LOCATION: (1045)..(1049)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1053)..(1057)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1061)..(1080)
<223> OTHER INFORMATION: This region may encompass 6-20 residues
<220> FEATURE:
<221> NAME/KEY: MISC_FEATURE
<222> LOCATION: (1084)..(1147)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (1087)..(1091)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1095)..(1099)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1103)..(1107)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1111)..(1115)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1119)..(1123)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1127)..(1131)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1135)..(1139)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1143)..(1147)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1151)..(1170)
<223> OTHER INFORMATION: This region may encompass 6-20 residues
<220> FEATURE:
<221> NAME/KEY: MISC_FEATURE
<222> LOCATION: (1174)..(1237)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (1177)..(1181)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1185)..(1189)
```

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1193)..(1197)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1201)..(1205)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1209)..(1213)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1217)..(1221)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1225)..(1229)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1233)..(1237)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1241)..(1260)
<223> OTHER INFORMATION: This region may encompass 6-20 residues
<220> FEATURE:
<221> NAME/KEY: MISC_FEATURE
<222> LOCATION: (1264)..(1327)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (1267)..(1271)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1275)..(1279)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1283)..(1287)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1291)..(1295)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1299)..(1303)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1307)..(1311)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1315)..(1319)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

-continued

```
<222> LOCATION: (1323)..(1327)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1331)..(1350)
<223> OTHER INFORMATION: This region may encompass 6-20 residues
<220> FEATURE:
<221> NAME/KEY: MISC_FEATURE
<222> LOCATION: (1354)..(1417)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (1357)..(1361)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1365)..(1369)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1373)..(1377)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1381)..(1385)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1389)..(1393)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1397)..(1401)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1405)..(1409)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1413)..(1417)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1421)..(1440)
<223> OTHER INFORMATION: This region may encompass 6-20 residues
<220> FEATURE:
<221> NAME/KEY: MISC_FEATURE
<222> LOCATION: (1444)..(1507)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (1447)..(1451)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1455)..(1459)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1463)..(1467)
<223> OTHER INFORMATION: This region may encompass "SGGQQ," "GAGQQ,"
      "GQGPY," "AGQQ" or "SQ," wherein some positions may be absent
<220> FEATURE:
```

```
<221> NAME/KEY: MISC_FEATURE
<222> LOCATION: (1471)..(1475)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1479)..(1483)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1487)..(1491)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1495)..(1499)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1503)..(1507)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1511)..(1530)
<223> OTHER INFORMATION: This region may encompass 6-20 residues
<220> FEATURE:
<221> NAME/KEY: MISC_FEATURE
<222> LOCATION: (1534)..(1597)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (1537)..(1541)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1545)..(1549)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1553)..(1557)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1561)..(1565)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1569)..(1573)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1577)..(1581)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1585)..(1589)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1593)..(1597)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1601)..(1620)
<223> OTHER INFORMATION: This region may encompass 6-20 residues
<220> FEATURE:
```

-continued

```
<221> NAME/KEY: MISC_FEATURE
<222> LOCATION: (1624)..(1687)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (1627)..(1631)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1635)..(1639)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1643)..(1647)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1651)..(1655)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1659)..(1663)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1667)..(1671)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1675)..(1679)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1683)..(1687)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1691)..(1710)
<223> OTHER INFORMATION: This region may encompass 6-20 residues
<220> FEATURE:
<221> NAME/KEY: MISC_FEATURE
<222> LOCATION: (1714)..(1777)
<223> OTHER INFORMATION: This region may encompass 4-8 repeating
      "GPG-X1" repeating units, wherein X1 is "SGGQQ," "GAGQQ," "GQGPY,"
      "AGQQ" or "SQ," and some positions may be absent
<220> FEATURE:
<221> NAME/KEY: MISC_FEATURE
<222> LOCATION: (1717)..(1721)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1725)..(1729)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1733)..(1737)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1741)..(1745)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1749)..(1753)
<223> OTHER INFORMATION: This region may encompass "SGGQQ," "GAGQQ,"
```

-continued

"GQGPY," "AGQQ" or "SQ," wherein some positions may be absent
<220> FEATURE:
<221> NAME/KEY: MISC_FEATURE
<222> LOCATION: (1757)..(1761)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1765)..(1769)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1773)..(1777)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1781)..(1800)
<223> OTHER INFORMATION: This region may encompass 6-20 residues

<400> SEQUENCE: 115

Gly Gly Tyr Gly Pro Gly Xaa Xaa Xaa Xaa Gly Pro Gly Xaa Xaa
1               5                   10                  15

Xaa Xaa Xaa Gly Pro Gly Xaa Xaa Xaa Xaa Gly Pro Gly Xaa Xaa
            20                  25                  30

Xaa Xaa Xaa Gly Pro Gly Xaa Xaa Xaa Xaa Gly Pro Gly Xaa Xaa
        35                  40                  45

Xaa Xaa Xaa Gly Pro Gly Xaa Xaa Xaa Xaa Gly Pro Gly Xaa Xaa
    50                  55                  60

Xaa Xaa Xaa Gly Pro Ser Ala Ala Ala Ala Ala Ala Ala Ala Ala
65                  70                  75                  80

Ala Ala Ala Ala Ala Ala Ala Ala Ala Gly Gly Tyr Gly Pro Gly
                85                  90                  95

Xaa Xaa Xaa Xaa Xaa Gly Pro Gly Xaa Xaa Xaa Xaa Gly Pro Gly
            100                 105                 110

Xaa Xaa Xaa Xaa Xaa Gly Pro Gly Xaa Xaa Xaa Xaa Gly Pro Gly
        115                 120                 125

Xaa Xaa Xaa Xaa Xaa Gly Pro Gly Xaa Xaa Xaa Xaa Gly Pro Gly
    130                 135                 140

Xaa Xaa Xaa Xaa Xaa Gly Pro Gly Xaa Xaa Xaa Xaa Gly Pro Ser
145                 150                 155                 160

Ala Ala Ala Ala Ala Ala Ala Ala Ala Ala Ala Ala Ala Ala Ala
                165                 170                 175

Ala Ala Ala Ala Gly Gly Tyr Gly Pro Gly Xaa Xaa Xaa Xaa Gly
            180                 185                 190

Pro Gly Xaa Xaa Xaa Xaa Xaa Gly Pro Gly Xaa Xaa Xaa Xaa Gly
        195                 200                 205

Pro Gly Xaa Xaa Xaa Xaa Xaa Gly Pro Gly Xaa Xaa Xaa Xaa Gly
    210                 215                 220

Pro Gly Xaa Xaa Xaa Xaa Xaa Gly Pro Gly Xaa Xaa Xaa Xaa Gly
225                 230                 235                 240

Pro Gly Xaa Xaa Xaa Xaa Xaa Gly Pro Ser Ala Ala Ala Ala Ala
                245                 250                 255

Ala Ala Ala Ala Ala Ala Ala Ala Ala Ala Ala Ala Gly Gly
            260                 265                 270

Tyr Gly Pro Gly Xaa Xaa Xaa Xaa Gly Pro Gly Xaa Xaa Xaa Xaa
        275                 280                 285

Xaa Gly Pro Gly Xaa Xaa Xaa Xaa Gly Pro Gly Xaa Xaa Xaa Xaa
    290                 295                 300

```
Xaa Gly Pro Gly Xaa Xaa Xaa Xaa Gly Pro Gly Xaa Xaa Xaa Xaa
305                 310                 315                 320

Xaa Gly Pro Gly Xaa Xaa Xaa Xaa Gly Pro Gly Xaa Xaa Xaa Xaa
                325                 330                 335

Xaa Gly Pro Ser Ala Ala Ala Ala Ala Ala Ala Ala Ala Ala Ala
            340                 345                 350

Ala Ala Ala Ala Ala Ala Ala Gly Gly Tyr Gly Pro Gly Xaa Xaa
        355                 360                 365

Xaa Xaa Xaa Gly Pro Gly Xaa Xaa Xaa Xaa Gly Pro Gly Xaa Xaa
    370                 375                 380

Xaa Xaa Xaa Gly Pro Gly Xaa Xaa Xaa Xaa Gly Pro Gly Xaa Xaa
385                 390                 395                 400

Xaa Xaa Xaa Gly Pro Gly Xaa Xaa Xaa Xaa Gly Pro Gly Xaa Xaa
                405                 410                 415

Xaa Xaa Xaa Gly Pro Gly Xaa Xaa Xaa Xaa Gly Pro Ser Ala Ala
            420                 425                 430

Ala Ala Ala Ala Ala Ala Ala Ala Ala Ala Ala Ala Ala Ala Ala
        435                 440                 445

Ala Ala Gly Gly Tyr Gly Pro Gly Xaa Xaa Xaa Xaa Gly Pro Gly
    450                 455                 460

Xaa Xaa Xaa Xaa Xaa Gly Pro Gly Xaa Xaa Xaa Xaa Gly Pro Gly
465                 470                 475                 480

Xaa Xaa Xaa Xaa Xaa Gly Pro Gly Xaa Xaa Xaa Xaa Gly Pro Gly
                485                 490                 495

Xaa Xaa Xaa Xaa Xaa Gly Pro Gly Xaa Xaa Xaa Xaa Gly Pro Gly
            500                 505                 510

Xaa Xaa Xaa Xaa Xaa Gly Pro Ser Ala Ala Ala Ala Ala Ala Ala
        515                 520                 525

Ala Ala Ala Ala Ala Ala Ala Ala Ala Ala Gly Gly Tyr Gly
    530                 535                 540

Pro Gly Xaa Xaa Xaa Xaa Xaa Gly Pro Gly Xaa Xaa Xaa Xaa Gly
545                 550                 555                 560

Pro Gly Xaa Xaa Xaa Xaa Xaa Gly Pro Gly Xaa Xaa Xaa Xaa Gly
                565                 570                 575

Pro Gly Xaa Xaa Xaa Xaa Xaa Gly Pro Gly Xaa Xaa Xaa Xaa Gly
            580                 585                 590

Pro Gly Xaa Xaa Xaa Xaa Xaa Gly Pro Gly Xaa Xaa Xaa Xaa Gly
        595                 600                 605

Pro Ser Ala Ala Ala Ala Ala Ala Ala Ala Ala Ala Ala Ala
    610                 615                 620

Ala Ala Ala Ala Ala Ala Gly Gly Tyr Gly Pro Gly Xaa Xaa Xaa
625                 630                 635                 640

Xaa Gly Pro Gly Xaa Xaa Xaa Xaa Gly Pro Gly Xaa Xaa Xaa Xaa
                645                 650                 655

Xaa Gly Pro Gly Xaa Xaa Xaa Xaa Gly Pro Gly Xaa Xaa Xaa Xaa
            660                 665                 670

Xaa Gly Pro Gly Xaa Xaa Xaa Xaa Gly Pro Gly Xaa Xaa Xaa Xaa
        675                 680                 685

Xaa Gly Pro Gly Xaa Xaa Xaa Xaa Xaa Gly Pro Ser Ala Ala Ala
    690                 695                 700

Ala Ala Ala Ala Ala Ala Ala Ala Ala Ala Ala Ala Ala Ala Ala
705                 710                 715                 720
```

-continued

```
Gly Gly Tyr Gly Pro Gly Xaa Xaa Xaa Xaa Gly Pro Gly Xaa Xaa
            725                 730                 735

Xaa Xaa Xaa Gly Pro Gly Xaa Xaa Xaa Xaa Gly Pro Gly Xaa Xaa
            740                 745                 750

Xaa Xaa Xaa Gly Pro Gly Xaa Xaa Xaa Xaa Gly Pro Gly Xaa Xaa
            755                 760                 765

Xaa Xaa Xaa Gly Pro Gly Xaa Xaa Xaa Xaa Gly Pro Gly Xaa Xaa
            770                 775                 780

Xaa Xaa Xaa Gly Pro Ser Ala Ala Ala Ala Ala Ala Ala Ala Ala
785                 790                 795                 800

Ala Ala Ala Ala Ala Ala Ala Ala Ala Gly Gly Tyr Gly Pro Gly
            805                 810                 815

Xaa Xaa Xaa Xaa Xaa Gly Pro Gly Xaa Xaa Xaa Xaa Gly Pro Gly
            820                 825                 830

Xaa Xaa Xaa Xaa Xaa Gly Pro Gly Xaa Xaa Xaa Xaa Gly Pro Gly
            835                 840                 845

Xaa Xaa Xaa Xaa Xaa Gly Pro Gly Xaa Xaa Xaa Xaa Gly Pro Gly
            850                 855                 860

Xaa Xaa Xaa Xaa Xaa Gly Pro Gly Xaa Xaa Xaa Xaa Gly Pro Ser
865                 870                 875                 880

Ala Ala Ala Ala Ala Ala Ala Ala Ala Ala Ala Ala Ala Ala Ala
            885                 890                 895

Ala Ala Ala Ala Gly Gly Tyr Gly Pro Gly Xaa Xaa Xaa Xaa Gly
            900                 905                 910

Pro Gly Xaa Xaa Xaa Xaa Xaa Gly Pro Gly Xaa Xaa Xaa Xaa Gly
            915                 920                 925

Pro Gly Xaa Xaa Xaa Xaa Xaa Gly Pro Gly Xaa Xaa Xaa Xaa Gly
            930                 935                 940

Pro Gly Xaa Xaa Xaa Xaa Xaa Gly Pro Gly Xaa Xaa Xaa Xaa Gly
945                 950                 955                 960

Pro Gly Xaa Xaa Xaa Xaa Xaa Gly Pro Ser Ala Ala Ala Ala Ala
            965                 970                 975

Ala Ala Ala Ala Ala Ala Ala Ala Ala Ala Ala Ala Ala Gly Gly
            980                 985                 990

Tyr Gly Pro Gly Xaa Xaa Xaa Xaa Gly Pro Gly Xaa Xaa Xaa Xaa
            995                 1000                1005

Xaa Gly Pro Gly Xaa Xaa Xaa Xaa Gly Pro Gly Xaa Xaa Xaa
            1010                1015                1020

Xaa Xaa Gly Pro Gly Xaa Xaa Xaa Xaa Xaa Gly Pro Gly Xaa
            1025                1030                1035

Xaa Xaa Xaa Gly Pro Gly Xaa Xaa Xaa Xaa Xaa Gly Pro Gly Xaa
            1040                1045                1050

Xaa Xaa Xaa Xaa Gly Pro Ser Ala Ala Ala Ala Ala Ala Ala Ala
            1055                1060                1065

Ala Ala Ala Ala Ala Ala Ala Ala Ala Ala Ala Gly Gly Tyr
            1070                1075                1080

Gly Pro Gly Xaa Xaa Xaa Xaa Xaa Gly Pro Gly Xaa Xaa Xaa Xaa
            1085                1090                1095

Xaa Gly Pro Gly Xaa Xaa Xaa Xaa Xaa Gly Pro Gly Xaa Xaa Xaa
            1100                1105                1110

Xaa Xaa Gly Pro Gly Xaa Xaa Xaa Xaa Xaa Gly Pro Gly Xaa Xaa
            1115                1120                1125

Xaa Xaa Xaa Gly Pro Gly Xaa Xaa Xaa Xaa Xaa Gly Pro Gly Xaa
```

```
                  1130              1135              1140

Xaa Xaa  Xaa Xaa Gly Pro Ser  Ala Ala Ala Ala  Ala Ala Ala
    1145              1150              1155

Ala Ala  Ala Ala Ala Ala Ala  Ala Ala Ala Ala  Gly Gly Tyr
    1160              1165              1170

Gly Pro  Gly Xaa Xaa Xaa Xaa  Xaa Gly Pro Gly  Xaa Xaa Xaa
    1175              1180              1185

Xaa Gly  Pro Gly Xaa Xaa Xaa  Xaa Xaa Gly Pro  Gly Xaa Xaa
    1190              1195              1200

Xaa Xaa  Gly Pro Gly Xaa Xaa  Xaa Xaa Xaa Gly  Pro Gly Xaa
    1205              1210              1215

Xaa Xaa  Xaa Gly Pro Gly Xaa  Xaa Xaa Xaa Gly  Pro Gly Xaa
    1220              1225              1230

Xaa Xaa  Xaa Xaa Gly Pro Ser  Ala Ala Ala Ala  Ala Ala Ala
    1235              1240              1245

Ala Ala  Ala Ala Ala Ala Ala  Ala Ala Ala Ala  Gly Gly Tyr
    1250              1255              1260

Gly Pro  Gly Xaa Xaa Xaa Xaa  Xaa Gly Pro Gly  Xaa Xaa Xaa
    1265              1270              1275

Xaa Gly  Pro Gly Xaa Xaa Xaa  Xaa Xaa Gly Pro  Gly Xaa Xaa
    1280              1285              1290

Xaa Xaa  Gly Pro Gly Xaa Xaa  Xaa Xaa Xaa Gly  Pro Gly Xaa
    1295              1300              1305

Xaa Xaa  Xaa Gly Pro Gly Xaa  Xaa Xaa Xaa Gly  Pro Gly Xaa
    1310              1315              1320

Xaa Xaa  Xaa Xaa Gly Pro Ser  Ala Ala Ala Ala  Ala Ala Ala
    1325              1330              1335

Ala Ala  Ala Ala Ala Ala Ala  Ala Ala Ala Ala  Gly Gly Tyr
    1340              1345              1350

Gly Pro  Gly Xaa Xaa Xaa Xaa  Xaa Gly Pro Gly  Xaa Xaa Xaa
    1355              1360              1365

Xaa Gly  Pro Gly Xaa Xaa Xaa  Xaa Xaa Gly Pro  Gly Xaa Xaa
    1370              1375              1380

Xaa Xaa  Gly Pro Gly Xaa Xaa  Xaa Xaa Xaa Gly  Pro Gly Xaa
    1385              1390              1395

Xaa Xaa  Xaa Gly Pro Gly Xaa  Xaa Xaa Xaa Gly  Pro Gly Xaa
    1400              1405              1410

Xaa Xaa  Xaa Xaa Gly Pro Ser  Ala Ala Ala Ala  Ala Ala Ala
    1415              1420              1425

Ala Ala  Ala Ala Ala Ala Ala  Ala Ala Ala Ala  Gly Gly Tyr
    1430              1435              1440

Gly Pro  Gly Xaa Xaa Xaa Xaa  Xaa Gly Pro Gly  Xaa Xaa Xaa
    1445              1450              1455

Xaa Gly  Pro Gly Xaa Xaa Xaa  Xaa Xaa Gly Pro  Gly Xaa Xaa
    1460              1465              1470

Xaa Xaa  Gly Pro Gly Xaa Xaa  Xaa Xaa Xaa Gly  Pro Gly Xaa
    1475              1480              1485

Xaa Xaa  Xaa Gly Pro Gly Xaa  Xaa Xaa Xaa Gly  Pro Gly Xaa
    1490              1495              1500

Xaa Xaa  Xaa Xaa Gly Pro Ser  Ala Ala Ala Ala  Ala Ala Ala
    1505              1510              1515

Ala Ala  Ala Ala Ala Ala Ala  Ala Ala Ala Ala  Gly Gly Tyr
    1520              1525              1530
```

```
Gly Pro Gly Xaa Xaa Xaa Xaa Gly Pro Gly Xaa Xaa Xaa Xaa
    1535                1540                1545

Xaa Gly Pro Gly Xaa Xaa Xaa Xaa Gly Pro Gly Xaa Xaa Xaa
    1550                1555                1560

Xaa Xaa Gly Pro Gly Xaa Xaa Xaa Xaa Gly Pro Gly Xaa Xaa
    1565                1570                1575

Xaa Xaa Xaa Gly Pro Gly Xaa Xaa Xaa Xaa Gly Pro Gly Xaa
    1580                1585                1590

Xaa Xaa Xaa Xaa Gly Pro Ser Ala Ala Ala Ala Ala Ala Ala
    1595                1600                1605

Ala Ala Ala Ala Ala Ala Ala Ala Ala Ala Ala Gly Gly Tyr
    1610                1615                1620

Gly Pro Gly Xaa Xaa Xaa Xaa Gly Pro Gly Xaa Xaa Xaa Xaa
    1625                1630                1635

Xaa Gly Pro Gly Xaa Xaa Xaa Xaa Gly Pro Gly Xaa Xaa Xaa
    1640                1645                1650

Xaa Xaa Gly Pro Gly Xaa Xaa Xaa Xaa Gly Pro Gly Xaa Xaa
    1655                1660                1665

Xaa Xaa Xaa Gly Pro Gly Xaa Xaa Xaa Xaa Gly Pro Gly Xaa
    1670                1675                1680

Xaa Xaa Xaa Xaa Gly Pro Ser Ala Ala Ala Ala Ala Ala Ala
    1685                1690                1695

Ala Ala Ala Ala Ala Ala Ala Ala Ala Ala Ala Gly Gly Tyr
    1700                1705                1710

Gly Pro Gly Xaa Xaa Xaa Xaa Gly Pro Gly Xaa Xaa Xaa Xaa
    1715                1720                1725

Xaa Gly Pro Gly Xaa Xaa Xaa Xaa Gly Pro Gly Xaa Xaa Xaa
    1730                1735                1740

Xaa Xaa Gly Pro Gly Xaa Xaa Xaa Xaa Gly Pro Gly Xaa Xaa
    1745                1750                1755

Xaa Xaa Xaa Gly Pro Gly Xaa Xaa Xaa Xaa Gly Pro Gly Xaa
    1760                1765                1770

Xaa Xaa Xaa Xaa Gly Pro Ser Ala Ala Ala Ala Ala Ala Ala
    1775                1780                1785

Ala Ala Ala Ala Ala Ala Ala Ala Ala Ala Ala Ala
    1790                1795                1800

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Gly Gly Gln Gln
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117
```

```
Gly Ala Gly Gln Gln
1               5

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gln Gly Pro Tyr
1               5

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Gly Gln Gln
1

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: This sequence may encompass 6-8 residues

<400> SEQUENCE: 120

His His His His His His His His
1               5
```

COMPOSITIONS AND METHODS FOR PRODUCING HIGH SECRETED YIELDS OF RECOMBINANT PROTEINS

CROSS REFERENCE TO RELATED APPLICATIONS

This application is a continuation of U.S. application Ser. No. 17/138,350. filed Dec. 30, 2020, which is a continuation of U.S. application Ser. No. 15/920,331, filed Mar. 13, 2018, which is a bypass continuation of and claims priority to International Application No. PCT/US2018/021817, filed Mar. 9, 2018, which claims the benefit of U.S. Provisional Patent Application No. 62/470,153, filed Mar. 10, 2017, the disclosure of each of which is incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "50009B_Seqlisting.txt." The Sequence Listing was created on May 23, 2022, and is 261,531 bytes in size. The subject matter of the Sequence Listing is incorporated by reference herein in its entirety.

FIELD OF THE INVENTION

The present disclosure relates to methods for producing recombinant proteins, as well as compositions used in and produced by such methods. Specifically, the present disclosure relates to methods for producing high secreted yields of recombinant proteins, as well as recombinant vectors, recombinant host cells, and fermentations used in such methods.

BACKGROUND OF THE INVENTION

Many proteins needed for research, industrial, or therapeutic purposes (e.g., enzymes, vaccines, hormones, and biopharmaceutical proteins) are produced industrially in recombinant host cells. Yeasts, in particular budding yeasts, are favored eukaryotic host organisms for such application. Yeast cells grow rapidly to high cell density in inexpensive media, and comprise cellular machinery for protein folding and post-translational modification (e.g., proteolytic maturation, disulfide bond formation, phosphorylation, O- and N-linked glycosylation). The most commonly used yeast species for production of recombinant proteins include *Saccharomyces cerevisiae, Pichia pastoris, Hansenula polymorpha*, and *Kluyveromyces lactis*. Of these, *Pichia pastoris* is particularly suitable for applications in which recombinant proteins are to be produced at larger (e.g., industrial) scale because it can achieve high density cell growth.

Industrial scale production of recombinant proteins in recombinant host cells is facilitated when the recombinant proteins are secreted from the cells because secreted proteins are readily separated from intact cells, obviating the need for cellular lysis and subsequent separation of the proteins from cellular debris. *Pichia pastoris* is particularly suitable for production of secreted recombinant proteins because it can grow in minimal salt media, which permits isolation of secreted proteins via filtration and chromatography at low conductivity, and because *Pichia pastoris* natively secretes relatively few fermentative products (i.e., small proteins), which further facilitates isolation and purification of secreted recombinant proteins.

Recombinant host cells used for production of secreted recombinant proteins ideally produce large quantities of the recombinant protein, and secrete large fractions of the recombinant protein produced. The former is typically achieved by employing strategies well known in the art, such as, for example, codon optimizing the polynucleotide sequences that are engineered into the recombinant host cells and that encode the recombinant proteins, placing the transcription of such polynucleotide sequences under the control of strong promoters and effective terminators, optimizing translation by introducing suitable ribose binding sites, and increasing the copy number of the polynucleotide sequences in the recombinant host cells (e.g., by engineering host cells that comprise 2 or more copies of a particular polynucleotide sequence). These strategies, however, tend to reach a natural limit in their effectiveness as high copy numbers genetically destabilize the recombinant host cells, and strong promoters yield higher levels of the recombinant proteins than the recombinant host cells can properly fold and/or secrete (Damasceno et al. [2012] Appl Microbiol Biotechnol 93:31-39; Parekh et al. [1995] Protein Expr Purif. 6(4):537-45; Zhu et al. [2009] J Appl Microbiol 107:954-963; Liu et al. [2003] Protein Expr. Purif. 30:262-274). As a result, yields of the recombinant proteins tend to plateau or even decline as unfolded or mis-folded recombinant proteins accumulate inside the recombinant host cells and the recombinant host cells activate molecular stress responses (e.g., the unfolded protein response [UPR] or the ER-associated protein degradation pathway [ERAD](Hohenblum et al. [2004] Biotechnol Bioeng. 12:367-375; Vassileva et al. [2001] J Biotechnol. 12:21-35; Inan et al. [2006] Biotechnol Bioeng. 12:771-778; Zhu et al. [2009] J Appl Microbiol. 12(3):954-963). Indeed, up-regulation of chaperone proteins or of the main UPR transcriptional regulator (Hac1p) have been shown to reduce the effects of the UPR and to boost recombinant protein yields (Zhang et al. [2006] Biotechnol Prog. 12:1090-1095; Lee et al. [2012] Process Biochem. 12:2300-2305; Valkonen et al. [2003] Appl Environ Microbiol. 12:6979-6986). However, such measures have produced mixed results (Guerfal et al. [2010] Microb Cell Fact. 12:49) and still do not completely eliminate the saturation of the secretory pathways of recombinant host cells (Inan et al. [2006] Biotechnol Bioeng. 12:771-778). The capacity of the secretion machinery of recombinant host cells thus remains a major bottleneck for production of recombinant proteins.

What is needed therefore, are methods and compositions that allow increased expression of desirable recombinant proteins while alleviating the negative impact of overexpression on the recombinant host cells.

BRIEF DESCRIPTION OF THE DRAWINGS

(FIG. 2A) Illustrative map of recombinant vector used for introduction of a single copy of the polynucleotide sequences. (FIG. 2B) Illustrative map of recombinant vector used for introduction of triple copies of the polynucleotide sequences.

Figure 1:
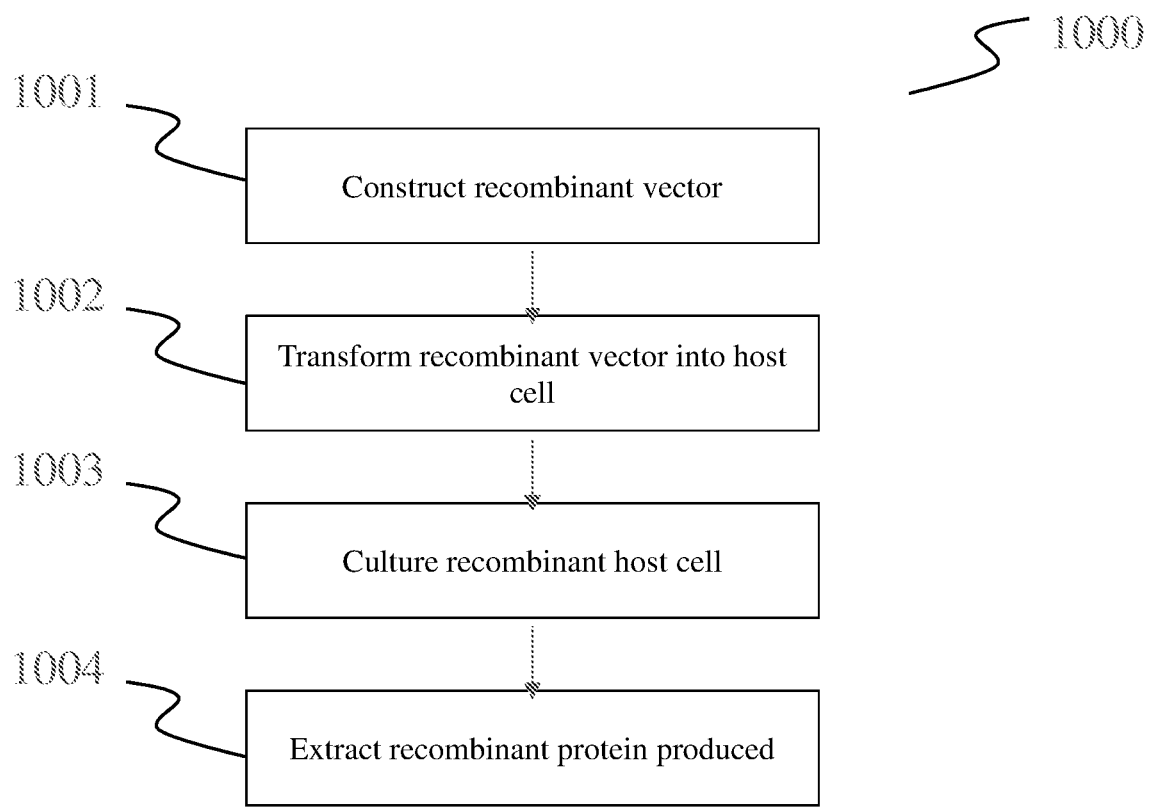
FIG. 1 is a flow diagram of methods for producing high secreted yields of recombinant proteins.

The figures depict various embodiments of the present disclosure for purposes of illustration only. One skilled in the art will readily recognize from the following discussion that alternative embodiments of the structures and methods illustrated herein may be employed without departing from the principles described herein.

DETAILED DESCRIPTION OF THE INVENTION

Definitions

Unless defined otherwise, all technical and scientific terms used herein have the same meaning as is commonly understood by one of ordinary skill in the art to which this disclosure pertains.

The terms "a" and "an" and "the" and similar referents as used herein refer to both the singular and the plural, unless otherwise indicated herein or clearly contradicted by context.

Amino acids can be referred to by their single-letter codes or by their three-letter codes. The single-letter codes, amino acid names, and three-letter codes are as follows: G—Glycine (Gly), P—Proline (Pro), A—Alanine (Ala), V—Valine (Val), L—Leucine (Leu), I—Isoleucine (Ile), M—Methionine (Met), C—Cysteine (Cys), F—Phenylalanine (Phe), Y—Tyrosine (Tyr), W—Tryptophan (Trp), H—Histidine (His), K—Lysine (Lys), R—Arginine (Arg), Q—Glutamine (Gln), N—Asparagine (Asn), E—Glutamic Acid (Glu), D—Aspartic Acid (Asp), S—Serine (Ser), T—Threonine (Thr).

The term "functional variant" as used herein refers to a protein that differs in composition from a native protein, where the functional properties are preserved to within 10% of the native protein properties. In some embodiments, the difference between the functional variant and the native protein can be in primary amino acid sequence (e.g., one or more amino acids are removed, inserted, or substituted) or post-translation modifications (e.g., glycosylation, phosphorylation). Amino acid insertions may comprise N-terminal and/or C-terminal fusions as well as intra-sequence insertions of single or multiple amino acids. Amino acid substitution includes non-conservative and conservative substitutions, where conservative amino acid substitution tables are well known in the art (see, for example, Creighton (1984) Proteins. W. H. Freeman and Company (Eds)). In some embodiments, the functional variant and the native protein have an at least 80%, at least 85%, at least 90%, at least 95%, or at least 99% amino acid or nucleotide sequence identity.

The terms "identity" or "identical" in the context of nucleic acid or amino acid sequences as used herein refer to the nucleotide or amino acid residues in the two sequences that are the same when the sequences are aligned for maximum correspondence. Depending on the application, the percent "identity" can exist over a region of the sequences being compared (i.e., subsequence [e.g., over a functional domain]) or, alternatively, exist over the full length of the sequences. A "region" is considered to be a continuous stretch of at least 9, 20, 24, 28, 32, or 36 nucleotides, or at least 6 amino acids. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). One example of an algorithm that is suitable for determining percent sequence identity and sequence similarity is the BLAST algorithm (see, for example, Altschul et al. [1990] J. Mol. Biol. 215:403-410; Gish & States. [1993] Nature Genet. 3:266-272; Madden et al. [1996] Meth. Enzymol. 266:131-141; Altschul et al. [1997] Nucleic Acids Res. 25:3389-3402; Zhang 7 Madden. [1997] Genome Res. 7:649-656). Software for performing BLAST analyses is publicly available through the National Center for Biotechnology Information. Such software also can be used to determine the mole percentage of any specified amino acid found within a polypeptide sequence or within a domain of such a sequence. As the person of ordinary skill will recognize such percentages also can be determined through inspection and manual calculation.

The terms "including," "includes," "having," "has," "with," or variants thereof are intended to be inclusive in a manner similar to the term "comprising".

The term "microbe" as used herein refers to a microorganism, and refers to a unicellular organism. As used herein, the term includes all bacteria, all archaea, unicellular protista, unicellular animals, unicellular plants, unicellular fungi, unicellular algae, all protozoa, and all chromista.

The term "native" as used herein refers to what is found in nature in its natural, unmodified state.

The term "operably linked" as used herein refers to polynucleotide or amino acid sequences that are in contiguous linkage with a polynucleotide sequence encoding a protein or a protein, as well as to polynucleotide or amino acid sequences that act in trans or at a distance to a polynucleotide sequence encoding a protein, and that control the transcription, translation, folding, secretion, or other functional aspect of the polynucleotide encoding the protein or the protein.

The terms "optional" or "optionally" mean that the feature or structure may or may not be present, or that an event or circumstance may or may not occur, and that the description includes instances where a particular feature or structure is present and instances where the feature or structure is absent, or instances where the event or circumstance occurs and instances where the event or circumstance does not occur.

The term "protein" as used herein refers to both a polypeptide without functional structure and a polypeptide that folds into an active structure.

The term "recombinant protein" as used herein refers to a protein that is produced in a recombinant host cell, or to a protein that is synthesized from a recombinant nucleic acid.

The term "recombinant host cell" as used herein refers to a host cell that comprises a recombinant nucleic acid.

The term "recombinant nucleic acid" as used herein refers to a nucleic acid that is removed from its naturally occurring environment, or a nucleic acid that is not associated with all or a portion of a nucleic acid abutting or proximal to the nucleic acid when it is found in nature, or a nucleic acid that is operatively linked to a nucleic acid that it is not linked to in nature, or a nucleic acid that does not occur in nature, or a nucleic acid that contains a modification that is not found in that nucleic acid in nature (e.g., insertion, deletion, or point mutation introduced artificially, e.g., by human intervention), or a nucleic acid that is integrated into a chromosome at a heterologous site. The term includes cloned DNA isolates and nucleic acids that comprise chemically-synthesized nucleotide analog.

The term "recombinant secretion signal" as used herein refers to a secretion signal that comprises a non-native combination of a signal peptide and a leader peptide.

The term "recombinant vector" as used herein refers to a nucleic acid molecule capable of transporting another nucleic acid molecule to which it has been linked. The term includes "plasmids", which generally refers to a circular double stranded DNA loop into which additional DNA segments can be ligated, and linear double-stranded molecules, such as those resulting from amplification by the polymerase chain reaction (PCR) or from treatment of a plasmid with a restriction enzyme. Other non-limiting examples of vectors include bacteriophages, cosmids, bacterial artificial chromosomes (BAC), yeast artificial chromosomes (YAC), and viral vectors (i.e., complete or partial viral genomes into which additional DNA segments are ligated). Certain vectors are capable of autonomous replication in a recombinant host cell into which they are introduced (e.g., vectors having an origin of replication that functions in the cell). Other vectors upon introduction can be integrated into the genome of a recombinant host cell, and are thereby replicated along with the cell genome.

The term "secreted recombinant protein" as used herein refers to a recombinant protein that is exported across the cellular membrane and/or cell wall of a recombinant host cell that produces the recombinant protein.

The term "secreted yield" as used herein refers to the amount of secreted protein produced by a host cell based on a fixed amount of carbon supplied to a fermentation comprising the host cell.

The term "total yield" as used herein refers to the amount of total protein produced by a host cell based on a fixed amount of carbon supplied to a fermentation comprising the host cell.

The term "truncated" as used herein refers to a protein sequence that is shorter in length than a native protein. In some embodiments, the truncated protein can be greater than 10%, or greater than 20%, or greater than 30%, or greater than 40%, or greater than 50%, or greater than 60%, or greater than 70%, or greater than 80%, or greater than 90% of the length of the native protein.

Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Wherever a range of values is recited, that range includes every value falling within the range, as if written out explicitly, and further includes the values bounding the range. Thus, a range of "from X to Y" includes every value falling between X and Y, and includes X and Y.

Compositions and Methods for Producing High Secreted Yields of Recombinant Proteins Provided herein are recombinant host cells and fermentations, and methods that use such recombinant host cells and fermentations for producing high secreted yields of recombinant proteins.

Advantages of the compositions and methods provided herein include that they provide cost-effective means for producing large quantities of recombinant proteins. The large quantities are obtained using recombinant host cells that secrete recombinant proteins via their secretory pathways. Such secretion of recombinant proteins a) avoids toxicity from intracellular accumulation of recombinant proteins; b) simplifies purification by eliminating cell disruption, separation from cellular components, and protein refolding processes; and c) provides properly folded recombinant proteins with post-translational modifications that may be critical to the activity/function of the recombinant proteins.

Recombinant Host Cells

The recombinant host cells provided herein are host cells that employ multiple distinct secretion signals for effecting secretion of a recombinant protein.

Secretion Signals

To be secreted, a protein has to travel through the intracellular secretory pathway of a cell that produces it. The protein is directed to this pathway, rather than to alternative cellular destinations, via an N-terminal secretion signal. At a minimum, a secretion signal comprises a signal peptide. Signal peptides typically consist of 13 to 36 mostly hydrophobic amino acids flanked by N-terminal basic amino acids and C-terminal polar amino acids. The signal peptide interacts with the signal recognition particle (SRP) or other transport proteins (e.g., SND, GET) that mediates the co- or post-translational translocation of the nascent protein from the cytosol into the lumen of the ER. In the ER, the signal peptide is typically cleaved off and the protein folds and undergoes post-translational modifications. The protein is then delivered from the ER to the Golgi apparatus and then on to secretory vesicles and the cell exterior. In addition to a signal peptide, a subset of nascent proteins natively destined for secretion carry a secretion signal that also comprises a leader peptide. Leader peptides typically consist of hydrophobic amino acids interrupted by charged or polar amino acids. Without wishing to be bound by theory, it is believed that the leader peptide slows down transport and ensures proper folding of the protein, and/or facilitates transport of the protein from the ER to the Golgi apparatus, where the leader peptide is typically cleaved off.

The amount of protein that is secreted from a cell varies significantly between proteins, and is dependent in part on the secretion signal that is operably linked to the protein in its nascent state. A number of secretion signals are known in the art, and some are commonly used for production of secreted recombinant proteins. Prominent among these is the secretion signal of the α-mating factor (αMF) of *Saccharomyces cerevisiae*, which consists of a N-terminal 19-amino-acid signal peptide (also referred to herein as pre-αMF(sc)) followed by a 70-amino-acid leader peptide (also referred to herein as pro-αMF(sc); SEQ ID NO: 1). Inclusion of pro-αMF(sc) in the secretion signal of the αMF of *Saccharomyces cerevisiae* (also referred to herein as pre-αMF(sc)/pro-αMF(sc) (SEQ ID NO: 7) has proven critical for achieving high secreted yields of proteins (see, for example, Fitzgerald & Glick [2014] Microb Cell Fact 28; 13(1):125; Fahnestock et al. [2000] J Biotechnol 74(2):105). Addition of pro-αMF(sc) or functional variants thereof to signal peptides other than pre-αMF(sc) has also been explored as a means of achieving secretion of recombinant proteins, but has shown variable degrees of effectiveness, increasing secretion for certain recombinant proteins in certain recombinant host cells but having no effect or decreasing secretion for other recombinant proteins (Fitzgerald & Glick. [2014] Microb Cell Fact 28; 13(1):125; Liu et al. [2005] Biochem Biophys Res Commun. 326(4):817-24; Obst et al. [2017] ACS Synth Biol. 2017 Mar. 2).

The invention provided herein is based on the surprising discovery made by the inventors that the use of multiple distinct secretion signals can improve the secreted yields of recombinant proteins. Specifically, the inventors found that compared to recombinant host cells that comprise multiple polynucleotide sequences encoding a recombinant protein operably linked to just one secretion signal (e.g., pre-αMF (sc)/pro-αMF(sc)), recombinant host cells that comprise the same number of polynucleotide sequences encoding the recombinant protein operably linked to at least 2 distinct secretion signals produce higher secreted yields of the recombinant protein. Without wishing to be bound by theory, the use of at least 2 distinct secretion signals may permit the recombinant host cell to engage distinct cellular secretory pathways to effect efficient secretion of the recombinant protein and thus prevent over-saturation of any one secretion pathway.

Accordingly, the recombinant host cells provided herein are host cells that comprise at least 2 polynucleotide sequences that encode a recombinant protein operably linked to at least 2 distinct secretion signals. The secretion signals are typically linked to the N-terminus of the protein.

In some embodiments, at least one of the distinct secretion signals comprises a signal peptide but no leader peptide. In some embodiments, at least one of the distinct secretion signals comprises a signal peptide and a leader peptide. In some embodiments, at least one of the distinct secretion signals is a native secretion signal or a functional variant that has an at least 80% amino acid sequence identity to the native secretion signal. In some embodiments, at least one of the distinct secretion signals is a recombinant secretion signal.

In some embodiments, at least one of the distinct secretion signals comprises a signal peptide selected from Table 1 or is a functional variant that has an at least 80% amino acid sequence identity to a signal peptide selected from Table 1. In some embodiments, the functional variant is a signal peptide selected from Table 1 that comprises one or two substituted amino acids. In some such embodiments, the functional variant has an at least 85%, at least 90%, at least 95%, or at least 99% amino acid sequence identity to a signal peptide selected from Table 1. In some embodiments, the signal peptide mediates translocation of the nascent recombinant protein into the ER post-translationally (i.e., protein synthesis precedes translocation such that the nascent recombinant protein is present in the cell cytosol prior to translocating into the ER). In other embodiments, the signal peptide mediates translocation of the nascent recombinant protein into the ER co-translationally (i.e., protein synthesis and translocation into the ER occur simultaneously). An advantage of using a signal peptide that mediates co-translational translocation into the ER is that recombinant proteins prone to rapid folding are prevented from assuming conformations that hinder translocation into the ER and thus secretion.

TABLE 1

Signal Peptides

| Source Gene ID | Species | Name | SEQ ID NO | Sequence |
| --- | --- | --- | --- | --- |
| PEP4 | *Saccharomyces cerevisiae* | pre-PEP4(sc) | 3 | MFSLKALLPLALLLVSANQVAA |
| PAS_chr1-1_0130 | *Pichia pastoris* | pre-DSE4(pp) | 4 | MSFSSNVPQLFLLLVLLTNIVSG |
| PAS_chr3_0076 | *Pichia pastoris* | pre-EPX1(pp) | 5 | MKLSTNLILAIAAASAVVSA |

TABLE 1-continued

Signal Peptides

| Source Gene ID | Species | Name | SEQ ID NO | Sequence |
|---|---|---|---|---|
| P00698 | Gallus gallus | pre-CLSP(gg) | 6 | MRSLLILVLCFLPLAALG |

In some embodiments, at least one of the distinct secretions signals comprises a leader peptide that is native pro-αMF(sc) (SEQ ID NO: 1) or a functional variant that has an at least 80% amino acid sequence identity to SEQ ID NO: 1. In some embodiments, the functional variant is native pro-αMF(sc) comprising one or two substituted amino acids. In some embodiments, the functional variant is *pro-αMF (SEQ ID NO: 2). In some embodiments, the functional variant has an at least 85%, at least 90%, at least 95%, or at least 99% amino acid identity to SEQ ID NO: 1. In some embodiments, the functional variant is αMF_no_EAEA or αMFΔ or αMFΔ_no_Kex (Obst et al. [2017] ACS Synth Biol. 2017 Mar. 2).

In some embodiments, at least one of the distinct secretion signals comprises a leader peptide is native pro-αMF(sc) (SEQ ID NO: 1) or a functional variant that has an at least 80% amino acid sequence identity to SEQ ID NO: 1, and a signal peptide that does not comprise pre-αMF(sc). In some embodiments, the functional variant has an at least 85%, at least 90%, at least 95%, or at least 99% amino acid identity to SEQ ID NO: 1; is native pro-αMF(sc) comprising one or two substituted amino acids; is *pro-αMF (SEQ ID NO: 2); or is αMF_no_EAEA or αMFΔ or αMFΔ_no_Kex (Obst et al. [2017] ACS Synth Biol. 2017 Mar. 2). In some embodiments, the signal peptide is selected from Table 1; is a signal peptide selected from Table 1 that comprises one or two substituted amino acids; or has an at least 85%, at least 90%, at least 95%, or at least 99% amino acid sequence identity to a signal peptide selected from Table 1. In some embodiments, at least one of the distinct secretion signals is native pre-αMF(sc)/pro-αMF(sc) (SEQ ID NO: 7) or a functional variant that has an at least 80% amino acid sequence identity to SEQ ID NO: 7, and at least one other of the distinct secretion signals is a recombinant secretion signal that comprises native pro-αMF(sc) (SEQ ID NO: 1) or a functional variant that has an at least 80% amino acid sequence identity to SEQ ID NO: 1 and a signal peptide that is not pre-αMF(sc). In some embodiments, the functional variant of native pre-αMF(sc)/pro-αMF(sc); is native pre-αMF(sc)/pro-αMF(sc) comprising two to four substituted amino acid changes; is pre-αMF(sc)/*pro-αMF(sc) (SEQ ID NO: 8); or has an at least 85%, at least 90%, at least 95%, or at least 99% amino acid sequence identity to SEQ ID NO: 7. In some such embodiments, and functional variant of native pro-αMF(sc) is native pro-αMF(sc) comprising one or two substituted amino acid changes; is *pro-αMF (SEQ ID NO: 2); has an at least 85%, at least 90%, at least 95%, or at least 99% amino acid sequence identity to SEQ ID NO: 1; or is αMF_no_EAEA or αMFΔ or αMFΔ_no_Kex (Obst et al. [2017] ACS Synth Biol. 2017 Mar. 2). In some embodiments, the signal peptide that is not pre-αMF(sc) is selected from Table 1 or is a functional variant that has an at least 80% amino acid sequence identity to a signal peptide selected from Table 1. In some such embodiments, the signal peptide is a signal peptide selected from Table 1 that comprises one or two substituted amino acids; or has an at least 85%, at least 90%, at least 95%, or at least 99% amino acid sequence identity to a signal peptide selected from Table 1. In some embodiments, the recombinant secretion signal is selected from SEQ ID NOs: 9 through 12 in Table 2 or is a functional variant that has an at least 85%, at least 90%, at least 95%, or are at least 99% amino acid sequence identity to a recombinant secretion signal selected from SEQ ID NOs: 9 through 12.

TABLE 2

Recombinant Secretion Signals

| Name | SEQ ID NO | Sequence |
|---|---|---|
| pre-αMF(sc)/ pro-αMF(sc) | 7 | MRFPSIFTAVLFAASSALAAPVNTTTEDETAQIPAEAVIGY LDLEGDFDVAVLPFSNSTNNGLLFINTTIASIAAKEEGVSLD KREAEA |
| pre-αMF(sc)/ *pro-αMF(sc) | 8 | MRFPSIFTAVLFAASSALAAPVNTTTEDETAQIPAEAVIGYS DLEGDFDVAVLPFSNSTNNGLLFINTTIASIAAKEEGVSLEK REAEA |
| pre-PEP4(sc)/ *pro-αMF(sc) | 9 | MFSLKALLPLALLLVSANQVAAAPVNTTTEDETAQIPAEA VIGYSDLEGDFDVAVLPFSNSTNNGLLFINTTIASIAAKEEG VSLEKREAEA |
| pre-DSE4(pp)/ *pro-αMF(sc) | 10 | MSFSSNVPQLFLLLVLLTNIVSGAPVNTTTEDETAQIPAEA VIGYSDLEGDFDVAVLPFSNSTNNGLLFINTTIASIAAKEEG VSLEKREAEA |
| pre-EPX1(pp)/ *pro-αMF(sc) | 11 | MKLSTNLILAIAAASAVVSAAPVNTTTEDETAQIPAEAVIG YSDLEGDFDVAVLPFSNSTNNGLLFINTTIASIAAKEEGVSL EKREAEA |

TABLE 2-continued

Recombinant Secretion Signals

| Name | SEQ ID NO | Sequence |
|---|---|---|
| pre-CLSP(gg)/ *pro-αMF(sc) | 12 | MRSLLILVLCFLPLAALGAPVNTTTEDETAQIPAEAVIGYS DLEGDFDVAVLPFSNSTNNGLLFINTTIASIAAKEEGVSLEK REAEA |

Suitable distinct secretion signals and combinations of secretion signals can be identified by using methods disclosed herein. Such methods comprise the steps of:
a) measuring secreted yields of a recombinant protein produced by a recombinant host cell A that comprises z copies of a first polynucleotide sequence encoding a recombinant protein operably linked to a first secretion signal;
b) measuring secreted yields of the recombinant protein produced by a recombinant host cell B that comprises m copies of the first polynucleotide sequence and n copies of a second polynucleotide sequence encoding the recombinant protein operably linked to a second secretion signal, wherein recombinant host cell A and recombinant host cell B are identical except for the number of copies of the first and second polynucleotide sequences, wherein m+n=z, and wherein the first and second secretion signals are not identical; and
c) selecting a combination of a first and a second secretion signal that provides at least 2%, at least 5%, at least 10%, at least 15%, at least 20%, at least 30%, at least 40%, at least 50%, at least 60%, at least 70%, at least 80%, at least 90%, or at least 95% greater secreted yield of the recombinant protein in recombinant host cell B than is achieved with recombinant host cell A.

In some embodiments, recombinant host cell B comprises y copies of a third polynucleotide sequences encoding the recombinant protein operably linked to a third secretion signal, wherein recombinant host cell A and recombinant host cell B are identical except for the number of copies of the first, second, and third polynucleotide sequences, wherein m+n+y=z, and wherein the first, second, and third secretion signals are not identical. In further embodiments, recombinant host cell B comprises additional polynucleotide sequences encoding the recombinant protein operably linked to additional distinct secretion signals. In embodiments in which a recombinant host cell A that comprises the same number of polynucleotide sequences as a recombinant host cell B cannot be isolated, step c) can use a recombinant host cell A that comprises fewer copies polynucleotide sequences. Without wishing to be bound by theory, the inability to isolate a recombinant host cell A with a certain number of polynucleotide sequences may be due to a genetic instability or poor host cell health effected by an increased number of copies of identical polynucleotide sequences.

In some embodiments, the expression constructs are stably integrated within the genome (e.g., a chromosome) of the recombinant host cells, e.g., via homologous recombination or targeted integration. Non-limiting examples of suitable sites for genomic integration include the Ty1 loci in the *Saccharomyces cerevisiae* genome, the rDNA and HSP82 loci in the *Pichia pastoris* genome, and transposable elements that have copies scattered throughout the genome of the recombinant host cells. In other embodiments, the expression constructs are not stably integrated within the genome of the recombinant host cells but rather are maintained extrachromosomally (e.g., on a plasmid). The polynucleotide sequences may be positioned at a single location within the genome of the recombinant host cells, or be distributed across the genome of the recombinant host cells. In some embodiments, the polynucleotide sequences are arranged in the genomes of the recombinant host cells as head-to-tail expression cassette multimers.

The use of at least 2 distinct secretion signals as provided herein provides for high secreted yields of recombinant proteins. Accordingly, in various embodiments, the recombinant host cells produce secreted yields of the recombinant protein of at least 1%, at least 5%, at least 10%, at least 20%, or at least 30%; from 1% to 100%, to 90%, to 80%, to 70%, to 60%, to 50%, to 40%, to 30%, to 20%, or 10%; from 10% to 100%, to 90%, to 80%, to 70%, to 60%, to 50%, to 40%, to 30%, or to 20%; from 20% to 100%, to 90%, to 80%, to 70%, to 60%, to 50%, to 40%, or to 30%; from 30% to 100%, to 90%, to 80%, to 70%, to 60%, to 50%, or to 40%; from 40% to 100%, to 90%, to 80%, to 70%, to 60%, or to 50%; from 50% to 100%, to 90%, to 80%, to 70%, or to 60%; from 60% to 100%, to 90%, to 80%, or to 70%; from 70% to 100%, to 90%, or to 80%; from 80% to 100%, or to 90%; or from 90% to 100% by weight of total yields of the recombinant protein produced by the recombinant host cells. The identities of proteins produced can be confirmed by HPLC quantification, Western blot analysis, polyacrylamide gel electrophoresis, and 2-dimensional mass spectroscopy (2D-MS/MS) sequence identification.

Recombinant Proteins

The recombinant proteins encoded by the at least 2 polynucleotide sequences comprised in the recombinant host cells provided herein may be any protein.

In some embodiments, the recombinant proteins are silk or silk-like proteins. Such silk or silk-like proteins can be selected from a vast array of full-length or truncated native silk proteins or of functional variants of full-length or truncated native silk proteins, or comprise domains of native silk proteins or of functional variants of silk proteins. Putative native silk proteins can be identified by searching sequence databases (e.g., GenBank) for relevant terms (e.g., silkworm silk, spider silk, spidroin, fibroin, MaSp), and translating any nucleotide sequences into amino acid sequences.

In some embodiments, the silk or silk or silk-like proteins are full-length or truncated native silk proteins of a silkworm, or functional variants of full-length or truncated native silk proteins of a silkworm, or comprise domains of native or functional variants of native silk proteins of a silkworm. In some such embodiments, the silkworm is *Bombyx mori*.

In some embodiments, the silk or silk or silk-like proteins are full-length or truncated native silk proteins of a spider, or functional variants of full-length or truncated native silk proteins of a spider, or comprise domains of native or functional variants of native silk proteins of a spider. In some embodiments, the native silk proteins are selected from the group consisting of Major Ampullate spider fibroin (MaSp, also called dragline; e.g., MaSp1, MaSp2) silk proteins, Minor Ampullate spider fibroin (MiSp) silk proteins, Flagelliform spider fibroin (Flag) silk proteins, Aciniform spider fibroin (AcSp) silk proteins, Tubuliform spider fibroin (TuSp) silk proteins, and Pyriform spider fibroin (PySp) silk proteins of orb weaving spiders. In some embodiments, the spider is selected from the group consisting of *Agelenopsis aperta, Aliatypus gulosus, Aphonopelma seemanni, Aptostichus* sp. AS21 7, *Aptostichus* sp. AS220, *Araneus diadematus, Araneus gemmoides, Araneus ventricosus, Argiope amoena, Argiope argentata, Argiope bruennichi, Argiope trifasciata, Atypoides riversi, Avicularia juruensis, Bothriocyrtum californicum, Deinopis spinosa, Diguetia canities, Dolomedes tenebrosus, Euagrus chisoseus, Euprosthenops australis, Gasteracantha mammosa, Hypochilus thorelli, Kukulcania hibernalis, Latrodectus hesperus, Megahexura fulva, Metepeira grandiosa, Nephila antipodiana, Nephila clavata, Nephila clavipes, Nephila madagascariensis, Nephila pilipes, Nephilengys cruentata, Parawixia bistriata, Peucetia viridans, Plectreurys tristis, Poecilotheria regalis, Tetragnatha kauaiensis,* or *Uloborus diversus.*

Typically, silk proteins are large proteins (>150 kDa, >1000 amino acids) that can be broken down into 3 domains: an N-terminal non-repetitive domain (NTD), a repeat domain (REP), and a C-terminal non-repetitive domain (CTD). The REP comprises blocks of amino acid sequences ("repeat units") that are at least 12 amino acids long and that are repeated either perfectly ("exact-repeat units") or imperfectly ("quasi-repeat units"), and that can comprise 2 to 10 amino acid long sequence motifs (see FIG. 1). REPs typically make up about 90% of the native spider silk proteins, and assemble into the alanine-rich nanocrystalline (<10 nm) domains (likely made up of alternating beta sheets) and glycine-rich amorphous domains (possibly containing alpha-helices and/or beta-turns) that, without wanting to be bound by theory, are believed to confer strength and flexibility to spider silk fibers, respectively. The lengths and compositions of the REPs are known to vary among different spider silk proteins and across different spider species, giving rise to a broad range of silk fibers with specific properties.

In some embodiments, the silk or silk-like proteins comprise one or more native or functional variants of native REPs (e.g., 1, 2, 3, 4, 5, 6, 7, 8), zero or more native or functional variants of NTDs (e.g., 0, 1), and zero or more native or functional variants of native CTDs (e.g., 0, 1). In some embodiments, the silk or silk-like proteins comprise one or more NTDs that each comprise from 75 to 350 amino acids. In some embodiments, the silk or silk or silk-like proteins comprise one or more CTDs that each comprise from 75 to 350 amino acids. In some embodiments, the silk or silk or silk-like proteins comprise one or more REPs that comprise repeat units that each comprise more than 60, more than 100, more than 150, more than 200, more than 250, more than 300, more than 350, more than 400, more than 450, more than 500, more than 600, more than 700, more than 800, more than 900, more than 1000, more than 1250, more than 1500, more than 1750, or more than 2000; from 60 to 2000, to 1750, to 1500, to 1250, to 1000, to 900, to 800, to 700, to 600, to 500, to 450, to 400, to 350, to 300, to 250, to 200, to 150, or to 100; from 100 to 2000, to 1750, to 1500, to 1250, to 1000, to 900, to 800, to 700, to 600, to 500, to 450, to 400, to 350, to 300, to 250, to 200, or to 150; from 150 to 2000, to 1750, to 1500, to 1250, to 1000, to 900, to 800, to 700, to 600, to 500, to 450, to 400, to 350, to 300, to 250, or to 200; from 200 to 2000, to 1750, to 1500, to 1250, to 1000, to 900, to 800, to 700, to 600, to 500, to 450, to 400, to 350, to 300, or to 250; from 250 to 2000, to 1750, to 1500, to 1250, to 1000, to 900, to 800, to 700, to 600, to 500, to 450, to 400, to 350, or to 300; from 300 to 2000, to 1750, to 1500, to 1250, to 1000, to 900, to 800, to 700, to 600, to 500, to 450, to 400, or to 350; from 350 to 2000, to 1750, to 1500, to 1250, to 1000, to 900, to 800, to 700, to 600, to 500, to 450, or to 400; from 400 to 2000, to 1750, to 1500, to 1250, to 1000, to 900, to 800, to 700, to 600, to 500, or to 450; from 450 to 2000, to 1750, to 1500, to 1250, to 1000, to 900, to 800, to 700, to 600, or to 500; from 500 to 2000, to 1750, to 1500, to 1250, to 1000, to 900, to 800, to 700, or to 600; from 600 to 2000, to 1750, to 1500, to 1250, to 1000, to 900, to 800, or to 700; from 700 to 2000, to 1750, to 1500, to 1250, to 1000, to 900, or to 800; from 800 to 2000, to 1750, to 1500, to 1250, to 1000, or to 900; from 900 to 2000, to 1750, to 1500, to 1250, or to 1000; from 1000 to 2000, to 1750, to 1500, or to 1250; from 1250 to 2000, to 1750, or to 1500; from 1500 to 2000, or to 1750; or from 1750 to 2000 amino acid residues.

In some embodiments, the silk or silk or silk-like proteins comprise greater than 2, greater than 4, greater than 6, greater than 8, greater than 10, greater than 12, greater than 14, greater than 16, greater than 18, greater than 20, greater than 22, greater than 24, greater than 26, greater than 28, or greater than 30; from 2 to 30, to 28, to 26, to 24, to 22, to 20, to 18, to 16, to 14, to 12, to 10, to 8, to 6, or to 4; from 4 to 30, to 28, to 26, to 24, to 22, to 20, to 18, to 16, to 14, to 12, to 10, to 8, or to 6; from 6 to 30, to 28, to 26, to 24, to 22, to 20, to 18, to 16, to 14, to 12, to 10, or to 8; from 8 to 30, to 28, to 26, to 24, to 22, to 20, to 18, to 16, to 14, to 12, or to 10; from 10 to 30, to 28, to 26, to 24, to 22, to 20, to 18, to 16, to 14, or to 12; from 12 to 30, to 28, to 26, to 24, to 22, to 20, to 18, to 16, or to 14; from 14 to 30, to 28, to 26, to 24, to 22, to 20, to 18, or to 16; from 16 to 30, to 28, to 26, to 24, to 22, to 20, or to 18; from 18 to 30, to 28, to 26, to 24, to 22, or to 20; from 20 to 30, to 28, to 26, to 24, or to 22; from 22 to 30, to 28, to 26, or to 24; from 24 to 30, to 28, or to 26; from 26 to 30, or to 28; from 28 to 30 exact-repeat and/or quasi-repeat units that each have molecular weights of greater than 5 kDa, greater than 10 kDa, greater than 20 kDa, greater than 30 kDa, greater than 40 kDa, greater than 50 kDa, greater than 60 kDa, greater than 70 kDa, greater than 80 kDa, or greater than 90 kDa; from 5 kDa to 100 kDa, to 90 kDa, to 80 kDa, to 70 kDa, to 60 kDa, to 50 kDa, to 40 kDa, to 30 kDa, to 20 kDa, or to 10 kDa; from 10 kDa to 100 kDa, to 90 kDa, to 80 kDa, to 70 kDa, to 60 kDa, to 50 kDa, to 40 kDa, to 30 kDa, or to 20 kDa; from 20 kDa to 100 kDa, to 90 kDa, to 80 kDa, to 70 kDa, to 60 kDa, to 50 kDa, to 40 kDa, or to 30 kDa; from 30 kDa to 100 kDa, to 90 kDa, to 80 kDa, to 70 kDa, to 60 kDa, to 50 kDa, or to 40 kDa; from 40 kDa to 100 kDa, to 90 kDa, to 80 kDa, to 70 kDa, to 60 kDa, or to 50 kDa; from 50 kDa to 100 kDa, to 90 kDa, to 80 kDa, to 70 kDa, or to 60 kDa; from 60 kDa to 100 kDa, to 90 kDa, to 80 kDa, or to 70 kDa; from 70 kDa to 100 kDa, to 90 kDa, or to 80 kDa; from 80 kDa to 100 kDa, or to 90 kDa; or from 90 kDa to 100 kDa. In some such embodiments, the order of the 2 or more exact-repeat or quasi-repeat units within the silk or silk or silk-like proteins is not native.

In some embodiments, the silk or silk or silk-like proteins comprise more than 1, more than 2, more than 4, more than 6, more than 8, more than 10, more than 15, more than 20, or more than 25; from 1 to 30, to 25, to 20, to 15, to 10, to 8, to 6, to 4, or to 2; from 2 to 30, to 25, to 20, to 15, to 10, to 8, to 6, or to 4; from 4 to 30, to 25, to 20, to 15, to 10, to 8, or to 6; from 6 to 30, to 25, to 20, to 15, to 10, or to 8; from 8 to 30, to 25, to 20, to 15, or to 10; from 10 to 30, to 25, to 20, or to 15; from 15 to 30, to 25, or to 20; from 20 to 30, or to 25; or from 25 to 30 exact-repeat and/or quasi-repeat units that are glycine-rich. In some such embodiments, one or more of the glycine-rich exact-repeat and/or quasi-repeat units comprise more than 4, more than 6, more than 8, more than 10, more than 12, more than 15, more than 18, more than 20, more than 25, more than 30, more than 40, more than 50, more than 60, more than 70, more than 80, more than 90, more than 100, or more than 150; from 4 to 200, to 150, to 100, to 90, to 80, to 70, to 60, to 50, to 40, to 30, to 25, to 20, to 18, to 15, to 12, to 10, to 8, or to 6; from 6 to 200, to 150, to 100, to 90, to 80, to 70, to 60, to 50, to 40, to 30, to 25, to 20, to 18, to 15, to 12, to 10, or to 8; from 8 to 200, to 150, to 100, to 90, to 80, to 70, to 60, to 50, to 40, to 30, to 25, to 20, to 18, to 15, to 12, or to 10; from 10 to 200, to 150, to 100, to 90, to 80, to 70, to 60, to 50, to 40, to 30, to 25, to 20, to 18, to 15, or to 12; from 12 to 200, to 150, to 100, to 90, to 80, to 70, to 60, to 50, to 40, to 30, to 25, to 20, to 18, or to 15; from 15 to 200, to 150, to 100, to 90, to 80, to 70, to 60, to 50, to 40, to 30, to 25, to 20, or to 18; from 18 to 200, to 150, to 100, to 90, to 80, to 70, to 60, to 50, to 40, to 30, to 25, or to 20; from 20 to 200, to 150, to 100, to 90, to 80, to 70, to 60, to 50, to 40, to 30, or to 25; from 25 to 200, to 150, to 100, to 90, to 80, to 70, to 60, to 50, to 40, or to 30; from 30 to 200, to 150, to 100, to 90, to 80, to 70, to 60, to 50, or to 40; from 40 to 200, to 150, to 100, to 90, to 80, to 70, to 60, or to 50; from 50 to 200, to 150, to 100, to 90, to 80, to 70, or to 60; from 60 to 200, to 150, to 100, to 90, to 80, or to 70; from 70 to 200, to 150, to 100, to 90, or to 80; from 80 to 200, to 150, to 100, or to 90; from 90 to 200, to 150, or to 100; from 100 to 200, or to 150; or from 150 to 200 consecutive amino acids that are more than 30%, more than 40%, more than 45%, more than 50%, more than 55%, more than 60%, more than 70%, or more than 80%; from 30% to 100%, to 90%, to 80%, to 70%, to 60%, to 55%, to 50%, to 45%, or to 40%; from 40% to 100%, to 90%, to 80%, to 70%, to 60%, to 55%, to 50%, or to 45%; from 45% to 100%, to 90%, to 80%, to 70%, to 60%, to 55%, or to 50%; from 50% to 100%, to 90%, to 80%, to 70%, to 60%, or to 55%; from 55% to 100%, to 90%, to 80%, to 70%, or to 60%; from 60% to 100%, to 90%, to 80%, or to 70%; from 70% to 100%, to 90%, or to 80%; from 80% to 100%, or to 90%; or from 90% to 100% glycine.

In some embodiments, the silk or silk or silk-like proteins comprise more than 1, more than 2, more than 4, more than 6, more than 8, more than 10, more than 15, more than 20, or more than 25; from 1 to 30, to 25, to 20, to 15, to 10, to 8, to 6, to 4, or to 2; from 2 to 30, to 25, to 20, to 15, to 10, to 8, to 6, or to 4; from 4 to 30, to 25, to 20, to 15, to 10, to 8, or to 6; from 6 to 30, to 25, to 20, to 15, to 10, or to 8; from 8 to 30, to 25, to 20, to 15, or to 10; from 10 to 30, to 25, to 20, or to 15; from 15 to 30, to 25, or to 20; from 20 to 30, or to 25; or from 25 to 30 exact-repeat and/or quasi-repeat units that are alanine-rich. In some such embodiments, one or more of the alanine-rich exact-repeat and/or quasi-repeat units comprise more than 4, more than 6, more than 8, more than 10, more than 12, more than 15, or more than 18; from 4 to 20, to 18, to 15, to 12, to 10, to 8, or to 6; from 6 to 20, to 18, to 15, to 12, to 10, or to 8; from 8 to 20, to 18, to 15, to 12, or to 10; from 10 to 18, to 15, or to 12; from 12 to 20, to 18, or to 15; from 15 to 20, or to 18; or from 18 to 20; consecutive amino acids that are more than 70%, more than 75%, more than 80%, more than 85%, or more than 90%; from 70% to 100%, to 90%, to 85%, to 80%, or to 75%; from 75% to 100%, to 90%, to 85%, or to 80%; from 80% to 100%, to 90%, or to 85%; from 85% to 100%, or to 90%; or from 90% to 100% alanine.

In some embodiments, the silk or silk or silk-like proteins comprise one or more glycine-rich exact-repeat and/or quasi-repeat units that are from 20 to 100 amino acids long and that are concatenated with poly-alanine-rich regions that are from 4 to 20 amino acids long. In some embodiments, the silk or silk or silk-like proteins comprise 5-25% poly-alanine regions (from 4 to 20 poly-alanine residues). In some embodiments, the silk or silk or silk-like proteins comprise 25-50% glycine. In some embodiments, the silk or silk or silk-like proteins comprise 15-35% GGX, where X is any amino acid. In some embodiments, the silk or silk or silk-like proteins comprise 15-60% GPG. In some embodiments, the silk or silk or silk-like proteins comprise 10-40% alanine. In some embodiments, the silk or silk or silk-like proteins comprise 0-20% proline. In some embodiments, the silk or silk or silk-like proteins comprise 10-50% beta-turns. In some embodiments, the silk or silk or silk-like proteins comprise 10-50% alpha-helix composition. In some embodiments, all of these compositional ranges apply to the same silk or silk or silk-like protein. In some embodiments, 2 or more of these compositional ranges apply to the same silk or silk or silk-like protein.

In some embodiments, the structure of the silk or silk or silk-like proteins form beta-sheet structures, beta-turn structures, or alpha-helix structures. In some embodiments, the secondary, tertiary, and quaternary structures of the silk or silk or silk-like proteins have nanocrystalline beta-sheet regions, amorphous beta-turn regions, amorphous alpha helix regions, randomly spatially distributed nanocrystalline regions embedded in a non-crystalline matrix, or randomly oriented nanocrystalline regions embedded in a non-crystalline matrix. In some embodiments, the silk or silk or silk-like proteins are highly crystalline. In other embodiments, the silk or silk or silk-like proteins are highly amorphous. In some embodiments, the silk or silk or silk-like proteins comprise both crystalline and amorphous regions. In some embodiments, the silk or silk or silk-like proteins comprise from 10% to 40% crystalline material by volume.

In some embodiments, the silk or silk or silk-like proteins comprise one or more exact-repeat or quasi-repeat units that have at least 80%, at least 85%, at least 90%, at least 95%, or at least 99% amino acid sequence identity to a repeat unit of a native spider silk protein. In some embodiments, the silk or silk or silk-like proteins comprise one or more exact-repeat or quasi-repeat units that have an at least 80%, at least 85%, at least 90%, at least 95%, or at least 99% amino acid sequence identity to a repeat unit of a native spider dragline silk protein. In some embodiments, the silk or silk or silk-like proteins comprise one or more exact-repeat or quasi-repeat units that have at least 80%, at least 85%, at least 90%, at least 95%, or at least 99% amino acid sequence identity to a repeat unit of a native MA dragline silk protein. In some embodiments, the silk or silk or silk-like proteins comprise one or more exact-repeat or quasi-repeat units that have at least 80%, at least 85%, at least 90%, at least 95%, or at least 99% amino acid sequence identity to a repeat unit of a native MaSp2 dragline silk protein.

In some embodiments, the silk or silk or silk-like proteins comprise one or more quasi-repeat units, wherein the amino acid sequence of each quasi-repeat unit is described by Equation 1, wherein the amino acid sequence of X1 (termed a "motif") is described by Equation 2 and can vary randomly within each quasi-repeat unit. The sequence $[\text{GPG-X1}]_{n1}$ (SEQ ID NO: 113) is referred to as "first region", and is glycine-rich. The sequence $(A)_{n2}$ (SEQ ID NO: 114) is referred to as "second region", and is alanine-rich. In some embodiments, the value of n1 is any one of 4, 5, 6, 7, or 8. In some embodiments, the value of n2 is any one of 6, 7, 8, 9, 10, 11, 12, 13, 14, 15, 16, 17, 18, 19, or 20. In some embodiments, the value of n3 is any one from 2 to 20. In some embodiments, the silk or silk or silk-like proteins comprise one or more of quasi-repeat units that have at least 80%, at least 85%, at least 90%, at least 95%, or at least 99% amino acid sequence identity to a quasi-repeat unit described by Equations 1 and 2.

{GGY-[GPG-X1]$_{n1}$-GPS-(A)$_{n2}$}$_{n3}$(SEQ ID NO:115) (Equation 1)

X1=SGGQQ (SEQ ID NO: 116) or GAGQQ (SEQ ID NO: 117) or GQGPY (SEQ ID NO: 118) or AGQQ (SEQ ID NO: 119) or SQ (Equation 2)

In some embodiments, the silk or silk or silk-like proteins comprise quasi-repeat units as described by Equation 1 and Equation 2, wherein n1 is 4 or 5 for at least half of the quasi-repeat units. In some embodiments, the silk or silk or silk-like proteins comprise quasi-repeat units as described by Equation 1 and Equation 2, wherein n2 is from 5 to 8 for at least half of the quasi-repeat units.

The term "short quasi-repeat unit" as used herein refers to a repeat unit in which n1 is 4 or 5 (as shown in Equation 1). The term "long quasi-repeat unit" as used herein refers to a repeat in which n1 is 6, 7, or 8 (as shown in Equation 1). In some embodiments, n1 is from 4 to 5 for at least half of the quasi-repeat units. In some embodiments, n2 is from 5 to 8 for at least half of the quasi-repeat units. In some embodiments, the silk or silk or silk-like proteins comprise 3 "long quasi-repeat units" followed by 3 "short quasi-repeat units". In some embodiments, the silk or silk or silk-like proteins comprise quasi-repeat units that do not have the same $X_1$ motifs more than twice in a row, or more than 2 times, in a single quasi-repeat. In some embodiments, the silk or silk or silk-like proteins comprise quasi-repeat units that comprise the same $X_1$ motifs in the same location. In some embodiments, the silk or silk or silk-like proteins comprise quasi-repeat units that comprise the same Equation 2 sequence in the same location. In some embodiments, the silk or silk or silk-like proteins comprise quasi-repeat units wherein no more than 3 quasi-repeat units out of 6 share the same $X_1$.

In some embodiments, the silk or silk or silk-like proteins comprise Xqr quasi-repeat units, wherein $$Xqr=Xsqr+Xlqr \quad \text{(Equation 3)},$$

wherein Xqr is a number from 2 to 20; Xsgr is the number of short quasi-repeats, and a number from 1 to (Xqr-1); and Xlqr is the number of long quasi-repeats, and a number from 1 to (Xqr-1). In some embodiments, $X_qr$ is a number from 2 to 20. Non-limiting examples of amino acid sequences of repeat units are given in Table 3.

TABLE 3

Exemplary Repeat Units of Silk or Silk-Like Proteins

| SEQ ID NO | Sequence |
|---|---|
| 13 | GGYGPGAGQQGPGSGGQQGPGGQGPYGSGQQGPGGAGQQGPGGQGPYGPGAAAAAAAAGGYGPGAGQQGPG<br>GAGQQGPGSQGPGGQGPYGPGAGQQGPGSQGPGSGGQQGPGGQGPYGPSAAAAAAAAGGYGPGAGQRSQGPG<br>GQGPYGPGAGQQGPGSQGPGSGGQQGPGGQGPYGPSAAAAAAAAGGYGPGAGQQGPGSQGPGSGGQQGPGGQ<br>PYGPGAAAAAAAVGGYGPGAGQQGPGSQGPGSGGQQGPGGQGPYGPSAAAAAAAAGGYGPGAGQQGPGSQGP<br>GSGGQQGPGGQGPYGPSAAAAAAAA |
| 14 | GGQGGRGGFGGLGSQGAGGAGQGGAGAAAAAAAAGGDGGSGLGGYGAGRGHGVGLGGAGGAGAASAAAAAG<br>GQGGRGGFGGLGSQGAGGAGQGGAGAAAAAAAAGGDGGSGLGGYGAGRGHGAGLGGAGGAGAASAAAAAGG<br>QGGRGGFGGLGSQGSGGAGQGGSGAAAAAAAAGGDGGSGLGGYGAGRGYGAGLGGAGGAGAASAAAAAGGQ<br>GGRGGFGGLGSQGAGGAGQGGSGAAAAAAAAVADGGSGLGGYGAGRGYGAGLGGAGGAGAASAAAAT |
| 15 | GSAPQGAGGPAPQGPSQQGPVSQGPYGPGAAAAAAAAGGYGPGAGQQGPGSQGPGSGGQQGPGSQGPGSGGQQ<br>GPGGQGPYGPSAAAAAAAAGGYGPGAGQQGPGSQGPGSGGQQGPGGQGPYGPGAAAAAAAVGGYGPGAGQQ<br>GPGSQGPGSGGQQGPGGQGPYGPSAAAAAAAAGGYGPGAGQQGPGSQGPGSGGQQGPGGQGPYGPSAAAAAAA<br>AGGYGPGAGQQGPGSGGQQGPGGQGPYGSGQQGPGGAGQQGPGGQGPYGPGAAAAAAAA |
| 16 | GGYGPGAGQQGPGSGGQQGPGGQGPYGSGQQGPGGAGQQGPGGQGPYGPGAAAAAAAAGGYGPGAGQQGPG<br>GAGQQGPGSQGPGGQGPYGPGAGQQGPGSQGPGSGGQQGPGGQGPYGPSAAAAAAAAGGYGPGAGQQGPGSQG<br>PGSGGQQGPGGQGPYGPSAAAAAAAAGGYGPGAGQQGPGSGGQQGPGGQGPYGSGQQGPGGAGQQGPGGQP<br>YGGGYGPGAGQQGPGSQGPGSGGQQGPGGQGPYGPSAAAAAAAA |
| 17 | GPGARRQGPGSQGPGSGGQQGPGGQGPYGSGQQGPGGAGQQGPGGQGPYGPGAAAAAAAAGGYGPGAGQQG<br>PGGAGQQGPGSQGPGGQGPYGPGAGQQGPGSQGPGSGGQQGPGGQGPYGPSAAAAAAAAGGYGPGAGQQGPG<br>SQGPGSGGQQGPGGQGPYGPGAAAAAAAVGGYGPGAGQQGPGSQGPGSGGQQGPGGQGPYGPSAAAAAAAAG<br>GYGPGAGQQGPGSQGPGSGGQQGPGGQGPYGPSAAAAAAAA |
| 18 | GPGARRQGPGSQGPGSGGQQGPGGQGPYGSGQQGPGGAGQQGPGGQGPYGPGAAAAAAAAGGYGPGAGQQG<br>PGGAGQQGPGSQGPGGQGPYGPGAGQQGPGSQGPGSGGQQGPGGQGPYGPSAAAAAAAAGGYGPGAGQQGPGS<br>QGPGSGGQQGPGGQGPYGPGAAAAAAAVGGYGPGAGQQGPGSQGPGSGGQQGPGGQGPYGPSAAAAAAAAGG<br>YGPGAGQQGPGSQGPGSGGQQGPGGQGPYGPSAAAAAAAA |
| 19 | GGYGPGAGQQGPGSGGQQGPGGQGPYGSGQQGPGGAGQQGPGGQGPYGPGAAAAAAAAGGYGPGAGQQGPG<br>GAGQQGPEGPGSQGPGSGGQQGPGGQGPYGPGAAAAAAAVGGYGPGAGQQGPGSQGPGSGGQQGPGGQPYGP<br>SAAAAAAAAGGYGPGAGQQGPGSQGPGSGGQQGPGGQPYGPSAAAAAAAAGGYGPGAGQQGPGSGGQQGPG<br>GQGPYGSGQQGPGGAGQQGPGGQGPYGPGAAAAAAAA |

TABLE 3-continued

Exemplary Repeat Units of Silk or Silk-Like Proteins

| SEQ ID NO | Sequence |
|---|---|
| 20 | GVFSAGQGATPWENSQLAESFISRFLRFIGQSGAFSPNQLDDMSSIGDTLKTATEKMAQSRKSSKSKLQALNMAFAS SMAEIAVAEQGGLSLEAKTNAIASALSAAFLETTGYVNQQFVNEIKTLIFMIAQASSNEISGSAAAAGGSSGGGGGS GQGGYGQGAYASASAAAAYGSAPQGTGGPASQGPSQQGPVSQPSYGPSATVAVTAVGGRPQGPSAPRQQGPSQQ GPGQQGPGGRGPYGPSAAAAAAAA |
| 21 | GAGAGAGAGAGAGAGAGSGASTSVSTSSSSGSGAGAGAGSGAGSGAGAGSGAGAGAGAGGAGAGFGSGLGLGY GVGLSSAQAQAQAAAQAQAQAQAQAYAAAQAQAQAQAQAQAAAAAAAAAAAGAGAGAGAGAGAGAGAGAG SGASTSVSTSSSSGSGAGAGAGSGAGSGAGAGSGAGAGAGAGGAGAGFGSGLGLGYGVGLSSAQAQAQAQAAA QAQAQAQAQAYAAAQAQAQAQAQAAAAAAAAAAA |
| 22 | GAGAGAGAGAGAGAGSGASTSVSTSSSSGSGAGAGAGSGAGSGAGAGSGAGAGAGAGGAGAAFGSGLGLGY GVGLSSAQAQAQAAAQAQADAQAQAYAAAQAQAQAQAQAAAAAAAAAAAGAGAGAGAGSGAGAGAG SGASTSVSTSSSSGSGAGAGAGSGAGSGAGAGSGAGAGAGAGGAGAGFGSGLGLGYGVGLSSAQAQAQAAA QAQAQADAQAQAYAAAQAQAQAQAQAAAAAAAAAAA |
| 23 | GAGAGAGAGSGAGAGAGSGASTSVSTSSSSGSGAGAGAGSGAGSGAGAGSGAGAGAGAGGAGAGFGSGLGLGY GVGLSSAQAQAQSAAAARAQADAQAQAYAAAQAQAQAQAQAAAAAAAAAAAGAGAGAGAGAGAGAG SGASTSVSTSSSSASGAGAGAGSGAGSGAGAGSGAGAGAGAGGAGAGFGSGLGLGYGVGLSSAQAQAQAAA QAQAQAQAQALAAAQAQAQAQAQAAAATAAAAAA |
| 24 | GGYGPGAGQQGPGGAGQQGPGSQGPGGQGPYGPGAGQQGPGSQGPGSGGQQGPGGQGPYGPSAAAAAAAAGG YGPGAGQQGPGSQGPGSGGQQGPGSQGPGSGGQQGPGGQGPYGPSAAAAAAAAAGGYGPGAGQQGPGSQGPGS GGQQGPGGQGPYGPGAAAAAAAVGGYGPGAGQQGPGSQGPGSGGQQGPGGQGPYGPSAAAAAAAAGGYGPGA GQQGPGSQGPGSGGQQGPGGQGPYGPSAAAAAAAA |
| 25 | GGYGPGAGQQGPGGAGQQGPGSQGPGGQGPYGPGAGQQGPGSQGPGSGGQQGPGGQGPYGPSAAAAAAAAGG YGPGAGQQGPGSQGPGSGGQQGPGSQGPGSGGQQGPGGQGPYGPSAAAAAAAAAGGYGPGAGQQGPGSQGPGSG GQQGPGGQGPYGPGAAAAAAAVGGYGPGAGQQGPGSQGPGSGGQQGPGGQGPYGPSAAAAAAAAGGYGPGAG QQGPGSQGPGSGGQQGPGGQGPYGPSAAAAAAAA |
| 26 | GHQGPHRKTPWETPEMAENFMNNVRENLEASRIFPDELMKDMEAITNTMIAAVDGLEAQHRSSYASLQAMNTAF ASSMAQLFATEQDYVDTEVIAGAIGKAYQQITGYENPHLASEVTRLIQLFREEDDLENEVEISFADTDNAIARAAG AAAGSAAASSSADASATAEGASGDSGFLFSTGTFGRGGAGAGAGAAAASAAAASAAAAGAEGDRGLFFSTGDFG RGGAGAGAGAAAASAAAASAAAA |
| 27 | GGAQKHPSGEYSVATASAAATSVTSGGAPVGKPUPAPIFYPQGPLQQGPAPGPSNVQPGTSQQGPIGGVGESNTFS SSFASALGGNRGFSGVISSASATAVASAFQKGLAPYGTAFALSAASAAADAYNSIGSGASASAYAQAFARVLYPLL QQYGLSSSADASAFASAIASSFSTGVAGQGPSVPYVGQQQPSIMVSAASASAAASAAAVGGGPVVQGPYDGGQPQ QPNIAASAAAATATSS |
| 28 | GGQGGRGGFGGLGSQGEGGAGQGGAGAAAAAAAAAGADGGFGLGGYGAGRGYGAGLGGAGGAGAASAAAAAG GQGGRSGFGGLGSQGAGGAGQGGAGAAAAAAAAAGADGGSGLGGYGAGRGYGASLGGADGAGAASAAAAAGG QGGRGGFGGLGSQGAGGAGQGGAGAAAAAAAASGDGGSGLGGYGAGRGYGAGLGGAGGAGAASAAAAAGGE GGRGGFGGLGSQGAGGAGQGGSLAAAAAAAA |
| 29 | GPGGYGGPGQPGPGQGQYGPGPGQQGPRQGGQQGPASAAAAAAAGPGGYGGPGQQGPRQGQQQGPASAAAAA AAAAAAGPRGYGGPGQQGPVQGGQQGPASAAAAAAAAGVGGYGGPGQQGPGQGYGPGTGQQGQGPSGQQGPA GAAAAAAGGAAGPGGYGGPGQQGPGQGYGPGTGQQGQGPSGQQGPAGAAAAAAAAAGPGGYGGPGQQGPG QGQYGPGAGQQGPGSQQGPASAAAAAAA |
| 30 | GSGAGQGTGAGAGAAAAAGAAGSGAGQGAGSGAGAAAAAAASAAGAGQGAGSGSGAGAAAAAAAAAGAG QGAGSGSGAGAAAAAAAAAAAAQQQQQQAAAAAAAAAAAAAAGSGQGASFGVTQQFGAPSGAASSAAAAAA AAAAAAAGSGAGQEAGTGAGAAAAAAAAGAAGSGAGQGAGSGAGAAAAAAAAASAAGAGQGAGSGSGAGAA AAAAAAAAAQQQQQQAAAAAAAAAAAAAA |
| 31 | GGAQKQPSGESSVATASAAATSVTSAGAPVGKPGVPAPIFYPQGPLQQGPAPGPSYVQPATSQQGPIGGAGRSNAFS SSFASALSGNRGFSEVISSASATAVASAFQKGLAPYGTAFALSAASAAADAYNSIGSGANAFAYAQAFARVLYPLV QQYGLSSSAKASAFASAIASSFSSGAAGQGQSIPYGGQQQPPMTISAASASAGASAAAVKGGQVGQGPYGGQQQST AASASASAAATTATA |
| 32 | GADGGSGLGGYGAGRGYGAGLGGADGAGAASAAAAAGGQGGRGGFGRLGSQGAGGAGQGGAGAAAAVAAAG GDGGSGLGGYGAGRGYGAGLGGAGGAGAASAAAAAGGQGGRGGFGGLGSQGAGGAGQGGAGAAASGDGGSG LGGYGAGRGYGAGLGGADGAGAASAASAAGGQGGRGGFGGLGSQGAGGAGQGGAGAAAAAATAGGDGGSGL GGYGAGRGYGAGLGGAGGAGAASAAAAA |
| 33 | GAGAGQGGRGGYGQGGFGGQGSGAGAGASAAAGAGAGQGGRGGYGQGGFGGQGSGAGAGASAAAGAGAGQG GRGGYGQGGFGGQGSGAGAGASAAAAGAGQGGRGGYGQGGLGGSGSGAGAGAGAAAAAAGAGGYGQGGL GGYGQGAGAGQGGLGGYGSGAGAGASAAAAGAGGAGQGGLGGYGQGAGAGQGGLGGYGSGAGAGAAAAA AAGAGGSGQGGLGGYGSGGGAGGASAAAA |

TABLE 3-continued

Exemplary Repeat Units of Silk or Silk-Like Proteins

| SEQ ID NO | Sequence |
|---|---|
| 34 | GAYAYAYAIANAFASILANTGLLSVSSAASVASSVASAIATSVSSSSAAAAASASAAAAASAGASAASSASASSSAS AAAGAGAGAGAGASGASGAAGGSGGFGLSSGFGAGIGGLGGYPSGALGGLGIPSGLLSSGLLSPAANQRIASLIPLI LSAISPNGVNFGVIGSNIASLASQISQSGGGIAASQAFTQALLELVAAFIQVLSSAQIGAVSSSSASAGATANAFAQSL SSAFAG |
| 35 | GAAQKQPSGESSVATASAAATSVTSGGAPVGKPGVPAPIFYPQGPLQQGPAPGPSNVQPGTSQQGPIGGVGGSNAF SSSFASALSLNRGFTEVISSASATAVASAFQKGLAPYGTAFALSAASAAADAYNSIGSGANAFAYAQAFARVLYPLV RQYGLSSSGKASAFASAIASSFSSGTSGQGPSIGQQQPPVTISAASASAGASAAAVGGGQVGQGPYGGQQQSTAASA SAAAATATS |
| 36 | GAAQKQPSGESSVATASAAATSVISGGAPVGKPGVPAPIFYPQGPLQQGPAPGPSNVQPGTSQQGPIGGVGGSNAF SSSFASALSLNRGFTEVISSASATAVASAFQKGLAPYGTAFALSAASAAADAYNSIGSGANAFAYAQAFARVLYPLV RQYGLSSSGKASAFASAIASSFSSGTSGQGPSIGQQQPPVTISAASASAGASAAAVGGGQVGQGPYGGQQQSTAASA SAAAATATS |
| 37 | GAAQKQPSGESSVATASAAATSVTSGGAPVGKPGVPAPIFYPQGPLQQGPAPGPSNVQPGTSQQGPIGGVGGSNAF SSSFASALSLNRGFTEVISSASATAVASAFQKGLAPYGTAFALSAASAAADAYNSIGSGANAFAYAQAFARVLYPLV QQYGLSSSAKASAFASAIASSFSSGTSGQGPSIGQQQPPVTISAASASAGASAAAVGGGQVGQGPYGGQQQSTAAS ASAAAATATS |
| 38 | GGAQKQPSGESSVATASAAATSVTSAGAPVGKPGVPAPIFYPQGPLQQGPAPGPSNVQPGTSQQGPIGGVGGSNAF SSSFASALSLNRGFTEVISSASATAVASAFQKGLAPYGTAFALSAASAAADAYNSIGSGANAFAYAQAFARVLYPLV QQYGLSSSAKASAFASAIASSFSSGTSGQGPSNGQQQPPVTISAASASAGASAAAVGGGQVSQGPYGGQQQSTAAS ASAAAATATS |
| 39 | GGAQKQPSGESSVATASAAATSVTSAGAPGGKPGVPAPIFYPQGPLQQGPAPGPSNVQPGTSQQGPIGGVGGSNAF SSSFASALSLNRGFTEVISSASATAVASAFQKGLAPYGTAFALSAASAAADAYNSIGSGANAFAYAQAFARVLYPLV QQYGLSSSAKASAFASAIASSFSSGTSGQGPSIGQQQPPVTISAASASAGASAAAVGGGQVGQGPYGGQQQSTAAS ASAAAATATS |
| 40 | GPGGYGGPGQQGPGQGQQQGPASAAAAAAAAGPGGYGGPGQQGPGQGQQQGPASAAAAAAAAAGPGGYGGPG QQRPGQAQYGRGTGQQGQGPGAQQGPASAAAAAAAAGAGLYGGPGQQGPGQGQQQGPASAAAAAAAAAAGP GYGGPGQQGPGQAQQQGPASAAAAAAAAGPGGYSGPGQQGPGQAQQQGPASAAAAAAAAAGPGGYGGPGQQGP GQGQQQGPASAAAAAAATAA |
| 41 | GAGGDGGLFLSSGDFGRGGAGAGAGAAAASAAAASSAAAGARGGSGFGVGTGGFGRGGAGDGASAAAASAAA ASAAAAGAGGDSGLFLSSGDFGRGGAGAGAGAAAASAAAASAAAAGTGGVGGLFLSSGDFGRGGAGAGAGAA ASAAAASSAAAGARGGSGFGVGTGGFGRGGPGAGTGAAAASAAAASAAAAGAGGDSGLFLSSEDFGRGGAGAG TGAAAASAAAASAAAA |
| 42 | GAGRGYGGGYGGGAAAGAGAGAGAGRGYGGGYGGGAGSGAGSGAGAGGGSGYGRGAGAGAGAGAAAAGA GAGGAGGYGGGAGAGAGASAAAGAGAGAGGAGGYGGGYGGGAGAGAGAGAAAAAGAGAGAGAGRGYGGGF GGGAGSGAGAGAGGGSGYGRGAGGYGGGYGGGAGTGAGAAAATGAGAGAGAGRGYGGGYGGGAGAGAG AGAGAGGGSGYGRGAGAGASVAA |
| 43 | GALGQGASVWSSPQMAENFMNGFSMALSQAGAFSGQEMKDFDDVRDIMNSAMDKMIRSGKSGRGAMRAMNAA FGSAIAEIVAANGGKEYQIGAVLDAVTNTLLQLTGNADNGFLNEISRLITLFSSVEANDVSASAGADASGSSGPVGG YSSGAGAAVGQGTAQAVGYGGGAQGVASSAAAGATNYAQGVSTGSTQNVATSTVTTTTNVAGSTATGYNTGYG IGAAAGAAA |
| 44 | GGQGGQGGYDGLGSQGAGQGGYGQGGAAAAAAAASGAGSAQRGGLGAGGAGQGYGAGSGGQGGAGQGGAA AATAAAAGGQGGQGGYGGLGSQGSGQGGYGQGGAAAAAAAASGDGGAGQEGLGAGGAGQGYGAGLGGQGG AGQGGAAAAAAAAAGGQGGQGGYGGLGSQGAGQGGYGQGGAAAAAAAASGAGGAGQGGLGAAGAGQGYGA GSGGQGGAGQGGAAAAAAAA |
| 45 | GGQGGQGGYGGLGSQGAGQGGYGQGGVAAAAAAASGAGGAGRGGLGAGGAGQEYGAVSGGQGGAGQGGEA AAAAAAAGGQGGQGGYGGLGSQGAGQGGYGQGGAAAAAAAASGAGGARRGGLGAGGAGQGYGAGLGGQGG AGQGSASAAAAAAAAGGQGGQGGYGGLGSQGSGQGGYGQGGAAAAAAAASGAGGAGRGSLGAGGAGQGYGAG LGGQGGAGQGGAAAAASAAA |
| 46 | GPGGYGGPGQQGPGQGQYGPGTGQQGQGPGGQQGPVGAAAAAAAVSSGGYGSQGAGQGGQQGSGQRGPAAA GPGGYSGPGQQGPGQGQQQGPASAAAAAAAAGPGGYGGSGQQGPGQGRGTGQQGQGPGGQQGPASAAAAAA AGPGGYGGPGQQGPGQGQYGPGTGQQGQGPASAAAAAAAAGPGGYGGPGQQGPGQGQYGPGTGQQGQGPGGQQ GPGGASAAAAAAA |
| 47 | GGYGPGAGQQGPGSGQQGPGGQGPYGSGQQGPGGAGQQGPGGQGPYGPAAAAAAAAAGGYGPGAGQQGPG GAGQQGPGSQGPGGQGPYGPGAGQQGPGSQGPGSGQQGPGGQGPYGPSAAAAAAAAAGGYGPGAGQRSQGPG GQGPYGPGAGQQGPGSQGPGSGQQGPGGQGPYGPSAAAAAAAAGPGAGRQGPGSQGPGSGQQGPGGQGPYG PSAAAAAAAA |
| 48 | GQGGQGGQGGLGQGGYGQGAGSSAAAAAAAAAAAAAGRGQGGYGQGSGGNAAAAAAAAAAAASGQGSQG GQGGQGQGGYGQGAGSSAAAAAAAAAAAASGRGQGGYGQGAGGNAAAAAAAAAAAAAGQGGQGGYGGL GQGGYGQGAGSSAAAAAAAAAAAAGGQGGQGGYGQGSGGSAAAAAAAAAAAAAAGRGQGGYGQGSGG NAAAAAAAAAAAA |

TABLE 3-continued

Exemplary Repeat Units of Silk or Silk-Like Proteins

| SEQ ID NO | Sequence |
|---|---|
| 49 | GRGPGGYGPGQQGPGGPGAAAAAAAGPGGYGPGGYGPGQQGPGGPGAAAAAAAGRGPGGYGPGQQGPGQQGPG GSGAAAAAAAGRGPGGYGPGQQGPGGPGAAAAAAAGPGGYGPGQQGPGAAAAAAAAGRGPGGYGPGQQGPGGPG AAAAAAAGRGPGGYGPGQQGPGQQGPGGSGAAAAAAAGRGPGGYGPGQQGPGGPGAAAAAAAGPGGYGPGQQGP GAAAAAAAA |
| 50 | GRGPGGYGPGQQGPGGSGAAAAAAAGRGPGGYGPGQQGPGGPGAAAAAAAGPGGYGPGQQGTGAAAAAAAGSGA GGYGPGQQGPGGPGAAAAAAAGPGGYGPGQQGPGAAAAAAAAGSGPGGYGPGQQGPGGSSAAAAAAAGPGRYGPG QQGPGAAAAAASAGRGPGGYGPGQQGPGGPGAAAAAAAGPGGYGPGQQGPGAAAAAAAAGSGPGGYGPGQQGPGG PGAAAAAAA |
| 51 | GAAATAGAGASVAGGYGGGAGAAAGAGAGGYGGGYGAVAGSGAGAAAAASSGAGGAAGYGRGYGAGSGAG AGAGTVAAYGGAGGVATSSSSATASGSRIVTSGGYGYGTSAAAGAGVAAGSYAGAVNRLSSAEAASRVSSNIAAI ASGGASALPSVISNIYSGVVASGVSSNEALIQALLELLSALVHVLSSASINVSSVGVDSTLN1VVQDSVGQYVG |
| 52 | GGQGGFSGQGQGGFGPGAGSSAAAAAAAAAAAARQGGQGGGFGQGAGGNAAAAAAAAAAAAAAQQGGQGGF SGRGQGGFGPGAGSSAAAAAAGQGGQGGFGQGAGGNAAAAAAAAAAAAAAAQGGQGGRGGFGQGAGGNA AAAAAAAAAAAAAQQGGQGGFGGRGQGGFGPGAGSSAAAAAAAGQGGQGRGGFGQGAGGNAAAASAAAAAS AAAAGQ |
| 53 | GGYGPGAGQQGPGGAGQQGPGSGQPGGAGQQGPGGQGPYGPGAAAAAAAVGGYGPGAGQQGPGSQGPGSGGQ QGPGGQGPYGPSAAAAAAAGGYGPGAGQQGPGSQGPGSGGQQGPGGLGPYGPSAAAAAAAAGGYGPGAGQQ GPGSQGPGSGGQQRPGGLGPYGPSAAAAAAAAGGYGPGAGQQGPGSQGPGSGGQQRPGGLGPYGPSAAAAAAA A |
| 54 | GAGAGGGYGGGYSAGGGAGAGSGAAAGAGAGRGGAGGYSAGAGTGAGAAAGAGTAGGYSGGYGAGAGASSSAG SSFISSSSMSSSQATGYSSSSGYGGGAASAAAGAGAAAGGYGGGYGAGAGAGAAAASGATGRVANSLGAMASGG INALPGVFSNIFSQVSAASGGASGGAVLVQALTEVIALLLHILSSASIGNVSSQGLEGSMAIAQQAIGAYAG |
| 55 | GAGAGGAGGYAQGYGAGAGAGAGAGTGAGGAGGYGQGYGAGSGAGAGGAGGYGAGAGAGAGAGDASGYGQ GYGDGAGAGAAAAAGAAAGARGAGGYGGGAGAGAGAGAGAAGGYGQGYGAGAGEGAGAGAGAVAG AGAAAAAGAGAGAGGAEGYGAGAGAGGAGGYGQSYGDGAAAAAGSGAGAGGSGGYGAGAGAGSGAGAAGG YGGGAGA |
| 56 | GPGGYGPGQQGPGGYGPGQQGPGRYGPGQQGPSGPGSAAAAAAGSGQQGPGGYGPGRQQGPGGYGQGQQGPSGP GSAAAASAAASAESGQQGPGGYGPGQQGPGGYGPGQQGPGGYGPGQQGPSGPGSAAAAAAAASGPGQQGPGGY GPGQQGPGGYGPGQQGPSGPGSAAAAAAAASGPGQQGPGGYGPGQQGPGGYGPGQQGLSGPGSAAAAAAA |
| 57 | GRGPGGYGQGQQGPGGPGAAAAAAAGPGGYGPGQQGPGAAAAAAAGSGPGGYGPGQQGPGRSGAAAAAAAAGR GPGGYGPGQQGPGGPGAAAAAAAGPGGYGPGQQGPGAAAASAGRGPGGYGPGQQGPGGSGAAAAAAGRGPGG YGPGQQGPGGPGAAAAAAAGRGPGGYGPGQQGPGQQGPGGSGAAAAAAAGRGPGGYGPGQQGPGGPGAAAAAA |
| 58 | GVGAGGEGGYDQGYGAGAGAGSGGGAGGAGGYGGGAGAGSGGGAGGAGGYGGGAGAGAGAGAGGAGGYGG GAGAGTGARAGAGGVGGYGQSYGAGASAAAAGAGVGAGGAGAGGAGGYGQGYGAGAGIGAGDAGGYGGGAG AGASAGAGGYGGGAGAGAGGVGGYGKGYGAGSGAGAAAAAGAGAGSAGGYGRGDGAGAGGASGYGQGYGA GAAA |
| 59 | GYGAGAGRGYGAGAGAGAGAVAASGAGAGAGAGYGAGAGAGAGAGYGAGAGRGYGAGAGAGAGSGAASGAGA GAGYGAGAGAGYGAGAGSGYGTGAGAGAGAAAGGAGAGAGYGAGAGRGYGAGAGAGAASGAGAGAGA GAASGAGAGSGYGAGAAAGGAGAGAGGGYGAGAGRGYGAGAGAGAGSGSGSAAGYGQGYGSGSGAGAA A |
| 60 | GQGTDSSASSVSTSTSVSSSATGPDTGYPVGYYGAGQAEAAASAAAAAAASAAEEAATIAGLGYGRQGQGTDSSAS SVSTSTSVSSSATGPDMGYPVGNYGAGQAEAAASAAAAAAASAAEEAATIASLGYGRQGQGTDSSASSVSTSTSVSS SATGPGSRYPVRDYGADQAEAAASAAAAAAAAASAAEEIASLGYGRQ |
| 61 | GQGTDSVASSASSSASASSSATGPDTGYPVGYYGAGQAEAAASAAAAAAASAAEAATIAGLGYGRQGQGTDSSAS SVSTSTSVSSSATGPGSRYPYRDYGADQAEAAASATAAAAAAAASAAEEIASLGYGRQGQGTDSVASSASSSASASS SATGPDTGYPVGYYGAGQAEAAASAAAAAAASAAEEAATIAGLGYGRQ |
| 62 | GQGGQGGYGGLGQGGYGQGAGSSAAAAAAAAAAAAGGQGGQGQGRYGQGAGSSAAAAAAAAAAAAAAGR GQGGYGQGSGGNAAAAAAAAAAAAASGQGSQGGQGGQGGYGQGAGSSAAAAAAAAAAAAAASGRGQGGYG QGAGGNAAAAAAAAAAAAAAAGQGGQGGYGGLGQGGYGQGAGSSAAAAAAAAAAAA |
| 63 | GGLGQGGLGGLGSQGAGLGGYGQGGAGQGGAAAAAAAAGGLGQGGRGGLGSQGAGQGGYGQGGAGQGG AAAAAAAAAGGLGQGGLGALGSQGAGQGGAGQGGYGQGGAAAAAAAGGLGQGGLGGLGSQGAGQGGYGQG GAGQGGAAAAAAAAGGLGQGGLGGLGSQGAGPGGYGQGGAGQGGAAAAAAAA |
| 64 | GGQGRGGFGQGAGGNAAAAAAAAAAAAAAAQQVGQFGFGGRGQGGFGPFAGSSAAAAAAAASAAAGQGGQGQG GFGQGAGGNAAAAAAAAAAAAAARQGGQGGGFSQGAGGNAAAAAAAAAAAAAAAQQGGQGGFGGRGQGGFGP GAGSSAAAAAAATAAAGQGGQGRGGFGQGAGSNAAAAAAAAAAAAAAAGQ |
| 65 | GGQGGQGGYGGLGSQGAGQGGYGAGQGAAAAAAAAGGAGGAGRGGLGAGGAGQGYGAGLGGQGGAGQGAAA AAAAGGAGGARQGGLGAGGAGQGYGAGLGGQGGAGQGGAAAAAAAAGGQGGQGGYGGLGSQGAGQGGYGA GQGGAAAAAAAAGGQGGQGGYGGLGSQGAGQGGYGGRQGGAGAAAAAAAA |

TABLE 3-continued

Exemplary Repeat Units of Silk or Silk-Like Proteins

| SEQ ID NO | Sequence |
|---|---|
| 66 | GGAGQRGYGGLGNQGAGRGGLGGQGAGAAAAAAGGAGQGGYGGLGNQGAGRGGQGAAAAAGGAGQGGYG GLGSQGAGRGGQGAGAAAAAAVGAGQEGIRGQGAGQGGYGGLGSQGSGRGGLGGQGAGAAAAAAGGAGQGG LGGQGAGQGAGAAAAAAGGVRQGGYGGLGSQGAGRGGQGAGAAAAAA |
| 67 | GGAGQGGLGGQGAGQGAGASAAAAGGAGQGGYGGLGSQGAGRGGEGAGAAAAAAGGAGQGGYGGLGGQGA GQGGYGGLGSQGAGRGGLGGQGAGAAAAGGAGQGGLGGQGAGQGAGAAAAAAGGAGQGGYGGLGSQGAGR GGLGGQGAGAVAAAAGGAGQGGYGGLGSQGAGRGGQGAGAAAAAA |
| 68 | GAGAGAGAGSGAGAAGGYGGGAGAGVGAGGAGGYDQGYGAGAGAGSGAGAGGAGGYGGGAGAGADAGAG GAGGYGGGAGAGAGARAGAGGVGGYGQSYGAGAGAGAGVGAGGAGAGGADGYGQGYGAGAGTGAGDAGG YGGGAGAGASAGAGGYGGGAGAGGVGVYGKGYGSGSGAGAAAA |
| 69 | GGAGGYGVGQGYGAGAGAGAAAGAGAGGAGGYGAGQGYGAGAGVGAAAAAGAGAGVGGAGGYGRGAGAG AGAGAGAAAGAGAGAAAGAGAGGAGGYGAGQGYGAGAGVGAAAAAGAGAGVGGAGGYGRGAGAGAGAGA GGAGGYGRGAGAGAGAGAGGAGGYGAGQGYGAGAGAGAAAA |
| 70 | GEAFSASSASSASSAVVFESAGPGEEAGSSGDGASAAASAAAAAGAGSGRRGPGGARSRGGAGAGAGAGSGVGGYGS GSGAGAGAGAGAGAGGEGGFGEGQGYGAGAGAGFGSGAGAGAGAGSGAGAGEGVGSGAGAGAGAGFGVGAG AGAGAGAGFGSGAGAGSGAGAGYGAGRAGGRGRGGRG |
| 71 | GEAFSASSASSASSAVVFESAGPGEEAGSSGGGASAAASAAAAAGAGSGRRGPGGARSRGGAGAGAGAGSGVGGYGS GSGAGAGAGAGAGAGGEGGFGEGQGYGAGAGAGFGSGAGAGAGAGSGAGAGEGVGSGAGAGAGAGFGVGAG AGAGAGAGFGSGAGAGSGAGAGYGAGRAGGRGRGGRG |
| 72 | GNGLGQALLANGVLNSGNYLQLANSLAYSFGSSLSQYSSSAAGASAAGAASGAAGAGAGAASSGGSSGSASSSTT TITTTSTSAAAAAAAAAAAASAAASTSASASASASASASAFSQTFVQTVLQSAAFGSYFGGNLSLQSAQAAASAAA QAAAQQIGLGSYGYALANAVASAFASAGANA |
| 73 | GNGLGQALLANGVLNSGNYLQLANSLAYSFGSSLSQYSSSAAGASAAGAASGAAGAGAGAASSGGSSGSASSSTT TTTTTSTSAAAAAAAAAAAASAAASTSASASASASASASAFSQTFVQTVLQSAAFGSYFGGNLSLQSAQAAASAAA QAAAQQIGLGSYGYALANAVASAFASAGANA |
| 74 | GNGLGQALLANGVLNSGNYLQLANSLAYSFGSSLSQYSSSAAGASAAGAASGAAGAGAGAASSGGSSGSASSSTT TTTITSTSAAAAAAAAAAAASAAASTSASASASASASASAFSQTFVQTVLQSAAFGSYFGGNLSLQSAQAAASAAA QAAAQQIGLGSYGYALANAVASAFASAGANA |
| 75 | GASGAGQGQGYGQQGQGGSSAAAAAAAAAAAAAAAQGQGQGYGQQGQGSAAAAAAAAAAAGASGAGQGQGY GQQGQGSAAAAAAAAAAAGASGAGQGQGYGQQGQGGSSAAAAAAAAAAAAAAAQGQGYGQQGQGSAAAAA AAAAGASGAGQGQGYGQQGQGGSSAAAAAAAAAAAAAAA |
| 76 | GRGQGGYGQGSGGNAAAAAAAGQGGFGGQEGNGQGAGSAAAAAAAAAAAAGGSGQGRYGGRGQGGYGQGA GAAASAAAAAAAAAGQGGFGGQEGNGQGAGSAAAAAAAAAAAAGGSGQGGYGGRGQGGYGQGAGAAAAA AAAAAAAAGQGGQGGFGSQGGNGQGAGSAAAAAAAAAA |
| 77 | GQNTPWSSTELADAFINAFMNEAGRTGAFTADQLDDMSTIGDTIKTAMDKMARSNKSSKGKLQALNMAFASSMA EIAAVEQGGLSVDAKTNAIADSLNSAFYQTTGAANPQFVNEIRSLINMFAQSSANEVSYGGGYGGQSAGAAASAAA AGGGGQGGYGNLGGQGAGAAAAAASAA |
| 78 | GQNTPWSSTELADAFINAFLNEAGRTGAFTADQLDDMSTIGDTLKTAMDKMARSNKSSQSKLQALNMAFASSMA EIAAVEQGGLSVAEKTNAIADSLNSAFYQTTGAVNVQFVNEIRSLISMFAQASANEVSYGGGYGGGQGGQSAGAA AAAASAGAGQGGYGGLGGQGAGSAAAAAA |
| 79 | GGQGGQGGYGGLGSQGAGQGGYGQGGAAAAAASAGGQGGQGGYGGLGSQGAGQGGYGGGAFSGQQGGAASV ATASAAASRLSSPGAASRVSSAVTSLVSSGGPTNSAALSNTISNVVSQISSSNPGLSGCDVLVQALLEIVSALVHILGS ANIGQVNSSGVGRSASIVGQSINQAFS |
| 80 | GGAGQGGYGGLGGQGAGAAAAAAGGAGQGGYGGQGAGQGAAAAAASGAGQGGYEGPGAGQGAGAAAAAAG GAGQGGYGGLGGQGAGQGAGAAAAAAGGAGQGGYGGLGGQGAGQGAGAAAAAAGGAGQGGYGGQGAGQG AAAAAAGGAGQGGYGGLGSQGGYGRQGAGAAAAAAA |
| 81 | GASSAAAAAAATATSGGAPGGYGGYGPGIGGAFVPASTTGTGSGSGSGAGAAGSGGLGGLGSSGGSGGLGGGNG GSGASAAASAAAASSSPGSGGYGPGQGVGSGSGSGAAGGSGTGSGAGGPGSGGYGGPQFFASAYGGQGLLGTSG YGNGQGGASGTGSGGVGGSGSGAGSNS |
| 82 | GQPIWTNPNAAMTMTNNLVQCASRSGVLTADQMDDMGMMADSVNSQMQKMGPNPPQHRLRAMNTAMAAEVA EVVATSPPQSYSAVLNTIGACLRESMMQATGSVDNAFTNEVMQLVKMISADSANEVSTASASGASYATSTSSAVS SSQATGYSTAAGYGNAAGAGAGAAAAVS |
| 83 | GQKIWTNPDAAMAMTNNLVQCAGRSGALTADQMDDLGMVSDSVNSQVRKMGANAPPHKIKAMSTAVAAGVAE VVASSPPQSYSAVLNTIGGCLRESMMQTGSVDNTFTTEMMQMVNMFAADNANEVSASASGSGASYATGTSSAV STSQATGYSTAGGYGTAAGAGAGAAAA |
| 84 | GSGYGAGAGAGAGSGYGAGAGAGSGYGAGAGAGAGSGYVAGAGAGAGAGSGYGAGAGAGAGSSYSAGAGAG AGSGYGAGSSASAGSAVSTQTVSSSATTSSQSAAAATGAAYGTRASTGSGASAGAAASGAGAGYGGQAGYGQGG GAAAYRAGAGSQAAYGQGASGSSGAAAAA |

TABLE 3-continued

Exemplary Repeat Units of Silk or Silk-Like Proteins

| SEQ ID NO | Sequence |
|---|---|
| 85 | GGQGGRGGFGGLSSQGAGGAGQGGSGAAAAAAAGGDGGSGLGDYGAGRGYGAGLGGAGGAGVASAAASAA<br>ASRLSSPSAASRVSSAVTSLISGGGPTNPAALSNTFSNVVYQISVSSPGLSGCDVLIQALLELVSALVHILGSAIIGQVN<br>SSAAGESASLVGQSVYQAFS |
| 86 | GVGQAATPWENSQLAEDFINSFLRFIAQSGAFSPNQLDDMSSIGDTLKTAIEKMAQSRKSSKSKLQALNMAFASSM<br>AEIAVAEQGGLSLEAKTNAIANALASAFLETTGFVNQQFVSEIKSLIYMIAQASSNEISGSAAAAGGGSGGGGSGQ<br>GGYGQGASASASAAAA |
| 87 | GGGDGYGQGGYGNQRGVGSYGQGAGAGAAATSAAGGAGSGRGGYGEQGGLGGYGQGAGAGAASTAAGGGDG<br>YGQGGYGNQGGRGSYGQGSGAGAGAAVAAAAGGAVSGQGGYDGEGGQGGYGQGSGAGAAVAAASGGTGAGQ<br>GGYGSQGSQAGYGQGAGFRAAAATAAA |
| 88 | GAGAGYGGQVGYGQGAGASAGAAAAGAGAGYGGQAGYGQGAGGSAGAAAAGAGAGRQAGYGQGAGASARA<br>AAAGAGTGYGQGAGASAGAAAAGAGAGSQVGYGQGAGASSGAAAAAGAGAGYGGQVGYEQGAGASAGAEAA<br>ASSAGAGYGGQAGYGQGAGASAGAAAA |
| 89 | GGAGQGGYGGLGGQGAGQGGLGGQRAGAAAAAAGGAGQGGYGGLGSQGAGRGGYGGVGSGASAASAAASRL<br>SSPEASSRVSSAVSNLVSSGPTNSAALSSTISNVVSQISASNPGLSGCDVLVQALLEVVSALIQILGSSSIGQVNYGTA<br>GQAAQIVGQSVYQALG |
| 90 | GGYGPGSGQQGPGGAGQQGPGGQGPYGPGSSSAAAVGGYGPSSGLQGPAGQGPYGPGAAASAAAAAGASRLSSP<br>QASSRVSSAVSSLVSSGPTNSAALTNTISSVVSQISASNPGLSGCDVLIQALLEIVSALVHILGYSSIGQINYDAAAQY<br>ASLVGQSVAQALA |
| 91 | GGAGAGQGSYGGQGGYGQGGAGAATATAAAAGGAGSGQGGYGGQGGLGGYGQGAGAGAAAAAAAAGGAG<br>AGQGGYGGQGGQGGYGQGAGAGAAAAAGGAGAGQGGYGGQGGYGQGGGAGAAAAAAAASGGSGSGQGGY<br>GGQGGLGGYGQGAGAGAGAAASAAAA |
| 92 | GQGGQGGYGRQSQGAGSAAAAAAAAAAAAGSGQGGYGGQGQGGYGQSSASASAAASAASTVANSVSRLSSP<br>SAVSRVSSAVSSLVSNGQVNMAALPNIESNISSSVSASAPGASGCEVIVQALLEVITALVQIVSSSSVGY1NPSAVNQIT<br>NVVANAMAQVMG |
| 93 | GGAGQGGYGGLGGQGSGAAAAGTGQGGYGSLGGQGAGAAGAAAAAVGGAGQGGYGGVGSAAASAAASRLSSP<br>EASSRVSSAVSNLVSSGPTNSAALSNTISNVVSQISSSNPGLSGCDVLVQALLEVVSALIHILGSSSIGQVNYGSAGQA<br>TQIVGQSVYQALG |
| 94 | GAGAGGAGGYGAGQGYGAGAGAGAAAGAGAGGARGYGARQGYGSGAGAGAGARAGGAGGYGRGAGAGAAA<br>ASGAGAGGYGAGQGYGAGAGAVASAAAGAGSGAGGAGGYGRGAGAVAGAGAGGAGGYGAGAGAAAGVGAG<br>GSGGYGGRQGGYSAGAGAGAAAA |
| 95 | GQGGQGGYGGLGGQGYGQGAGSSAAAAAAAAAAAGRGQGGYGQGSGGNAAAAAAAAAAAASGQGGQGGQG<br>GGQGGYGQGAGSSAAAAAAAAAAAAAAAGRGQGGYGQGAGGNAAAAAAAAAAAASGQGGQGGQGGQG<br>GYGQGAGSSAAAAAAAAAAAAAA |
| 96 | GGYGPGSGQQGPGQQGPGQQGPGQQGPYGAGASAAAAAAGGYGPGSGQQGPGVRVAAPVASAAASRLSSSAAS<br>SRVSSAVSSLVSSGPTTPAALSNTISSAVSQISASNPGLSGCDVLVQALLEVVSALVHILGSSSVGQINYGASAQYAQ<br>MVGQSVTQALV |
| 97 | GAGAGGAGYGRGAGAGAAAGAGAGAAAGAGAGAGGYGGQGGYGAGAGAGAAAAGAGAGGAAGYSRG<br>GRAGAAGAGAAAGAGAGAGGYGGQGGYGAGAGAGAAAAAGAGSGGAGGYGRGAGAGAAAGAGAAAGA<br>GAGAGGYGGQGGYGAGAGAAAAA |
| 98 | GAGAGRGGYGRGAGAGGYGGQGGYGAGAGAGAAAAAGAGAGGYGDKEIACWSRCRYTVASTTSRLSSAEASS<br>RISSAASTLVSGGYLNTAALPSVISDLFAQVGASSPGVSDSEVLIQVLLEIVSSLIHILSSSSVGQVDFSSVGSSAAAVG<br>QSMQVVMG |
| 99 | GAGAGAGGAGGYGRGAGAGAGAGAAAGQGYGSGAGAGAGASAGGAGSYGRGAGAGAAAASGAGAGGYG<br>AGQGYGAGAGAVASAAAGAGSGAGGAGGYGRGAVAGSGAGAGAGAGGAGGYGAGAGAGAAAGAVAGGSGG<br>YGGRQGGYSAGAGAGAAAA |
| 100 | GPGGYGPVQQGPSGPGSAAGPGGYGPAQQGPARYGPGSAAAAAAAAGSAGYGPGPGQASAAAASRLASPDSGARVA<br>SAVSNLVSSGPTSSAALSSVISNAVSQIGASNPGLSGCDVLIQALLEIVSACVTILSSSSIGQVNYGAASQFAQVVGQS<br>VLSAFS |
| 101 | GTGGVGGLFLSSGDFGRGGAGAGAGAAAASAAAASSAAAGARGGSGFGVGTGGFGRGGAGAGTGAAAASAAAA<br>SAAAAGAGGDGGLFLSSGDFGRGGAGAGAGAAAASAAAASSAAAGARGGSGFGVGTGGFGRGGAGDGASAAA<br>ASAAAASAAAA |
| 102 | GGYGPGAGQQGPGGAGQQGPGGQGPYGPSVAAAASAAGGYGPGAGQQGPVASAAVSRLSSPQASSRVSSAVSSL<br>VSSGPTNPAALSNAMSSVVSQVSASNPGLSGCDVLVQALLEIVSALVHILGSSSIGQINYAASSQYAQMVGQSVAQA<br>LA |

TABLE 3-continued

Exemplary Repeat Units of Silk or Silk-Like Proteins

| SEQ ID NO | Sequence |
|---|---|
| 103 | GGAGQGGYGGLGSQGAGRGGYGGQGAGAAAAATGGAGQGGYGGVGSGASAASAAASRLSSPQASSRVSSAVSN LVASGPTNSAALSSTISNAVSQIGASNPGLSGCDVLIQALLEVVSALIHILGSSSIGQVNYGSAGQATQIVGQSVYQAL G |
| 104 | GGAGQGGYGGLGSQGAGRGGYGGQGAGAAVAAIGGVGQGGYGGVGSGASAASAAASRLSSPEASSRVSSAVSN LVSSGPTNSAALSSTISNVVSQIGASNPGLSGCDVLIQALLEVVSALVHILGSSSIGQVNYGSAGQATQWGQSVYQA LG |
| 105 | GASGGYGGGAGEGAGAAAAAGAGAGGAGGYGGGAGSGAGAVARAGAGGAGGYGSGIGGGYGSGAGAAAGAG AGGAGAYGGGYGTGAGAGARGADSAGAAAGYGGGVGTGTGSSAGYGRGAGAGAGAGAAAGSGAGAAGGYGG GYGAGAGAGA |
| 106 | GAGSGQGGYGGQGGLGGYGQGAGAGAAAGASGSGSGGAGQGGLGGYGQGAGAGAAAAAGASGAGQGGFGP YGSSYQSSTSYSVTSQGAAGGLGGYGQGSGAGAAAAGAAGQGGQGGYGQGAGAGAGAGAGQGGLGGYGQGA GSSAASAAAA |
| 107 | GGAGQGGYGGLGGQGVGRGGLGGQGAGAAAAGGAGQGGYGGVGSGASAASAAASRLSSPQASSRLSSAVSNLV ATGPTNSAALSSTISNVVSQIGASNPGLSGCDVLIQALLEVVSALIQILGSSSIGQVNYGSAGQATQIVGQSVYQALG |
| 108 | GAGSGGAGGYGRGAGAGAAAAGAGAGAGSYGGQGGYGAGAGAGAAAAAGAGAGAGGYGRGAGAGAGAGA GAAARAGAGAGGAGYGGQGGYGAGAGAGAAAAAGAGAGGAGGYGRGAGAGAGAAAGAGAGAGGYGGQSG YGAGAGAAAAA |
| 109 | GASGAGQGQGYGQQGQGGSSAAAAAAAAAAAQGQGQGYGQQGQGYGQQGQGGSSAAAAAAAAAAAAAAQGQ GQGYGQQGQGSAAAAAAAAAAGASGAGQGQGYGQQGQGGSSAAAAAAAAAAAAAAAAQGQGYGQQGQGSAAA AAAAAAAAA |
| 110 | GGYGPGAGQQGPGSGGQQGPGGQGPYGSGQQGPGGAGQQGPGGQGPYGPGAAAAAAAAAGGYGPGAGQQGPG GAGQQGPGSQGPGGQGPYGPGAGQQGPGSQGPGSGGQQGPGGQGPYGPSAAAAAAAAAGGYGPGAGQRSQGPG GQGPYGPGAGQQGPGSQGPGSGGQQGPGGQGPYGPSAAAAAAAAAGGYGPGAGQQGPGSQGPGSGGQQGPGGQG PYGPGAAAAAAAVGGYGPGAGQQGPGSQGPGSGGQQGPGGQGPYGPSAAAAAAAAAGGYGPGAGQQGPGSQGP GSGGQQGPGGQGPYGPSAAAAAAAAAGGYGPGAGQQGPGSGGQQGPGGQGPYGSGQQGPGGAGQQGPGGQGPY GPGAAAAAAAAAGGYGPGAGQQGPGAGQQGPGSQGPGGQGPYGPGAGQQGPGSQGPGSGGQQGPGGQGPYG PSAAAAAAAAAGGYGPGAGQRSQGPGGQGPYGPGAGQQGPGSQGPGSGGQQGPGGQGPYGPSAAAAAAAAGGY GPGAGQQGPGSQGPGSGGQQGPGGQGPYGPGAAAAAAAVGGYGPGAGQQGPGSQGPGSGGQQGPGGQGPYGPS AAAAAAAAGGYGPGAGQQGPGSQGPGSGGQQGPGGQGPYGPSAAAAAAAAGGYGPGAGQQGPGSGGQQGPGG QGPYGSGQQGPGGAGQQGPGGQGPYGPGAAAAAAAAAGGYGPGAGQQGPGSQGPGSGGQQGPGGQGPYGPGA GQQGPGSQGPGSGGQQGPGGQGPYGPSAAAAAAAAAGGYGPGAGQRSQGPGGQGPYGPGAGQQGPGSQGPGSG GQQGPGGQGPYGPSAAAAAAAAAGGYGPGAGQQGPGSQGPGSGGQQGPGGQGPYGPGAAAAAAAVGGYGPGAG QQGPGSQGPGSGGQQGPGGQGPYGPSAAAAAAAAAGGYGPGAGQQGPGSQGPGSGGQQGPGGQGPYGPSAAAAA AAA |

In some embodiments, the silk or silk or silk-like proteins comprise one or more repeat units comprising SEQ ID NO: 13. This repeat unit contains 6 quasi-repeat units. The quasi-repeat unit can be concatenated 2, 3, 4, 5, 6, 7, 8, 9, 10, 11, 12, 13, 14, 15, 16, 17, 18, 19, or 20 times to form polypeptide molecules from about 50 kDal to about 1,000 kDal. This repeat unit also contains poly-alanine regions related to nano-crystalline regions, and glycine-rich regions related to beta-turn containing less-crystalline regions.

Non-limiting examples of additional suitable silk or silk or silk-like proteins are provided, for example, in International Patent Publication WO/2016/201369, published Dec. 15, 2016; U.S. patent application 62/394,683, filed Sep. 14, 2016; U.S. patent application Ser. No. 15/705,185, filed Sep. 14, 2017, U.S. publication US20160222174, published Aug. 4, 2016; International Patent Publication WO2016/149414, published Mar. 16, 2016; International Patent Publication WO 2014/066374, published Jan. 5, 2014, and International Patent Publication WO 2015/042164, published Mar. 26, 2015, each of which are hereby incorporated by reference in its entirety.

Typically, operable linkage of recombinant proteins with secretion signals requires removal of start codons of the polynucleotide sequences encoding the recombinant proteins.

Other Components

In some embodiments, at least one of the polynucleotide sequences comprised in the recombinant host cells further encode tag peptides or polypeptides operably linked to the C-termini of the proteins. Such tag peptides or polypeptides can aid in purification of the recombinant proteins. Non-limiting examples of tag peptides or polypeptides include affinity tags (i.e., peptides or polypeptides that bind to certain agents or matrices), solubilization tags (i.e., peptides or polypeptides that assist in proper folding of proteins and prevent precipitation), chromatography tags (i.e., peptides or polypeptides that alter the chromatographic properties of a protein to afford different resolution across a particular separation techniques), epitope tags (i.e., peptides or polypeptides that are bound by antibodies), fluorescence tags, chromogenic tags, enzyme substrate tags (i.e., peptides or polypeptides that are the substrates for specific enzymatic reactions), chemical substrate tags (i.e., peptides or polypeptides that are the substrates for specific chemical modifications), or combinations thereof. Non-limiting examples of suitable affinity tags include maltose binding protein (MBP), glutathione-S-transferase (GST), poly(His) tag, SBP-tag, Strep-tag, and calmodulin-tag. Non-limiting examples of suitable solubility tags include thioredoxin (TRX), poly(NANP), MBP, and GST. Non-limiting examples of chromatography tags include polyanionic amino acids (e.g., FLAG-tag) and polyglutamate tag. Non-limiting examples of epitope tags include V5-tag, VSV-tag, Myc-tag, HA-tag, E-tag, NE-tag, Ha-tag, Myc-tag, and FLAG-tag. Non-limiting examples of fluorescence tags include green fluorescent protein (GFP), blue fluorescent protein (BFP), cyan fluorescent protein (CFP), yellow fluorescent protein (YFP), orange fluorescent protein (OFP), red fluorescent protein (RFP), and derivatives thereof. Non-limiting examples of enzyme substrate tags include peptides or polypeptides comprising a lysine within a sequence suitable for biotinilation (e.g., AviTag, Biotin Carboxyl Carrier Protein [BCCP]). Non-limiting examples of chemical substrate tags include substrates suitable for reaction with FlAsH-EDT2. The fusion of the C-terminal tag peptide or polypeptide to the recombinant proteins can be cleavable (e.g., by TEV protease, thrombin, factor Xa, or enteropeptidase) or non-cleavable.

In some embodiments, at least one of the polynucleotide sequences comprised in the recombinant host cells further encode linker peptides operably linked between the recombinant proteins and the secretion signals. The linker peptides can have various sizes. In some such embodiments, the polynucleotide sequences that encode the linker peptides comprise restriction enzyme sites to permit replacement or addition of other polynucleotide sequences.

In some embodiments, the polynucleotide sequences encoding the recombinant proteins comprised in the recombinant host cells are operably linked to promoters such that they drive the transcription of the polynucleotide sequences. The promoters may be constitutive promoters or inducible promoters. Induction may, for example, occur via glucose repression, galactose induction, sucrose induction, phosphate repression, thiamine repression, or methanol induction.

Suitable promoters are promoters that mediate expression of proteins in the recombinant host cells provided herein. Non-limiting examples of suitable promoters include the alcohol oxidase (AOX1) promoter of *Pichia pastoris* (pAOX1), glyceraldehyde-3-phosphate dehydrogenase (GAP) promoter of *Pichia pastoris* (pGAP), YPT1 promoter, 3-phosphoglycerate kinase 1 (PGK1) promoter of *Saccharomyces cerevisae* (pPKG1), SSA4 promoter, HSP82 promoter, GPM1 promoter, KAR2 promoter, triose phosphate isomerase 1 (TPI1) promoter of *Pichia pastoris* (pTPI1), enolase 1 (ENO1) promoter of *Pichia pastoris* (pENO1), PET9 promoter, PEX8 (PER3) promoter, AOX2 promoter, AOD promoter, THI11 promoter, DAS promoter, FLD1 promoter, PH089 promoter, CUP1 promoter, GTH1 promoter, ICL1 promoter, TEF1 promoter, LAC4-PBI promoter, T7 promoter, TAC promoter, GCW14 promoter, GAL1 promoter, λPL promoter, λPR promoter, beta-lactamase promoter, spa promoter, CYC1 promoter, TDH3 promoter, GPD promoter, translation initiation factor 1 (TEF1) promoter of *Saccharomyces cerevisiae*, ENO2 promoter, PGL1 promoter, GAP promoter, SUC2 promoter, ADH1 promoter, ADH2 promoter, HXT7 promoter, PHO5 promoter, and CLB1 promoter. Additional promoters that can be used are known in the art.

In some embodiments, the polynucleotide sequences encoding the recombinant proteins comprised in the recombinant host cells are operably linked to terminators such that they effect termination of transcription of the recombinant polynucleotide sequences. Suitable terminators are terminators that terminate transcription in the recombinant host cells provided herein. Non-limiting examples of suitable terminators include the AOX1 terminator of *Pichia pastoris* (tAOX1), PGK1 terminator, and TPS1 terminator. Additional terminators are known in the art.

The polynucleotide sequences encoding the recombinant proteins comprised in the recombinant host cells can be operably linked to the same promoters and/or terminators, or to at least 2 different promoters and/or terminators.

In some embodiments, the polynucleotide sequences encoding the recombinant proteins comprised in the recombinant host cells further comprise selection markers (e.g., antibiotic resistance genes, auxotrophic markers). Selection markers are known in the art. In some embodiments, the selection markers are drug resistant markers. A drug resistant maker enables cells to detoxify an exogenously added drug that would otherwise kill the cell. Illustrative examples of drug resistant markers include but are not limited to those for resistance to antibiotics such as ampicillin, tetracycline, kanamycin, bleomycin, streptomycin, hygromycin, neomycin, Zeocin™, and the like. In other embodiments, the selection markers are auxotrophic markers. An auxotrophic marker allows cells to synthesize an essential component (usually an amino acid) while grown in media that lacks that essential component. Selectable auxotrophic markers include, for example, hisD, which allows growth in histidine-free media in the presence of histidinol. Other selection markers include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, and a xanthine-guanine phosphoribosyltransferase gene.

Host Cells

The recombinant host cells can be of mammalian, plant, algae, fungi, or microbe origin. Non-limiting examples of suitable fungi include methylotrophic yeast, filamentous yeast, *Arxula adeninivorans, Aspergillus niger, Aspergillus niger* var. *awamori, Aspergillus oryzae, Candida etchellsii, Candida guilliermondii, Candida humilis, Candida lipolytica, Candida pseudotropicalis, Candida utilis, Candida versatilis, Debaryomyces hansenii, Endothia parasitica, Eremothecium ashbyii, Fusarium moniliforme, Hansenula polymorpha, Kluyveromyces lactis, Kluyveromyces marxianus, Kluyveromyces thermotolerans, Morteirella vinaceae* var. *raffinoseutilizer, Mucor miehei, Mucor miehei* var. *Cooney et Emerson, Mucor pusillus* Lindt, *Penicillium roquefortii, Pichia methanolica, Pichia (Komagataella) pastoris, Pichia (Scheffersomyces) stipitis, Rhizopus niveus, Rhodotorula* sp., *Saccharomyces bayanus, Saccharomyces beticus, Saccharomyces cerevisiae, Saccharomyces chevalieri, Saccharomyces diastaticus, Saccharomyces ellipsoideus, Saccharomyces exiguus, Saccharomyces florentinus, Saccharomyces fragilis, Saccharomyces pastorianus, Saccharomyces pombe, Saccharomyces sake, Saccharomyces uvarum, Sporidiobolus johnsonii, Sporidiobolus salmonicolor, Sporobolomyces roseus, Trichoderma reesi, Xanthophyllomyces dendrorhous, Yarrowia lipolytica, Zygosaccharomyces rouxii*, and derivatives and crosses thereof.

Non-limiting examples of suitable microbes include *Acetobacter suboxydans, Acetobacter xylinum, Actinoplane missouriensis, Arthrospira platensis, Arthrospira maxima, Bacillus cereus, Bacillus coagulans, Bacillus licheniformis, Bacillus stearothermophilus, Bacillus subtilis, Escherichia coli, Lactobacillus acidophilus, Lactobacillus bulgaricus, Lactobacillus reuteri, Lactococcus lactis, Lactococcus lactis* Lancefield Group N, *Leuconostoc citrovorum, Leuconostoc dextranicum, Leuconostoc mesenteroides* strain NRRL B-512(F), *Micrococcus lysodeikticus, Spirulina, Streptococcus thermophilus, Streptococcus lactis, Streptococcus lactis* subspecies *diacetylactis, Streptococcus, Streptomyces chattanoogensis, Streptomyces griseus, Streptomyces natalensis,*

*Streptomyces olivaceus, Streptomyces olivochromogenes, Streptomyces rubiginosus, Xanthomonas campestris,* and derivatives and crosses thereof.

Additional strains that can be used as recombinant host cells are known in the art. It should be understood that the term "recombinant host cell" is intended to refer not only to the particular subject cell but to the progeny of such a cell. Because certain modifications may occur in succeeding generations due to either mutation or environmental influences, such progeny may not, in fact, be identical to the parent cell, but is still included within the scope of the term "recombinant host cell" as used herein.

Fermentations

The fermentations provided herein comprise recombinant host cells provided herein and culture media suitable for growing the recombinant host cells. The fermentations are obtained by culturing the recombinant host cells in culture media that provide nutrients needed by the recombinant host cells for cell survival and/or growth. Such culture media typically contain an excess carbon source. Non-limiting examples of suitable carbon sources include monosaccharides, disaccharides, polysaccharides, alcohols, and combinations thereof. Non-limiting examples of suitable monosaccharides include glucose, galactose, mannose, fructose, ribose, xylose, arabinose, ribose, and combinations thereof. Non-limiting examples of suitable disaccharides include sucrose, lactose, maltose, tehalose, cellobiose, and combinations thereof. Non-limiting examples of suitable polysaccharides include raffinose, starch, glycogen, glycan, cellulose, chitin, and combinations thereof. Non-limiting examples of suitable alcohols include methanol and glycol.

The use of at least 2 distinct secretion signals as provided herein promote high secreted yields of recombinant proteins. Accordingly, in various embodiments, the fermentations provided herein comprise at least 1%, 5%, 10%, 20%, or 30%; from 1% to 100%, 90%, 80%, 70%, 60%, 50%, 40%, 30%, 20%, or 10%; from 10% to 100%, 90%, 80%, 70%, 60%, 50%, 40%, 30%, or 20%; from 20% to 100%, 90%, 80%, 70%, 60%, 50%, 40%, or 30%; from 30% to 100%, 90%, 80%, 70%, 60%, 50%, or 40%; from 40% to 100%, 90%, 80%, 70%, 60%, or 50%; from 50% to 100%, 90%, 80%, 70%, or 60%; from 60% to 100%, 90%, 80%, or 70%; from 70% to 100%, 90%, or 80%; from 80% to 100%, or 90%; or from 90% to 100% by weight of total yields of the recombinant protein produced by the recombinant host cells as secreted recombinant protein. In some embodiments, the culture media of the fermentations comprise at least 0.1 g/L, at least 0.5 g/L, at least 1 g/L, at least 2 g/L, at least 5 g/L, at least 7 g/L, at least 10 g/L, at least 15 g/L, or at least 20 g/L; from 0.1 g/L to 30 g/L, to 25 g/L, to 20 g/L, to 15 g/L, to 10 g/L, to 7 g/L, to 5 g/L, to 2 g/L, to 1 g/L, or to 0.5 g/L; from 0.5 g/L to 30 g/L, to 25 g/L, to 20 g/L, to 15 g/L, to 10 g/L, to 7 g/L, to 5 g/L, to 2 g/L, or to 1 g/L; from 1 g/L to 30 g/L, to 25 g/L, to 20 g/L, to 15 g/L, to 10 g/L, to 7 g/L, to 5 g/L, or to 2 g/L; from 2 g/L to 30 g/L, to 25 g/L, to 20 g/L, to 15 g/L, to 10 g/L, to 7 g/L, or to 5 g/L; from 5 g/L to 30 g/L, to 25 g/L, to 20 g/L, to 15 g/L, to 10 g/L, or to 7 g/L; from 7 g/L to 30 g/L, to 25 g/L, to 20 g/L, to 15 g/L, or to 10 g/L; from 10 g/L to 30 g/L, to 25 g/L, to 20 g/L, or to 15 g/L; from 15 g/L to 30 g/L, to 25 g/L, or to 20 g/L; from 20 g/L to 30 g/L, or to 25 g/L; or from 25 g/L to 30 g/L of the recombinant proteins produced by the recombinant host cells.

Methods of Producing High Secreted Yields of Recombinant Proteins

Provided herein are methods for producing high secreted yields of recombinant proteins. The methods are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y., 1989; Ausubel et al. Current Protocols in Molecular Biology, Greene Publishing Associates, 1992, and Supplements to 2002); Harlow and Lane, Antibodies: A Laboratory Manual, Cold Spring Harbor Laboratory Press, Cold Spring Harbor, N.Y., 1990; Taylor and Drickamer, Introduction to Glycobiology, Oxford Univ. Press, 2003; Worthington Enzyme Manual, Worthington Biochemical Corp., Freehold, N.J.; Handbook of Biochemistry: Section A Proteins, Vol I, CRC Press, 1976; Handbook of Biochemistry: Section A Proteins, Vol II, CRC Press, 1976; Essentials of Glycobiology, Cold Spring Harbor Laboratory Press, 1999.

The methods provided herein comprise the step of culturing recombinant host cells provided herein in culture media under conditions suitable for obtaining the fermentations provided herein (step 1003 in FIG. 1). Suitable culture media for use in these methods are known in the art, as are suitable culture conditions. Details of culturing yeast host cells, for example, are described in Idiris et al. (2010) Appl. Microbiol. Biotechnol. 86:403-417; Zhang et al. (2000) Biotechnol. Bioprocess. Eng. 5:275-287; Zhu (2012) Biotechnol. Adv. 30:1158-1170; and Li et al. (2010) MAbs 2:466-477.

In some embodiments, the methods further comprise the step of constructing recombinant vectors that comprise the polynucleotide sequences encoding the recombinant proteins operably linked to the secretion signals (step 1001 in FIG. 1). Methods for constructing recombinant vectors are known in the art. In some embodiments, the recombinant vectors are synthetically generated. In other embodiments, the recombinant vectors are isolated or PCR amplified by standard procedures from organisms, cells, tissues, or plasmid constructs. In some embodiments, the polynucleotide sequences encoding the recombinant proteins are codon-optimized for expression in particular host cells.

In some embodiments, the methods comprise the step of balancing expression of the recombinant proteins (e.g., by increasing or reducing the number of polynucleotide sequences and/or the strengths of the promoters that are operably linked to the polynucleotide sequences) and efficiency of secretion of the recombinant proteins (e.g., by choosing distinct secretion signals or combinations of distinct secretion signals).

In some embodiments, the methods further comprise the step of transforming cells with recombinant vectors to obtain recombinant host cells provided herein (step 1002 in FIG. 1). For such transformations, the recombinant vectors can be circularized or be linear. Methods for transforming cells are well-known in the art. Non-limiting examples of such methods include calcium phosphate transfection, dendrimer transfection, liposome transfection (e.g., cationic liposome transfection), cationic polymer transfection, electroporation, cell squeezing, sonoporation, optical transfection, protoplast fusion, impalefection, hydrodynamic delivery, gene gun, magnetofection, spheroblast generation, polyethylene glycol (PEP) treatment, and viral transduction. One skilled in the art is able to select one or more suitable methods for transforming cells with expression constructs or recombinant vectors provided herein based on the knowledge in the art that certain techniques for introducing vectors work better for certain types of cells. Recombinant host cell transformants comprising expression constructs or recombinant vectors provided herein can be readily identified, e.g., by virtue of expressing drug resistance or auxotrophic markers encoded by the recombinant vectors that permit selection for or against growth of cells, or by other means (e.g., detection of light emitting peptide comprised in the expression constructs or recombinant vectors, molecular analysis of individual recombinant host cell colonies [e.g., by restriction enzyme mapping, PCR amplification, or sequence analysis of isolated extrachromosomal vectors or chromosomal integration sites]). In some embodiments, the methods comprise successive transformations of host cells with 2 or more recombinant vectors.

In some embodiments, the methods further comprise the step of extracting the secreted recombinant proteins from fermentations provided herein (step 1004 in FIG. 1). Extractions can occur by a variety of methods known in the art for purifying secreted proteins. Common steps in such methods include centrifugation at speeds that cause the pelleting of cells and removal of cell pellets comprising the recombinant host cells and cell debris, followed by precipitation of the recombinant proteins using precipitants (e.g., ammonium sulfate at 5-60% saturation; followed by centrifugation) or affinity separation (e.g., by immunological interaction with antibodies that bind specifically to the recombinant proteins or their C-terminal tags [e.g., FLAG, hemagglutinin], or via binding to nickel columns for isolation of polypeptides tagged with 6 to 8 histidine residues (SEQ ID NO: 120)). The suspended recombinant proteins can be dialyzed to remove the dissolved salts. Additionally, the dialyzed recombinant proteins can be heated to denature other proteins, and the denatured proteins can be removed by centrifugation.

EXAMPLES

Example 1: Generation of *Pichia pastoris* Recombinant Host Cells that Produce High Yields of Secreted Recombinant Proteins

*Pichia pastoris* (*Komagataella phaffii*) recombinant host cells that secrete a silk-like protein were generated by transforming a HIS+ derivative of GS115 (NRRL Y15851) with a first recombinant vector and a second recombinant vector.

Figure 2A:
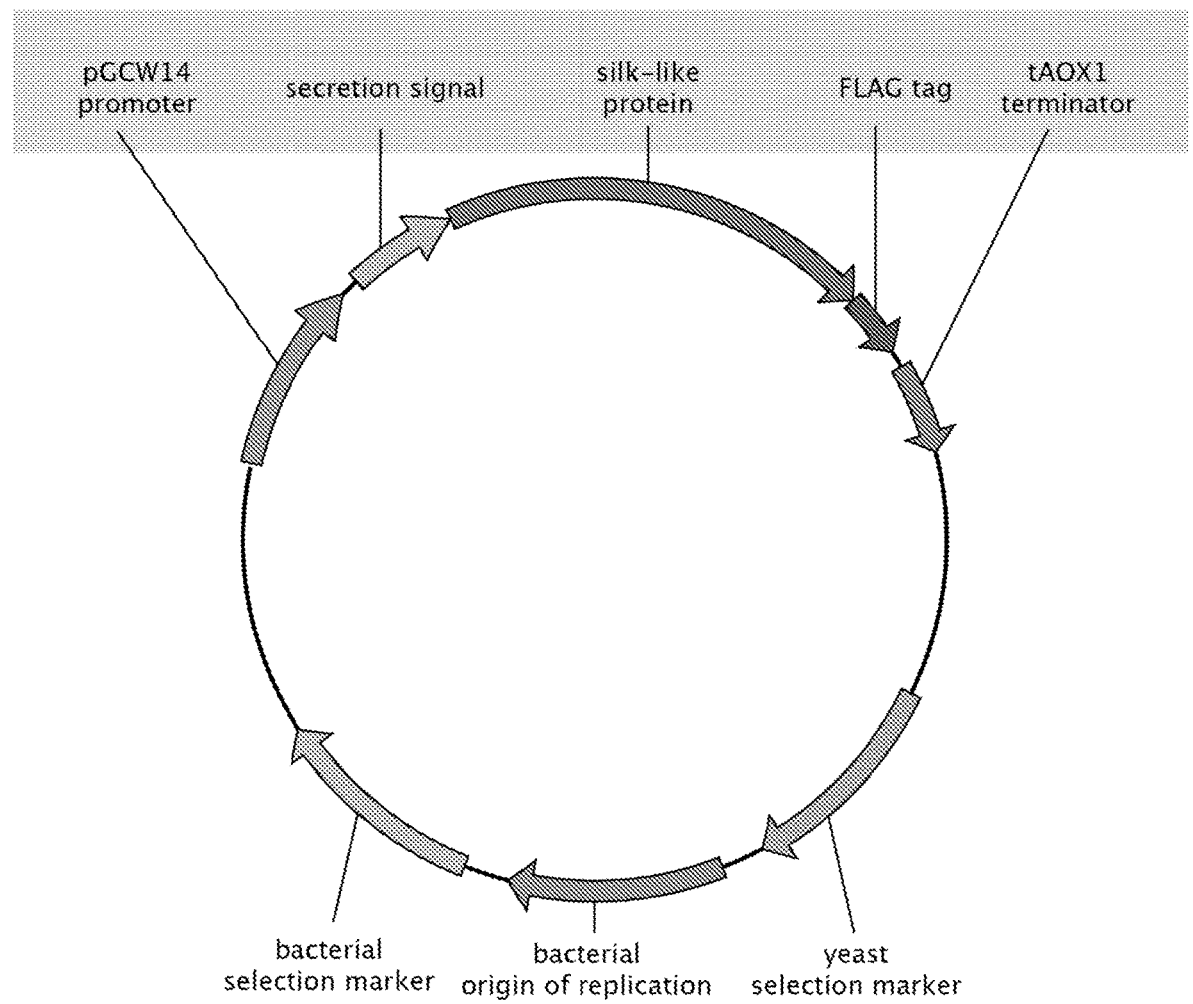
FIG. 2A and FIG. 2B are illustrative maps of recombinant vectors that comprise one (FIG. 2A) or 3 (FIG. 2B) polynucleotide sequences encoding a silk-like protein operably linked to an N-terminal secretion signal comprising a functional variant of the secretion signal of the α-mating factor of *Saccharomyces cerevisiae* (pre-αMF(sc)/*pro-αMF(sc)) or a recombinant secretion signal consisting of a functional variant of the leader peptide of the α-mating factor of *Saccharomyces cerevisiae* (*pro-αMF(sc)) and a signal peptide.
Figure 2B:
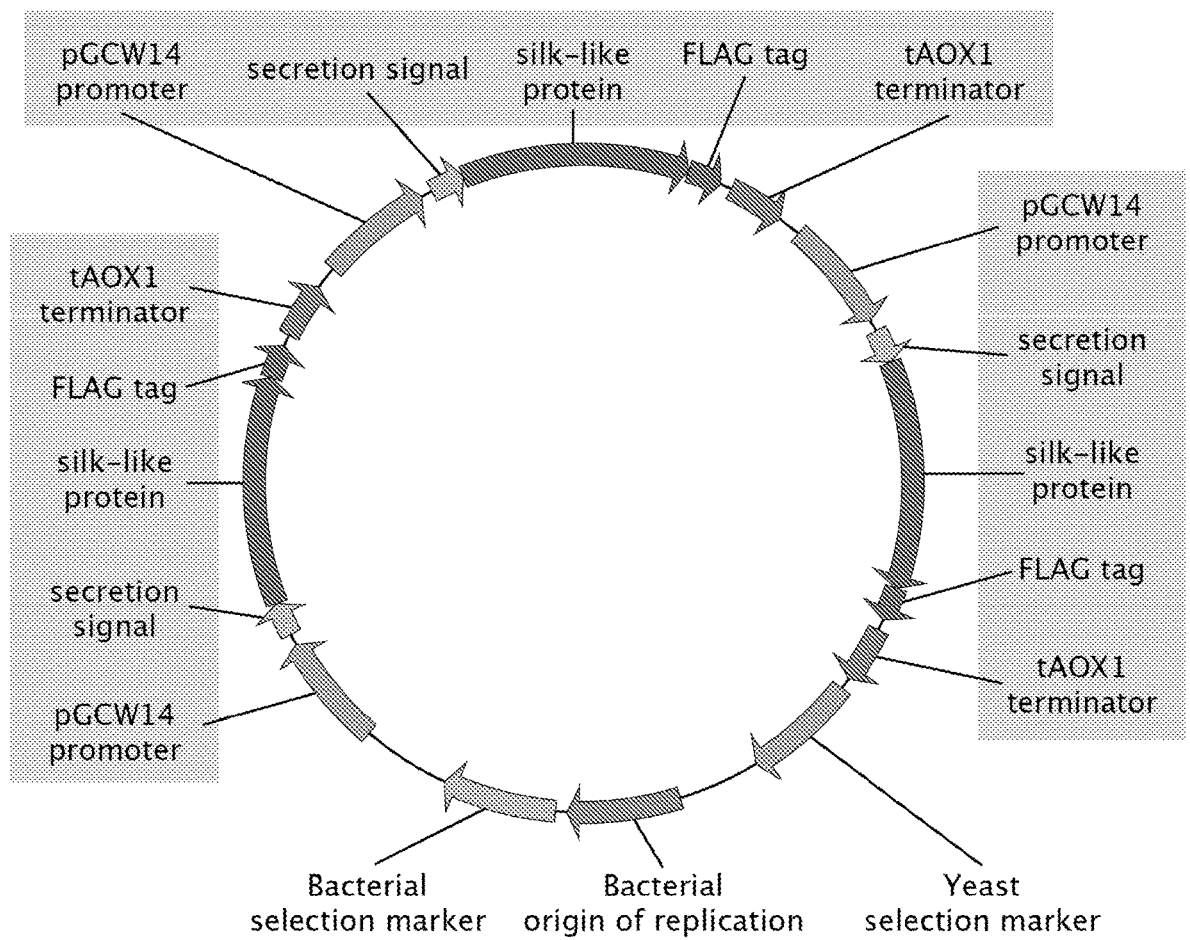

The recombinant vectors (see FIG. 2) comprised a polynucleotide sequence encoding the silk-like protein (SEQ ID NO: 110) operably linked either to pre-αMF(sc)/*pro-αMF(sc) (SEQ ID NO: 8) or to various recombinant secretion signals that consisted of *pro-αMF(sc) (SEQ ID NO: 2) and a signal peptide. The silk-like protein was further operably linked to a C-terminal FLAG-tag.

The polynucleotide sequences encoding the silk-like protein in the recombinant vectors were flanked by a promoter (pGCW14) and a terminator (tAOX1 pA signal). The recombinant vectors further comprised dominant resistance markers for selection of bacterial and yeast transformants, and a bacterial origin of replication. The recombinant vectors further comprised targeting regions that directed integration of the polynucleotide sequences immediately 3' of the HIS4, HSP82, AOX2, TEF1, MAE1, or ICL1 loci in the *Pichia pastoris* genome.

The recombinant vectors were successively transformed into the *Pichia pastoris* host cells via electroporation to generate recombinant host strains. Transformants were plated on either minimal agar plates lacking histidine, or YPD agar plates supplemented with antibiotics, and incubated for 48 hours at 30° C.

Resulting clones were inoculated into 400 µL of Buffered Glycerol-complex Medium (BMGY) in 96-well blocks, and incubated for 48 hours at 30° C. with agitation at 1,000 rpm. Following the 48-hour incubation, 4 µL of each culture was used to inoculate 400 µL of minimal media in 96-well blocks, which were then incubated for 48 hours at 30° C.

Guanidine thiocyanate was added to a final concentration of 2.5M to the cell cultures to extract the recombinant protein for measurement by ELISA. After a 5 min incubation, solutions were centrifuged and the supernatant was sampled (producing the data labeled Extracellular in FIGS. 3 through 5). The supernatant was removed by inversion, and the remaining cell pellets were resuspended to the original volume in guanidine thiocyanate. Cells were lysed by mechanical disruption in a bead mill, and the resulting lysate was cleared by centrifugation and sampled (producing the data labeled Intracellular in FIGS. 3 through 5).

Figure 3:
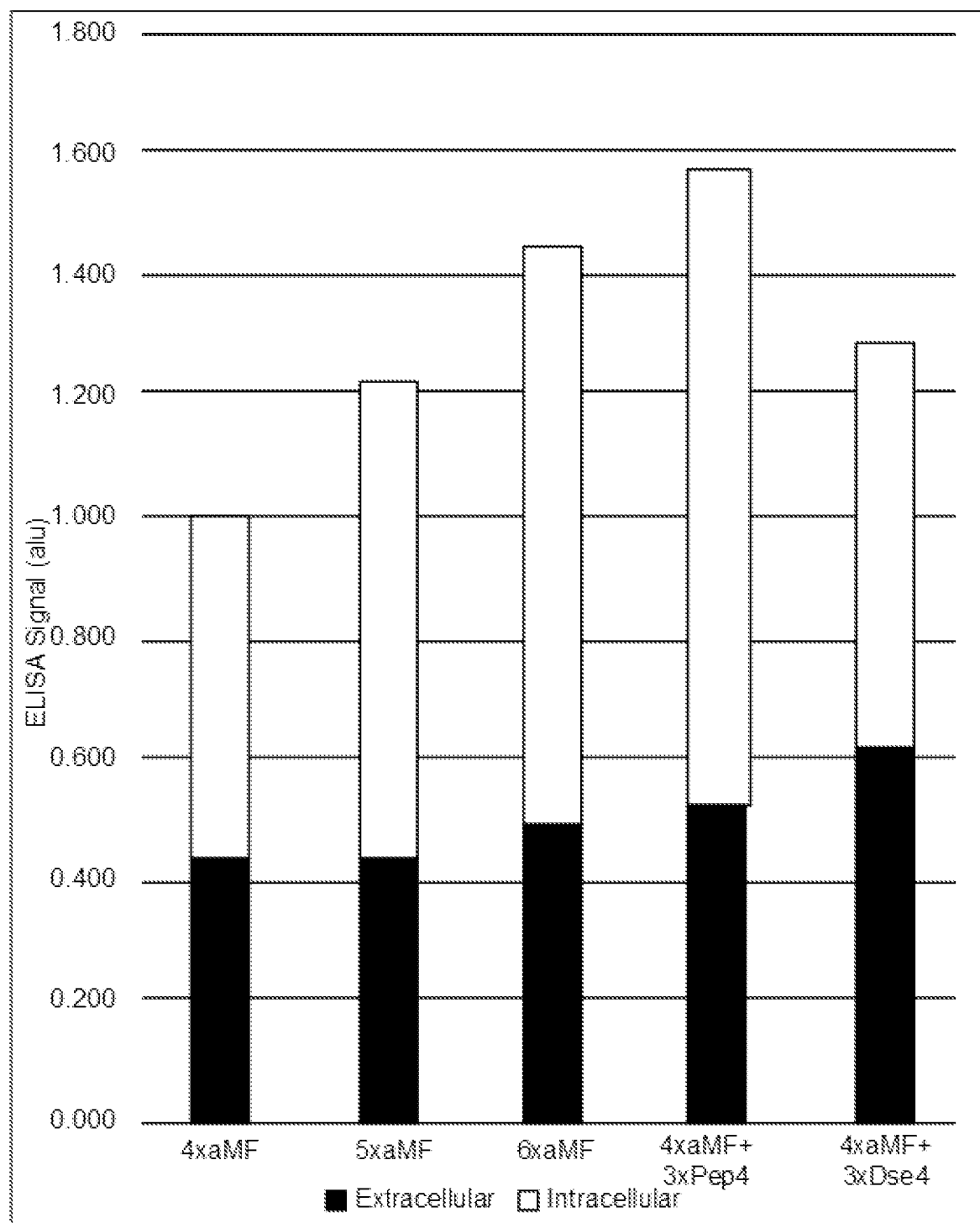
FIG. 3, FIG. 4 and FIG. 5 show intracellular (non-secreted) and extracellular (secreted) yields of a recombinant silk-like protein produced by various Pichia pastoris recombinant host cells as assayed by ELISA. Legend: 4/5/6×αMF=recombinant host strain comprising 4/5/6 polynucleotide sequences encoding the silk-like protein operably linked to signal sequence pre-αMF(sc)/*pro-αMF(sc) (SEQ ID NO: 8); 4×αMF+3×Pep4=recombinant host strain 4×αMF further comprising 3 polynucleotide sequences encoding the silk-like protein operably linked to signal sequence pre-PEP4(sc)/*pro-αMF(sc) (SEQ ID NO: 9); 4×αMF+3×Dse4=recombinant host strain 4×αMF further comprising 3 polynucleotide sequences encoding the silk-like protein operably linked to signal sequence pre-DSE4 (pp)/*pro-αMF(sc) (SEQ ID NO: 10); 4×αMF+2×Epx1=recombinant host strain 4×αMF further comprising 2 polynucleotide sequences encoding the silk-like protein operably linked to signal sequence pre-EPX1(pp)/*pro-αMF(sc) (SEQ ID NO: 11); and 4×αMF+2×Epx1+1×CLSP=recombinant host strain 4×αMF+2×Epx1 further comprising 1 polynucleotide sequence encoding the silk-like protein operably linked to signal sequence pre-CLSP(gg)/*pro-αMF(sc) (SEQ ID NO: 12).

As shown in FIG. 3, increasing the number of polynucleotide sequences encoding the silk-like protein operably linked to pre-αMF(sc)/*pro-αMF(sc) from 4 to 6 provided higher overall production of the silk-like protein but did not as significantly increase its secreted yield. As further shown in FIG. 3, recombinant host cells comprising 7 copies of a polynucleotide sequence encoding the silk-like protein operably linked to 2 distinct secretion signals (namely, pre-αMF(sc)/*pro-αMF(sc) in 4 polynucleotide sequences and pre-DSE4(pp)/*pro-αMF(sc) or pre-PEP4(sc)/*pro-αMF(sc) in 3 polynucleotide sequences) produced higher secreted yields than recombinant host cells comprising 6 copies of a polynucleotide sequence encoding the silk-like protein operably linked to a single type of secretion signal (namely, pre-αMF(sc)/*pro-αMF(sc)). Note that recombinant host cells comprising 7 copies of a polynucleotide sequence encoding the silk-like protein operably linked to the pre-αMF(sc)/*pro-αMF(sc) secretion signal could not be obtained for direct comparison; speculatively, this may indicate that such host cells are unstable and/or inviable.

Figure 4:
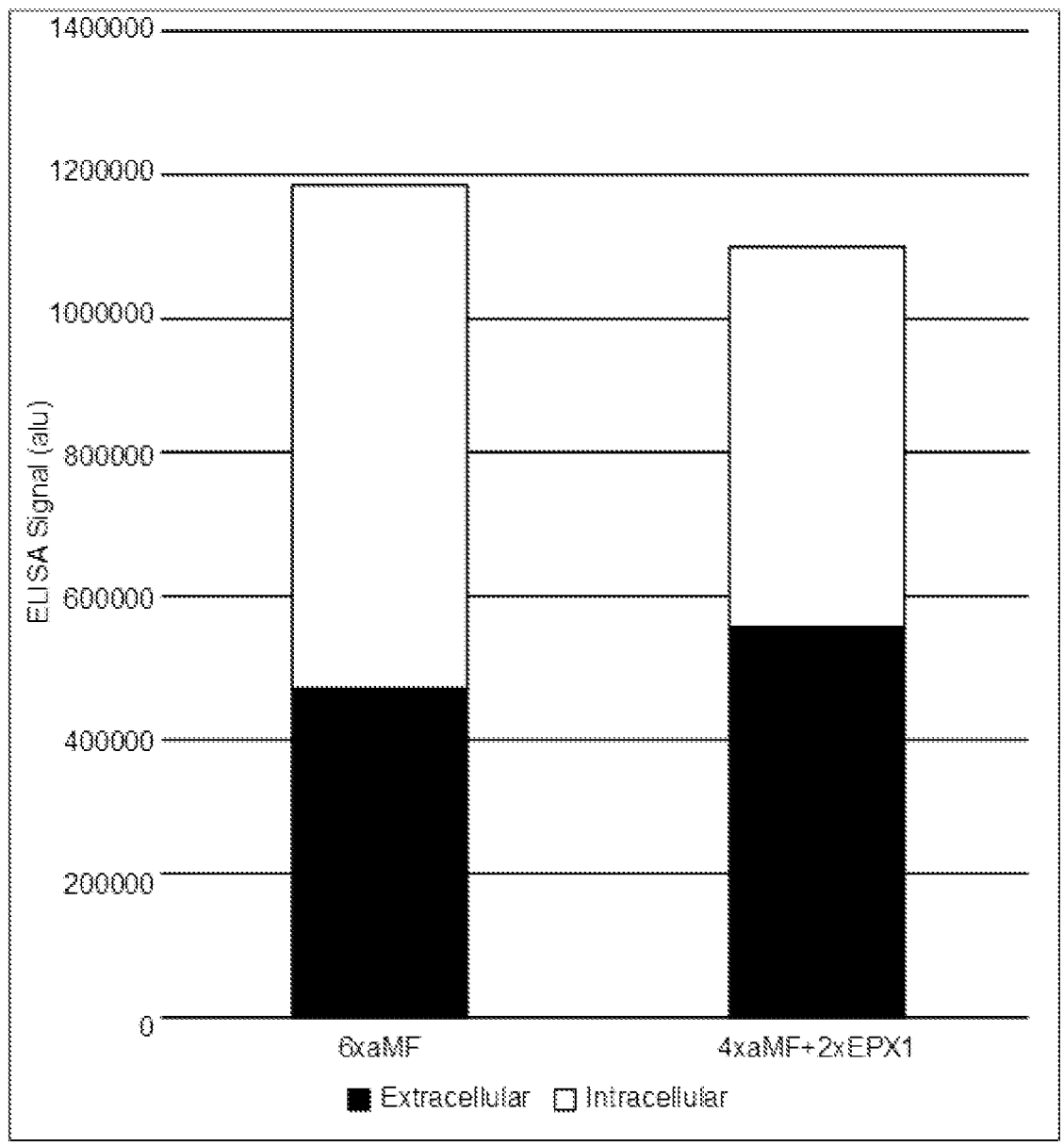

As shown in FIG. 4, a recombinant host cell comprising 6 copies of a polynucleotide sequence encoding the silk-like protein operably linked to 2 distinct secretion signals (namely pre-αMF(sc)/*pro-αMF(sc) in 4 polynucleotide sequences and pre-EPX1(pp)/*pro-αMF(sc) in 2 polynucleotide sequences) produced higher secreted yields and percent secreted of the silk-like protein than a recombinant host cell comprising the same number of polynucleotide sequences encoding the silk-like protein operably linked to a single type of secretion signal (namely, pre-αMF(sc)/*pro-αMF(sc)).

Figure 5:
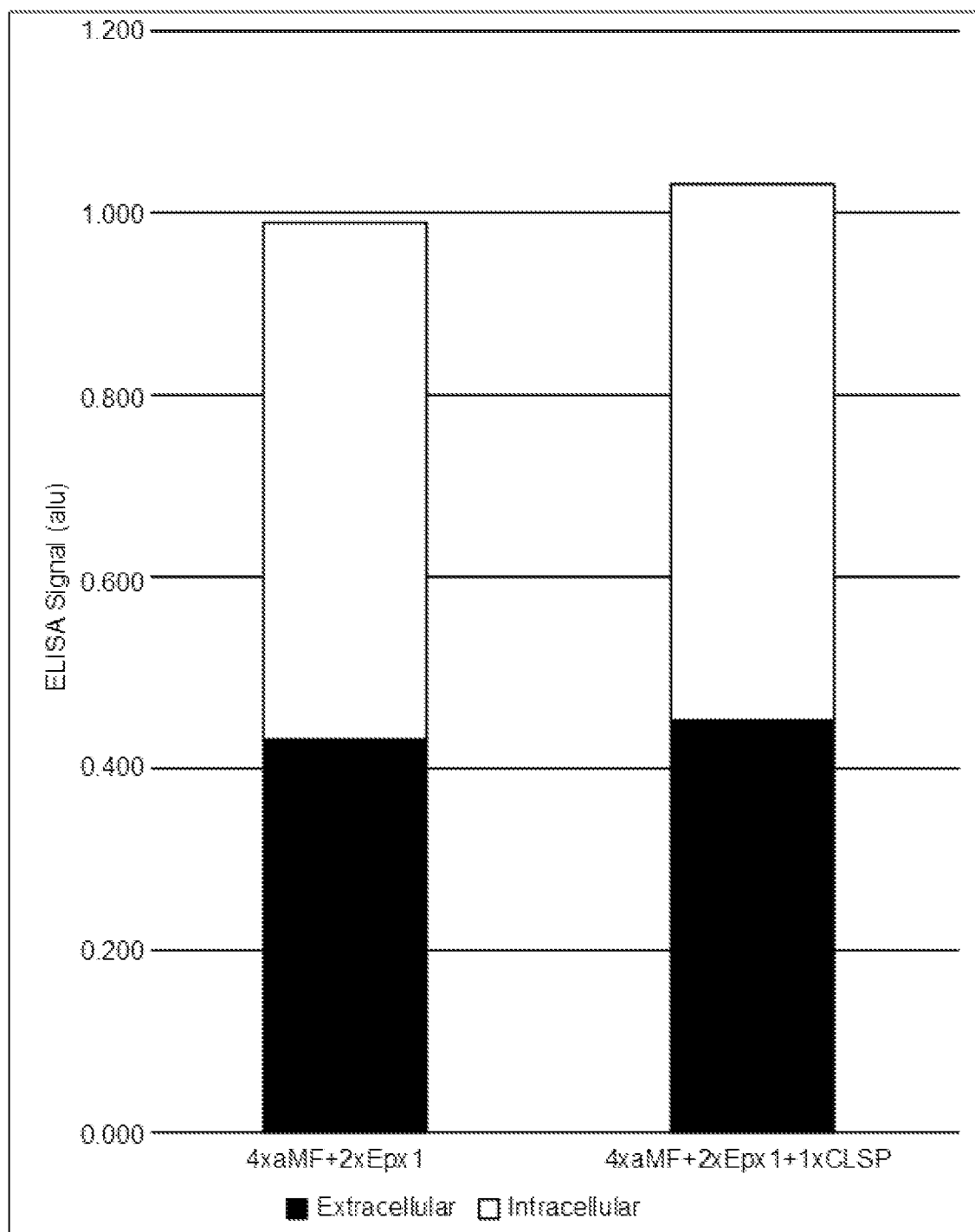

As shown in FIG. 5, adding a third recombinant secretion signal (namely, pre-CLSP(gg)/*pro-αMF(sc)) to the 4+2× EPX1(pp) strain of FIG. 4 further improved secreted yield of the silk-like protein. Note that cells comprising 7 copies of a polynucleotide sequence encoding the silk-like protein operably linked to the pre-αMF(sc)/*pro-αMF(sc) secretion signal, or comprising 4 copies of a polynucleotide sequence encoding the silk-like protein operably linked to the pre-αMF(sc)/*pro-αMF(sc) secretion signal and 3 copies of a polynucleotide sequence encoding the silk-like protein operably linked to the pre-EPX1(pp)/*pro-αMF(sc) secretion signal could not be obtained for direct comparison; speculatively, this may indicate that such host cells are unstable and/or inviable.

Example 2: Generation of *Pichia pastoris* Recombinant Host Cells that Produce High Secreted Yields of Alpha-Amylase or Green Fluorescent Protein

*Pichia pastoris* (*Komagataella phaffii*) recombinant host cells that secrete either an alpha-amylase or green fluorescent protein were generated by transforming a HIS+ derivative of GS115 (NRRL Y15851) with various recombinant vectors.

Figure 6:
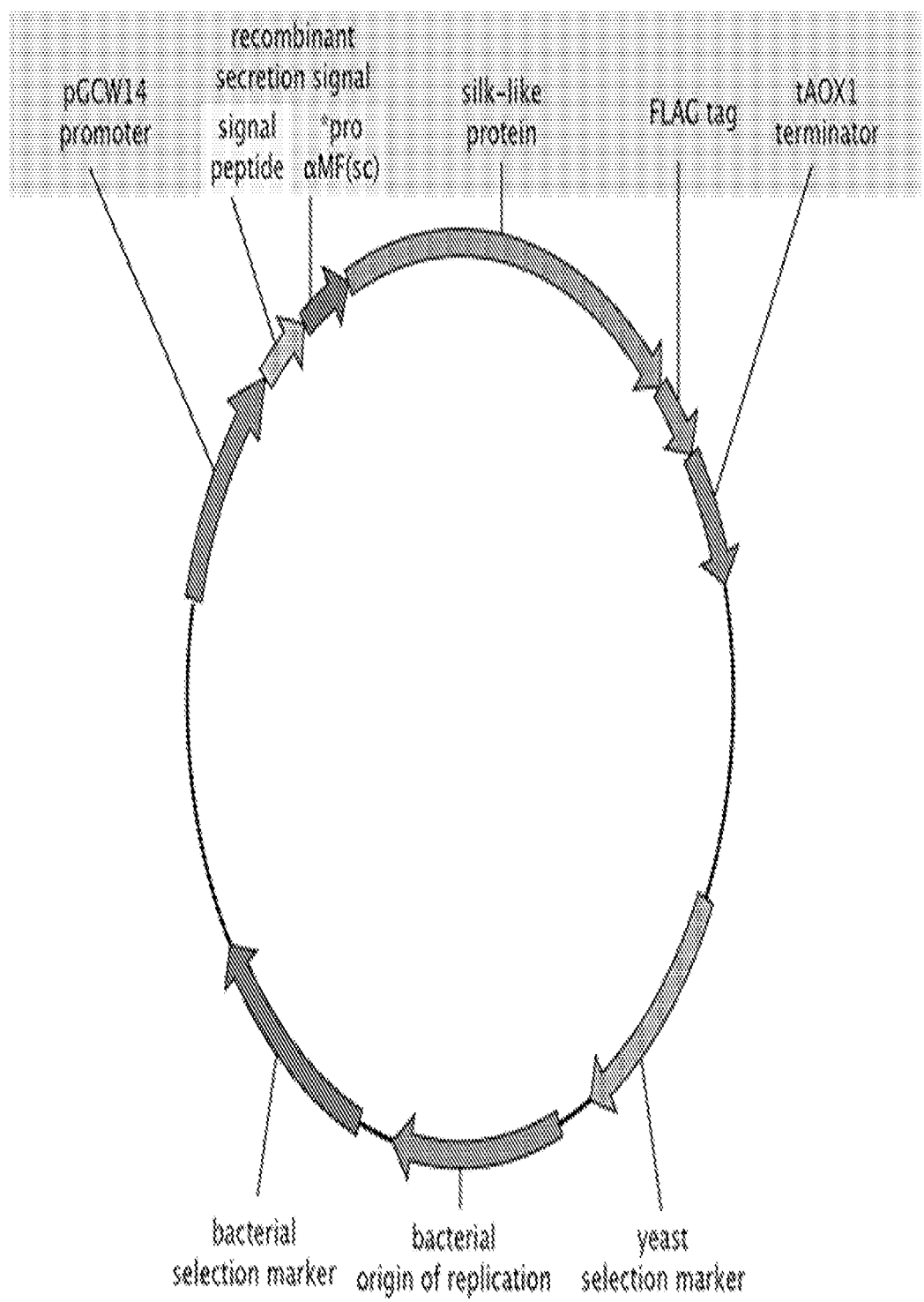
FIG. 6 is a diagram of a recombinant vector comprising an expression construct for expressing a polypeptide with recombinant secretion signals, according to an embodiment of the invention.

The recombinant vectors (see FIG. 6) comprised an expression construct that comprised a polynucleotide sequence encoding either alpha-amylase (SEQ ID NO: 111) or green fluorescent protein (SEQ ID NO: 112) operably linked to various N-terminal recombinant secretion signals. The recombinant secretion signals consisted of an N-terminal signal peptide operably linked to *pro-αMF(sc) (SEQ ID NO:2). The alpha-amylase or green fluorescent protein was further operably linked to a C-terminal FLAG-tag. Each of the polynucleotide sequences was flanked by a promoter (pGCW14) and a terminator (tAOX1 pA signal). The recombinant vectors further comprised a targeting region that directed integration of the expression construct to the region immediately 3' of the THI4 locus in the *Pichia pastoris* genome, dominant resistance markers for selection of bacterial and yeast transformants, and a bacterial origin of replication.

Figure 7:
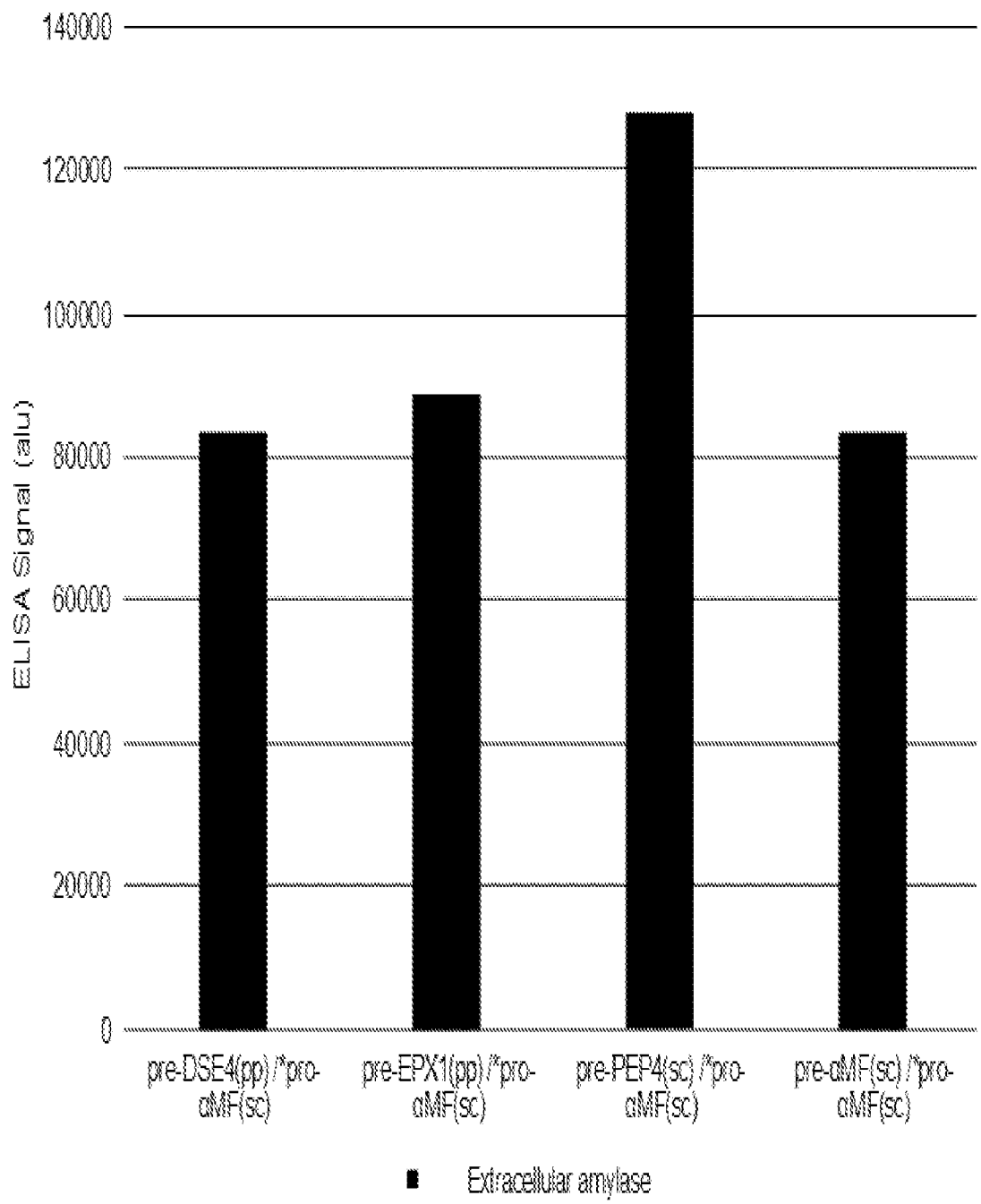
FIG. 7 illustrates secretion levels of alpha-amylase from Pichia pastoris transformed to express recombinant alpha-amylase with various recombinant secretion signals.

As shown in FIG. 7, the pre-EPX1(pp)/*pro-αMF(sc) and the pre-PEP4(sc)/*pro-αMF(sc) recombinant secretion signals produced higher secreted yields of amylase than the pre-αMF(sc)/*pro-αMF(sc) recombinant secretion signal while the pre-DSE4(pp)/*pro-αMF(sc) secretion signal produced roughly the same amount of secreted amylase.

Figure 8:
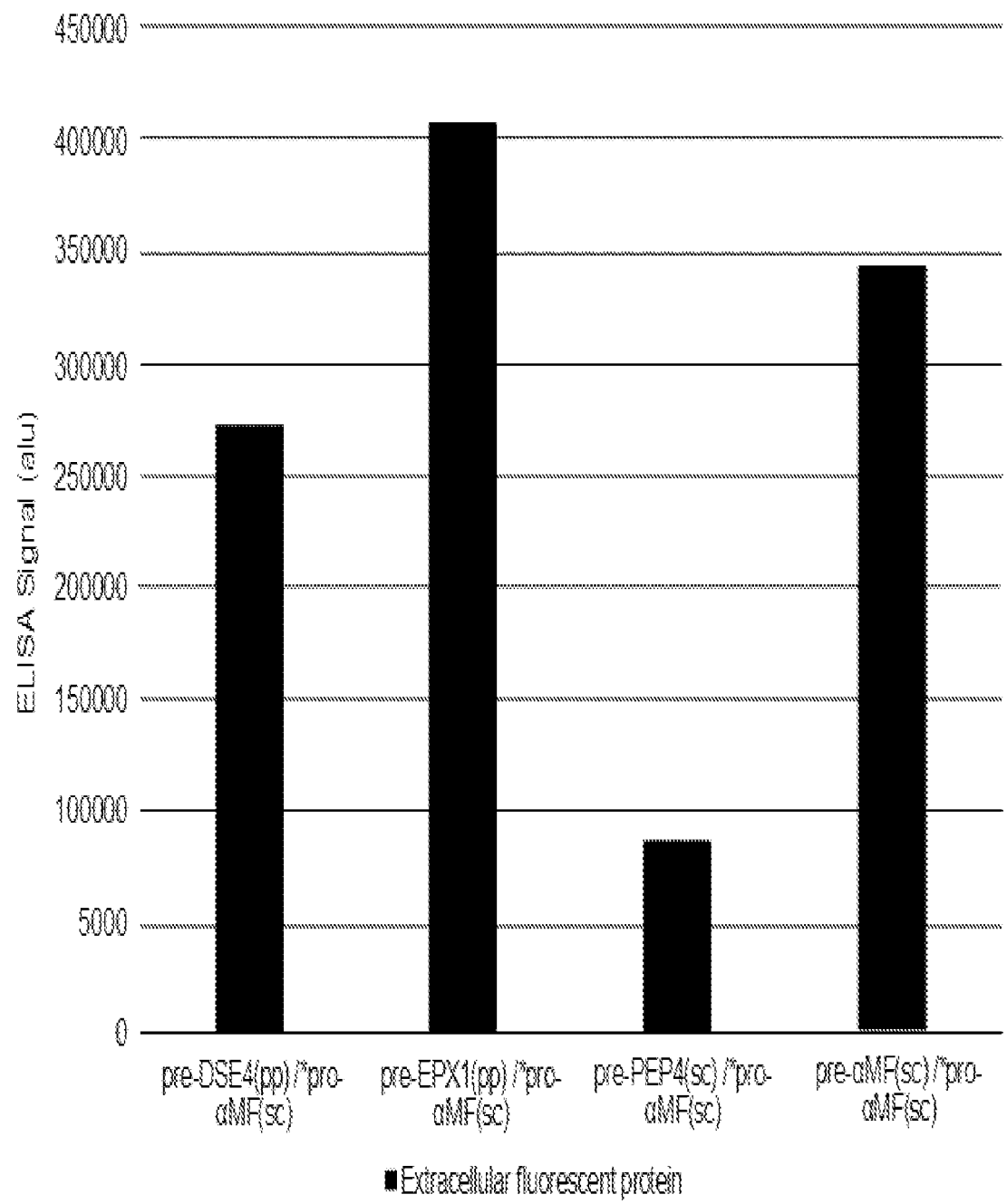
FIG. 8 illustrates secretion levels of fluorescent protein from Pichia pastoris transformed to express recombinant fluorescent protein with various recombinant secretion signals.

As shown in FIG. 8, the pre-EPX1(pp)/*pro-αMF(sc) recombinant secretion signal produced higher secreted yields of green fluorescent protein than the pre-αMF (sc)/*pro-αMF(sc) recombinant secretion signal, while the pre-PEP4(sc)/*pro-αMF(sc) and the pre-DSE4(pp)/*pro-αMF(sc) secretion signals produced less secreted fluorescent protein.

The foregoing description of the embodiments of the disclosure has been presented for the purpose of illustration; it is not intended to be exhaustive or to limit the scope of the invention.

In the examples, efforts have been made to ensure accuracy with respect to numbers used (e.g., amounts, temperatures, etc.), but some experimental error and deviation should, of course, be allowed for. The reagents employed in the examples are generally commercially available or can be prepared using commercially available instrumentation, methods, or reagents known in the art. The examples are not intended to provide an exhaustive description of the many different embodiments of the invention. Those of ordinary skill in the art will realize readily that many changes and modifications can be made to the embodiments presented in the examples without departing from the spirit or scope of the appended claims.

TABLE 4

Recombinant Proteins Expressed

| SEQ ID NO | Name | Amino Acid Sequence |
|---|---|---|
| 111 | alpha-amylase | ANLNGTLMQYFEWYMPNDGQHWKRLQNDSAYLAEHGITAVWIPPAYK GTSQDDVGYGAYDLYDLGEFHQKGTVRTKYGTKGELQSAINSLHSRDIN VYGDVVINHKGGADATEDVTAVEVDPADRNRVTSGEQRIKAWTHFQFP GRGSTYSDFKWHWYHFDGTDWDESRKLNRIYKFQGKAWDWEVSNVNG NYDYLMYADIDYDHPDATAEIKRWGTWYANELQLDGFRLDAVKHIKFSF LRDWVNHVREKTGKEMFTVAEYWQNDLGALENYLNKTNFNHSVFDVPL HYQFHAASTQGGGYDMRKLLNGTVVSKHPVKAVTFVDNHDTQPGQSLE STVQTWFKPLAYAFILTREAGYPQIFYGDMYGTKGASQREIPALKHKIEPI LKARIQYAYGAQHDYFDHHDIVGWTREGDSSVANSGLAALITDGPGGTK RMYVGRQNAGETWHDITGNRSDSVVINAEGWGEFHVNGGSVSIYVQR |
| 112 | green fluorescent protein | TALTEGAKLFEKEIPYITELEGDVEGMKFIIKGEGTGDATTGTIKAKYICTT GDLPVPWATLVSTLSYGVQCFAKYPSHIKDFFKSAMPEGYTQERTISFEG DGVYKTRAMVTYERGSIYNRVTLTGENFKKDGHILRKNVAFQCPPSILYI LPDTVNNGIRVEFNQAYDIEGVTEKLVTKCSQMNRPLAGSAAVHIPRYHH ITYHTKLSKDRDERRDHMCLVEVVKAVDLDTYQ |

The recombinant vectors were transformed into the *Pichia pastoris* host cells via electroporation to generate recombinant host strains. Transformants were plated on YPD agar plates supplemented with antibiotics, and incubated for 48-96 hours at 30° C.

Clones from each final transformation were inoculated into 400 μL of Buffered Glycerol-complex Medium (BMGY) in 96-well blocks, and incubated for 48 hours at 30° C. with agitation at 1,000 rpm. Following the 48-hour incubation, 4 μL of each culture was used to inoculate 400 μL of minimal media in 96-well blocks, which were then incubated for 48 hours at 30° C.

Guanidine thiocyanate was added to a final concentration of 2.5 M to the cell cultures to extract the recombinant protein for measurement by ELISA. After a 5 min incubation, solutions were centrifuged and the supernatant was sampled.

TABLE 5 pro-αMF sequences

| SEQ ID NO | Name | Sequence |
|---|---|---|
| 1 | native pro-αMF(sc) | APVNTTTEDETAQIPAEAVIGYLDLEGDF DVAVLPFSNSTNNGLLFINTTIASIAAKE EGVSLDKREAEA |
| 2 | pro-αMF(sc) comprising 2 amino acid substitutions | APVNTTTEDETAQIPAEAVIGYSDLEGDF DVAVLPFSNSTNNGLLFINTTIASIAAKE EGVSLEKREAEA |

What is claimed is:

1. A recombinant host cell comprising a first polynucleotide sequence and a second polynucleotide sequence encoding a structurally identical recombinant protein fused to distinct secretion signals, wherein said recombinant protein encoded by said first polynucleotide sequence is operably linked to a first secretion signal comprising a pre-region of an α-mating factor signal sequence of S. cerevisiae and a pro-region of an α-mating factor signal sequence of S. cerevisiae, wherein said first secretion signal comprises SEQ ID NO: 8, and wherein said recombinant protein encoded by said second polynucleotide sequence is operably linked to a second secretion signal comprising a pre-region of a PEP4 signal sequence of S. cerevisiae and a functional variant of a pro-region of an α-mating factor signal sequence of S. cerevisiae, wherein said second secretion signal comprises SEQ ID NO: 9 or a functional secretion signal variant thereof at least 90% identical to SEQ ID NO: 9.

2. The recombinant host cell of claim 1, wherein said protein is a silk protein.

3. The recombinant host cell of claim 2, wherein said protein comprises SEQ ID NO: 13.

4. The recombinant host cell of claim 2, wherein said protein comprises multiple copies of SEQ ID NO: 13.

5. The recombinant host cell of claim 1, wherein said recombinant protein comprises a sequence selected from the group consisting of SEQ ID NOs: 13-110.

6. The recombinant host cell of claim 1, wherein said recombinant protein comprises a repeat unit of a silk protein.

7. The recombinant host cell of claim 1, wherein said recombinant protein comprises SEQ ID NO: 110.

8. The recombinant host cell of claim 1, wherein said recombinant host cell is a yeast cell.

9. The recombinant host cell of claim 1, wherein said recombinant host cell is Pichia pastoris.

10. A fermentation comprising the recombinant host cell of claim 1 and a culture medium.

11. The fermentation of claim 10, wherein said host cell is P. pastoris.

12. The fermentation of claim 10, wherein aid recombinant protein comprises a repeat unit of a silk protein.

13. The fermentation of claim 10, wherein said recombinant protein comprises a silk protein.

14. The fermentation of claim 10, wherein said recombinant protein comprises a sequence selected from the group consisting of SEQ ID NO: 13-110.

15. A method for producing a recombinant protein, comprising the steps of:
   culturing a recombinant host cell of claim 1 in a culture medium to obtain a fermentation; and
   extracting said recombinant protein from the culture medium.

16. The method of claim 15, wherein said host cell is *P. pastoris*.

17. The method of claim 15, wherein said recombinant protein comprises a repeat unit of a silk protein.

18. The method of claim 15, wherein said recombinant protein comprises a silk protein.

19. The method of claim 15, wherein said recombinant protein comprises a sequence selected from the group consisting of SEQ ID NO: 13-110.

\* \* \* \* \*